(12) United States Patent
Roussel et al.

(10) Patent No.: US 8,962,842 B2
(45) Date of Patent: Feb. 24, 2015

(54) 2-PYRIDONE ANTIMICROBIAL COMPOSITIONS

(75) Inventors: Patrick Roussel, Mulhouse (FR); Jutta Heim, Ramlinsburg (CH); Peter Schneider, Bottmingen/BL (CH); Christian Bartels, Allschwil/BL (CH); Yaoquan Liu, Castro Valley, CA (US); Glen Dale, Basel (CH); Daniel Milligan, San Francisco, CA (US)

(73) Assignee: Evolva SA, Reinach (CH)

( * ) Notice: Subject to any disclaimer, the term of this patent is extended or adjusted under 35 U.S.C. 154(b) by 0 days.

(21) Appl. No.: 13/821,250

(22) PCT Filed: Sep. 16, 2011

(86) PCT No.: PCT/US2011/052003
§ 371 (c)(1),
(2), (4) Date: May 28, 2013

(87) PCT Pub. No.: WO2012/047487
PCT Pub. Date: Apr. 12, 2012

(65) Prior Publication Data
US 2013/0245035 A1    Sep. 19, 2013

Related U.S. Application Data

(60) Provisional application No. 61/386,721, filed on Sep. 27, 2010.

(51) Int. Cl.
C07D 455/02 (2006.01)
A61K 31/4375 (2006.01)

(52) U.S. Cl.
CPC .................................. C07D 455/02 (2013.01)
USPC ...................... 546/138; 514/306; 514/253.04

(58) Field of Classification Search
USPC .......................................... 514/306; 546/138
See application file for complete search history.

(56) References Cited

U.S. PATENT DOCUMENTS

| | | | | |
|---|---|---|---|---|
| 4,772,605 A * | 9/1988 | Naik et al. | ............... | 514/253.08 |
| 5,977,133 A | 11/1999 | Fung et al. | | |
| 7,223,773 B2 * | 5/2007 | Fukumoto et al. | ............ | 514/306 |
| 2013/0252882 A1 * | 9/2013 | Heim et al. | ..................... | 514/2.8 |

FOREIGN PATENT DOCUMENTS

| EP | 0 308 019 A2 | 3/1989 |
|---|---|---|
| EP | 1 227 096 B1 | 9/2004 |
| EP | 1 437 354 B1 | 8/2008 |
| WO | 95/10519 A1 | 4/1995 |
| WO | 99/07696 A1 | 2/1999 |
| WO | 02/48143 A2 | 6/2002 |

OTHER PUBLICATIONS

Li; J. Med. Chem. 1996, 39, 3070-3088.*
Jorgensen; Clinical Infectious Diseases, 2009, 49, 1749-1755.*
Alder et al., "Efficacies of ABT-719 and related 2-pyridones, members of a new class of antibacterial agents, against experimental bacterial infections," Antimicrobial Agents and Chemotherapy 39(4): 971-75 (1995).
Database CA [Online] Chemical Abstracts Service, Columbus, Ohio, US; Fukumoto, Ryoichi et al: "4-Oxoquinolizines, their preparation, and antibacterial agents containing them", XP002672423, retrieved from STN Database acession No. 2002:802427 abstract rns: 472957-91-8, 472957-94-1, 472957-95-2 & JP 2002 308876 A (Sato Pharmaceutical Co., Ltd., Japan) Oct. 23, 2002 & Database.
Fung & Shen "The 2-pyridone antibacterial agents: 8-position modifications," Current Pharmaceutical Design 5(7): 515-43 (1999).
Ma et al., "Synthesis and antimicrobial activity of 4H-4-oxoquinolizine derivatives: Consequences of structural modification at the C-8 position," Journal of Medicinal Chemistry 42(20):4202-13 (1999).
Kuhnz & Gieschen "Predicting the oral bioavailability of 19-nortestosterone progestins in vivo from their metabolic stability in human liver microsomal preparations in vitro," Drug Metabolism and Disposition 26(11):1120-27 (1998).

* cited by examiner

Primary Examiner — John Mabry
Assistant Examiner — Daniel Carcanague
(74) Attorney, Agent, or Firm — McDonnell Boehnen Hulbert & Berghoff LLP

(57) ABSTRACT

Described are a series of 2-pyridone compounds as a potent and selective new class of type II topoisomerase inhibitors with broad-spectrum antimicrobial activity having the general formula (I); where R1, R2, X, and Y are defined herein Such compounds can be used in methods for treating an infection caused by a gram-positive pathogen, a gram-negative pathogen, or a drug-resistant strains thereof.

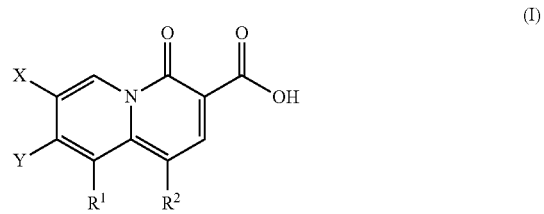

(I)

2 Claims, No Drawings

2-PYRIDONE ANTIMICROBIAL COMPOSITIONS

CROSS-REFERENCE TO RELATED APPLICATIONS

This application is a national stage application under 35 U.S.C. §371 of International Application No. PCT/US2011/052003, filed Sep. 16, 2011, which claims the benefit of U.S. Provisional Application No. 61/386,721, filed Sep. 27, 2010, the disclosures of each of which are explicitly incorporated by reference herein.

FIELD OF INVENTION

The present invention relates to a new 2-pyridone compound series having broad-spectrum antibacterial activity and more particularly, potent activity against fluoroquinolone-resistant bacterial pathogens, particularly against multi-drug resistant community-acquired and nosocomial pathogens.

BACKGROUND OF INVENTION

Drug-resistant bacterial infections and related morbidity and mortality are on the rise around the world. In particular the so-called "ESCAPE" pathogens (*Enterococcus faecium, Staphylococcus aureus, Klebsiella pneumoniae, Acinetobacter baumannii, Pseudomonas aeruginosa* and *Enterobacter* ssp) are the causative agents for the majority of hospital infections and effectively "escape" the effects of approved drugs (Clinical Infectious Diseases 2010; 50: 1081).

Because of world-wide mortality due to uncontrolled severe infections is on the rise, the need for new antimicrobial compounds becomes greater every day. The limited number of targets for antibiotic action, development of multi-drug resistant strains and the ever shrinking number of active drugs have increased the health risks of the human race with respect to the number one killer of all people in the world today, bacterial infection. With the identification of New Delhi metallo-beta-lactamase-1 (NDM1), and highly drug resistant gonorrhoeal strains new antibiotics become more essential on a daily basis.

New classes of antibiotics are being continuously developed, with limited success, in order to expand the armamentarium of treatment options against severe bacterial infections. For instance, second generation quinolones such as Ciprofloxacin are widely accepted for the treatment of bacterial infections of respiratory and urinary tract, skin and soft tissues. Such compounds have good pharmacokinetic profiles, potent activities against a wide range of Gram-positive and Gram-negative pathogens, and are widely used in both hospital and community settings. However, increasing frequency of bacterial resistance to quinolones, among other currently available antibiotics, has led to an urgent need for new analogs to overcome antibiotic resistance.

Bacterial type II topoisomerases are key regulators of the replication, repair and decatenation of DNA in bacteria and are clinically validated targets for antibacterial agents, as demonstrated by the clinical and commercial success of quinolones for the treatment of bacterial infections. Nalidixic acid, introduced in 1962, is considered to be the predecessor of all members of the quinolone family, including the second (e.g. Ciprofloxacin), third (e.g. Levofloxacin) and fourth (e.g. Moxifloxacin) generations commonly known as fluoroquinolones. These molecules form a ternary complex consisting of the inhibitor, topoisomerase and DNA that disrupts DNA replication and repair as well as RNA transcription, a two-punch combination that leads to rapid bacterial cell death. Several compound- and DNA-bound enzyme structures have been solved, paving the way for a greater understanding of both the mechanism for DNA cleavage and the structural basis for inhibition of topoisomerases by antibacterial compounds. Recently, the X-ray crystal structures of the quinolone binding mode have appeared (Bax et al., 2010), generating opportunities for structural optimization and design of topoisomerase inhibitors.

2-Pyridones are a class of antibiotics which inhibit type IIa bacterial topoisomerases and are chemically bioisosteres of quinolones. In 1994, Abbott reported that 2-pyridone analogs were efficacious against certain quinolone resistant microorganisms (34$^{th}$ Interscience Conference on Antimicrobial Agents and Chemotherapy (ICAAC, paper F41), 1994; U.S. Pat. No. 5,789,591), specifically ABT-719, a 4-oxo-quinolizine possessing potent antibacterial activity against both Gram-positive and Gram-negative pathogens. See also Sato U.S. Pat. No. 6,525,066 and U.S. Pat. No. 7,223,773.

The continuing development of natural and engineered resistance to antibiotics in use today necessitates the development of ever new classes of antibiotic compounds which are potent, safe and do not exhibit cross-resistance to existing classes of antibiotics. Furthermore, such compounds would have broad spectrum for empirical first-line treatment, have antibacterial activity via inhibition of bacterial type II topoisomerases, e.g. DNA gyrase (Topo II) and topoisomerase IV (Topo IV), and would preferably be orally bioavailable.

SUMMARY OF THE INVENTION

The present invention provides a novel series of 2-pyridone compounds as a potent and selective new class of type II topoisomerase inhibitors with broad-spectrum antimicrobial activity. The present invention demonstrates for the first time a series of antibiotics having surprising and unexpected potent activity against fluoroquinolone-resistant bacterial pathogens, particularly against multi-drug resistant community-acquired and nosocomial pathogens, suggesting a new mechanism of action against a well-validated bacterial target, the DNA repair and replication system. Members of this compound series have demonstrated broad-spectrum antibacterial activity and favourable drug-like properties.

The series possesses unique biological and physiochemical properties compared to other drugs in the clinic that should allow its use as a first line of defense antibiotic in the current clinical environment, particularly against target organisms such as MRSA and *S. pneumoniae*. Not since the advent of aminoglycosides has a novel broad-spectrum antibiotic entered the clinic for empirical first-line treatment of drug-resistant bacterial infections. The present compounds are likely to serve in such a role in the future treatment of multi-drug resistant infections. The 2-pyridone series of antibiotics of the present invention is very potent (MICs in the ng/mL range) against important nosocomial pathogens, including fluoroquinolone-resistant *Staphylococcus aureus* MRSA.

The compounds of the present invention exhibit broad antibacterial activity via inhibition of bacterial type II topoisomerases, e.g. DNA gyrase (Topo II) and topoisomerase IV (Topo IV), and they are active against many bacterial strains that are resistant to quinolones and other more recently described topoisomerase inhibitors, and provides a potent and selective new class of type II topoisomerase inhibitors with broad-spectrum antimicrobial activity. The present compounds also exhibit potent inhibition of *Escherichia coli* DNA gyrase supercoiling with IC$_{50}$≤0.1 µM Furthermore, the inventive compounds were found to be bactericidal, stable (chemical, metabolic, plasma) with manageable protein binding data. Mammalian cytotoxicity was shown to be >100 µM. Aqueous thermodynamic solubility ranges from, for example, 5 to 200 µM in PBS and SGF, but very importantly is >100 μM in SIF hence contributing to the excellent absorption displayed by the compounds. In particular, the potassium salts of the various compounds herein have been found to have unexpectedly increased solubility in PBS, SGF, and/or SIF. These positive data allowed a selection of compounds to progress to PK studies in preparation of the efficacy studies.

The inventive compounds are also very potent against *Staphylococcus aureus*, including MRSA, *Streptococcus pneumoniae* and pyogenes, *Enterococcus faecium* and faecalis with MICs<0.5 mg/L. Most compounds are also very potent against *Haemophilus influenzae*, *Moraxella* and Enterobacteriacae such as *Klebsiella*, *Proteus*, *Shigella* and others with MICs ranging between <0.015 to 16 mg/L. Better coverage is seen against *Pseudomonas aeruginosa*, *Burkholderia cepacia*, *Acinetobacter baumannii* and *Escherichia coli* than levofloxacin.

In addition, the inventive compounds are active against multidrug-resistant recent clinical isolates of the bacteria mentioned above. In particular, many of the compounds show activity against resistant strains, such as, but not limited to quinolone-resistant strains (e.g., *Staphylococcus aureus*, *Pseudomonas aeruginosa* and *Acinetobacter baumanii*). No loss of activity is seen on *Staphylococcus aureus* strains with mutations in gyrB, GrlA and GrlB and show a low propensity of spontaneous resistance development.

Finally, the inventive compounds have advantageous physicochemical characteristics. Excellent aqueous kinetic solubility could be achieved (≥10 mg/mL) with formation of potassium salt in place of the parent carboxylic acid. Overall, the compounds described herein may be prepared by efficient and scalable syntheses of less than 10 steps.

In a first aspect, the invention provides methods for treating an infection comprising, providing to a patient infected by a gram-positive pathogen or gram-negative pathogen, such as a pathogen selected from the group consisting of *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter sp, Enterobacter cloacae, Enterococcus faecalis, Enterococcus faecium, Enterococcus gallinarum, Escherichia coli, Francisella tularensis, Haemophilus influenza, Klebsiella aerogenes, Klebsiella pneumoniae, Listeria monocytogenes, Moraxella catarrhalis, Morganella morganii, Neisseria meningitides, Proteus mirabilis, Providencia stuartii, Pseudomonas aeruginosa, Serratia marcescens, Shigella sp, Staphylococcus aureus, Staphylococcus epidermis, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pneumoniae, Streptococcus pyogenes, Streptococcus oralis, Streptococcus sanguis*, Group C *Streptococcus, Yersinia pestis*, and drug-resistant strains thereof, a therapeutically effective amount of a compound of the formula,

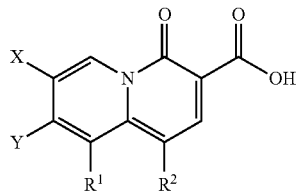

(I)

wherein $R^1$, $R^2$, X, and Y are defined herein.

In another aspect, the invention provides the use of a compound of the formula (I), as defined herein for the preparation of a medicament for treating an infection caused by a gram-positive pathogen or gram-negative pathogen, such as a pathogen selected from the group consisting of *Burkholderia mallei, Burkholderia pseudomallei, Burkholderia cepacia, Bacillus anthracis, Yersinia pestis, Francisella tularensis, Brucella abortus, Burkholderia thailandensis, Acinetobacter baumannii, Acinetobacter baumannii, Staphylococcus aureus, Staphylococcus epidermis, Enterococcus faecalis, Enterococcus faecium, Escherichia coli, Enterobacter cloacae, Pseudomonas aeruginosa, Klebsiella pneumoniae, Haemophilus influenza, Stenotrophomonas maltophilia, Streptococcus pneumoniae, Streptococcus pyogenes*, Group C *Streptococcus*, and drug-resistant strains thereof.

In another aspect of the invention is provided a pharmaceutical composition comprising a 2-pyridone of formula (I) for prophylaxis or treatment of an infection induced by a pathogen in a subject that may be exposed to or is suffering from an infection, the composition conferring prophylaxis, reduction in contagion, treatment, amelioration or reduction of symptoms, reduction of mortality or survival in the subject after administration of the composition.

The invention provides a useful 2-pyridone scaffold, structurally related but distinct to quinolones. It is hypothesised by the inventors that (a) 2-pyridones maintain activity on quinolone resistant strains because of the non-planar nature of the scaffold (vs. quinolones) induced by combinations of certain substituents; and (b) there are specific binding site residues and DNA structural elements which may be utilised to further enhance activity on quinolone resistant strains.

In silico approaches have identified key structure guided hypotheses. 2-Pyridones maintain activity on quinolone-resistant strains because of the non-planar nature of the scaffold (as compared with quinolones) induced by combinations of certain substituents. Various substituents at the 9-position have been designed which optimise the 'wedge-like' effect of the compound to enhance its interaction with the binding site. There are specific binding site residues and DNA structural elements which may be utilised to further enhance activity on quinolone resistant strains. In silico design has been used to identify optimal receptor interactions from the 1- and 8-positions which may enhance compound binding to the ribose backbone and specific amino acids improving activity in the presence of known resistance mutations.

Therefore, the present invention provides for 2-pyridone compounds with differing substituents at the 9-position designed to optimise the 'wedge-like' effect of the compound to enhance its interaction with the binding site.

DESCRIPTION OF THE INVENTION

Accordingly, in the first aspect, infections caused by a pathogen selected from the group consisting of *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter sp, Enterobacter cloacae, Enterococcus faecalis, Enterococcus faecium, Enterococcus gallinarum, Escherichia coli, Francisella tularensis, Haemophilus influenza, Klebsiella aerogenes, Klebsiella pneumoniae, Listeria monocytogenes, Moraxella catarrhalis, Morganella morganii, Neisseria meningitides, Proteus mirabilis, Providencia stuartii, Pseudomonas aeruginosa, Serratia marcescens, Shigella sp, Staphylococcus aureus, Staphylococcus epidermis, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pneumoniae, Streptococcus pyogenes, Strep-* tococcus oralis, Streptococcus sanguis, Group C *Streptococcus*, *Yersinia pestis*, and drug-resistant strains thereof, can be treated by providing to a patient a therapeutically effective amount of a compound of the formula,

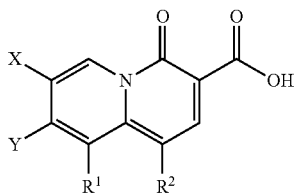

(I)

or a pharmaceutically acceptable salt thereof, wherein
$R^1$ is hydrogen, halogen, cyano, $C_{1-8}$ alkyl, $C_{1-8}$ haloalkyl, heterocyclyl, —$OR^{11}$, —$N(R^{11})_2$, or —$C(O)N(R^{11})_2$, wherein each $R^{11}$ is independently hydrogen, $C_{1-8}$ alkyl, or $C_{1-8}$ haloalkyl;
$R^2$ is a $C_{1-8}$ alkyl, $C_{1-8}$ haloalkyl, $C_{3-8}$cycloalkyl, or heteroaryl, wherein the cycloalkyl and heteroaryl are optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl;
Y is heterocyclyl, aryl, or heteroaryl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$, wherein $R^Y$ is nitro, cyano, —$OR^{Y1}$, —$SR^{Y1}$, —$N(R^{Y1})_2$, —$C(O)R^{Y1}$, —$C(O)OR^{Y1}$, —$C(O)N(R^{Y1})_2$, —$OC(O)R^{Y1}$, —$OC(O)OR^{Y1}$, —$OC(O)N(R^{Y1})_2$, —$N(R^{Y1})C(O)R^{Y1}$, —$N(R^{Y1})C(O)OR^{Y1}$, —$N(R^{Y1})C(O)N(R^{Y1})_2$, —$S(O)_2R^{Y1}$, —$S(O)_2OR^{Y1}$, —$S(O)_2N(R^{Y1})_2$, —$OS(O)_2R^{Y1}$, —$OS(O)_2OR^{Y1}$, —$OS(O)_2N(R^{Y1})_2$, —$N(R^{Y1})S(O)_2R^{Y1}$, —$N(R^{Y1})S(O)_2OR^{Y1}$, or —$N(R^{Y1})S(O)_2N(R^{Y1})_2$, wherein each $R^{Y1}$ is independently hydrogen, $C_{1-8}$ alkyl, or $C_{1-8}$ haloalkyl; and
X is hydrogen, halogen, cyano, $C_{1-8}$ alkyl, $C_{1-8}$haloalkyl, —$OR^X$, —$N(R^X)_2$, —$C(O)R^X$, —$C(O)OR^X$, or —$C(O)N(R^X)_2$, wherein each $R^X$ is independently hydrogen, $C_{1-8}$ alkyl, or $C_{1-8}$haloalkyl.

In one embodiment of the compounds of formula (I), $R^1$ is hydrogen, halogen, or $C_{1-8}$ alkyl. In another embodiment, $R^1$ is hydrogen or $C_{1-8}$ alkyl. In another embodiment, $R^1$ is hydrogen or methyl. In another embodiment, $R^1$ is halogen or $C_{1-8}$ alkyl. In another embodiment, $R^1$ is $C_{1-8}$ alkyl. In another embodiment, $R^1$ is halogen. In another embodiment of the compounds of formula (I), $R^1$ is $C_{1-8}$ haloalkyl, —$OR^{11}$, or —$C(O)N(R^{11})_2$. In another embodiment of the compounds of formula (I), $R^1$ is trifluoromethyl, methoxy, or —$C(O)NH_2$. In certain embodiments, the compound for formula (I) is of one of the formulas,

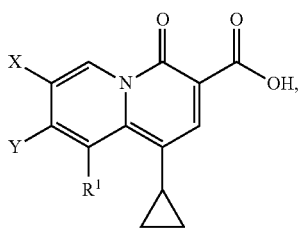

(Ia)

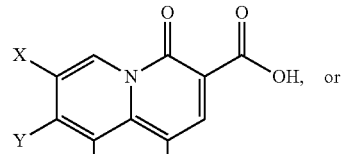

(Ib)

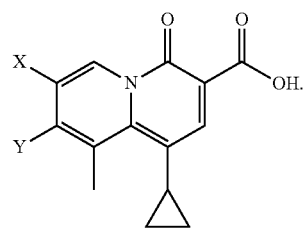

(Ic)

In one embodiment of the compounds of formula (I), (Ia)-(Ic), and any embodiment thereof, X is hydrogen or halogen. In another embodiment, X is hydrogen. In another embodiment, X is halogen. In another embodiment, X is fluoro. In another embodiment, X is hydrogen, halogen, $C_{1-8}$ alkyl, $C_{1-8}$ alkoxy, amino, $C_{1-8}$ alkylamino, or di($C_{1-8}$ alkyl)amino. In another embodiment, X is —$OR^X$, —$N(R^X)_2$, —$C(O)R^X$, —$C(O)OR^X$, or —$C(O)N(R^X)_2$. In another embodiment, X is —$OR^X$ or —$N(R^X)_2$. In another embodiment, X is —$C(O)R^X$, —$C(O)OR^X$, or —$C(O)N(R^X)_2$. In another embodiment, X is $C_{1-8}$haloalkyl (e.g., trifluoromethyl).

In particular embodiments of the compounds of formula (I) and (Ia), $R^1$ and X are selected from one of the following combinations:
(a) $R^1$ is hydrogen, halogen, or $C_{1-8}$ alkyl; and X is hydrogen or halogen.
(b) $R^1$ is hydrogen, halogen, or $C_{1-8}$ alkyl; and X is hydrogen.
(c) $R^1$ is hydrogen, halogen, or $C_{1-8}$ alkyl; and X is halogen.
(d) $R^1$ is hydrogen, halogen, or $C_{1-8}$ alkyl; and X is fluoro.
(e) $R^1$ is hydrogen or $C_{1-8}$ alkyl; and X is hydrogen or halogen.
(f) $R^1$ is hydrogen or $C_{1-8}$ alkyl; and X is hydrogen.
(g) $R^1$ is hydrogen or $C_{1-8}$ alkyl; and X is halogen.
(h) $R^1$ is hydrogen or $C_{1-8}$ alkyl; and X is fluoro.
(i) $R^1$ is hydrogen or methyl; and X is hydrogen or halogen.
(j) $R^1$ is hydrogen or methyl; and X is hydrogen.
(k) $R^1$ is hydrogen or methyl; and X is halogen.
(l) $R^1$ is hydrogen or methyl; and X is fluoro.
(m) $R^1$ is halogen or $C_{1-8}$ alkyl; and X is hydrogen or halogen.
(n) $R^1$ is halogen or $C_{1-8}$ alkyl; and X is hydrogen.
(o) $R^1$ is halogen or $C_{1-8}$ alkyl; and X is halogen.
(p) $R^1$ is halogen or $C_{1-8}$ alkyl; and X is fluoro.
(q) $R^1$ is $C_{1-8}$ alkyl; and X is hydrogen or halogen.
(r) $R^1$ is $C_{1-8}$ alkyl; and X is hydrogen.
(s) $R^1$ is $C_{1-8}$ alkyl; and X is halogen.
(t) $R^1$ is $C_{1-8}$ alkyl; and X is fluoro.

In one embodiment of the compounds of formula (I), (Ia)-(Ic), and any embodiment thereof, Y is aryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is halogen, cyano, —$OR^{Y1}$, —$SR^{Y1}$, —$N(R^{Y1})_2$, $C_{1-8}$ alkyl, —$C_{1-8}$ alkyl-$N(R^{Y1})_2$, or —$C_{1-8}$ alkyl- $OR^{Y1}$, and optionally substituted by one to two groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl $(C_{1-8})$ alkyl, heterocyclyl$(C_{1-8})$alkyl, aryl$(C_{1-8})$alkyl, heteroaryl$(C_{1-8})$alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is cyano, —$OR^{Y1}$, —$N(R^{Y1})_2$, $C_{1-8}$ alkyl, or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is —$N(R^{Y1})_2$ or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is —$NH_2$ or —$C_{1-8}$ alkyl-$NH_2$, and optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is —$NH_2$ or —$CH_2NH_2$, and optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is phenyl substituted with one group which is —$NH_2$ or —$CH_2NH_2$, and substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$ alkyl, —$R^Y$, or —$C_{1-8}$ alkyl-$R^Y$.

In another embodiment of the compounds of formula (I), (Ia)-(Ic), and any embodiment thereof, Y is a 5-membered or 6-membered heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$alkyl, —$R^Y$, or —$C_{1-8}$ alkyl-$R^Y$.

In another embodiment of the compounds of formula (I), (Ia)-(Ic), and any embodiment thereof, Y is a 5-membered or 6-membered heteroaryl substituted with one group which is —$N(R^{Y1})_2$ or —$C_{1-8}$ alkyl-$N(R^{Y1})_2$, and optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is pyridyl, furyl, or thienyl each optionally substituted with one group which is —$N(R^{Y1})_2$ or —$C_{1-8}$ alkyl-$N(R^{Y1})_2$, and each optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is pyridyl, furyl, or thienyl each optionally substituted with one group which is —$NH_2$ or —$CH_2NH_2$, and each optionally substituted by one to two groups that are each independently halogen, $C_{1-8}$ alkyl, —$R^Y$, or —$C_{1-8}$ alkyl-$R^Y$.

In another embodiment of the compounds of formula (I), (Ia)-(Ic), and any embodiment thereof, Y is a bicyclic heteroaryl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$alkyl, —$R^Y$, or —$C_{1-8}$ alkyl-$R^Y$.

In another embodiment of the compounds of formula (I), (Ia)-(Ic), and any embodiment thereof, Y is a benzofuranyl, benzothienyl, indolyl, indazolyl, benzimidazolyl, benzoxazolyl, benzoisoxazolyl, benzothiazolyl, benzoisothiazolyl, or benzotriazolyl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$alkyl, —$R^Y$, or —$C_{1-8}$ alkyl-$R^Y$.

In another embodiment of the compounds of formula (I), (Ia)-(Ic), and any embodiment thereof, Y is indazolyl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl$(C_{1-8})$ alkyl, heterocyclyl$(C_{1-8})$alkyl, aryl$(C_{1-8})$alkyl, heteroaryl$(C_{1-8})$ alkyl, —$R^Y$, or —$C_{1-8}$ alkyl-$R^Y$.

In another embodiment of the compounds of formula (I), (Ia)-(Ic), and any embodiment thereof, Y is indazolyl.

In one embodiment of the compounds of formula (I) and (Ib), and any embodiment thereof, $R^2$ is a $C_{1-8}$ alkyl, $C_{1-8}$ haloalkyl, or $C_{3-8}$cycloalkyl.

In one embodiment of the compounds of formula (I) and (Ib), and any embodiment thereof, $R^2$ is a $C_{1-8}$ alkyl (e.g., methyl).

In one embodiment of the compounds of formula (I) and (Ib), and any embodiment thereof, $R^2$ is a $C_{1-8}$ haloalkyl (e.g., trifluoromethyl).

In one embodiment of the compounds of formula (I) and (Ib), and any embodiment thereof, $R^2$ is $C_{3-8}$cycloalkyl (e.g., cyclopropyl, cyclobutyl, cyclopentyl, or cyclohexyl).

In one embodiment of the compounds of formula (I) and (Ib), and any embodiment thereof, $R^2$ is $C_{3-8}$cycloalkyl optionally substituted by one or two groups that are each independently halogen or $C_{1-8}$ alkyl (e.g., fluoro or methyl).

In another embodiment of the compounds of formula (I) and (Ib), and any embodiment thereof, $R^2$ is heteroaryl, wherein the heteroaryl is optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl.

In certain embodiments, the compound for use in the preceding method is selected from the group consisting of,

| Compounds | Structure | Name |
|---|---|---|
| Example 1 | 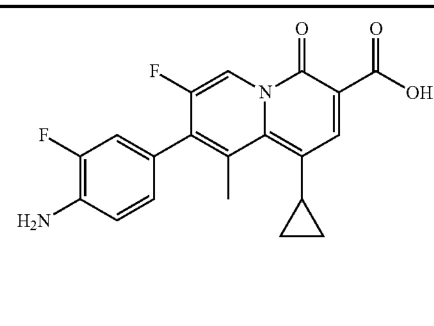 | 8-(3-fluoro-4-amino-phenyl)-1-cyclopropyl-7-fluoro-9-methyl-4-oxo-quinolizine-3-carboxylic acid |

-continued

| Compounds | Structure | Name |
|---|---|---|
| Example 2 | 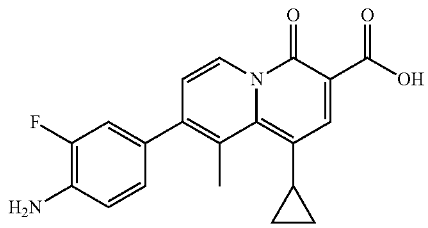 | 8-(3-fluoro-4-amino-phenyl)-1-cyclopropyl-9-methyl-4-oxo-quinolizine-3-carboxylic acid |
| Example 3 | 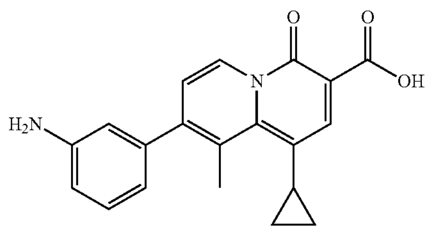 [SMILES: Cc1c(-c2cccc(N)c2)ccn2c(=O)c(C(=O)O)cc(C3CC3)c12] | 8-(3-amino-phenyl)-1-cyclopropyl-9-methyl-4-oxo-quinolizine-3-carboxylic acid |
| Example 4 | 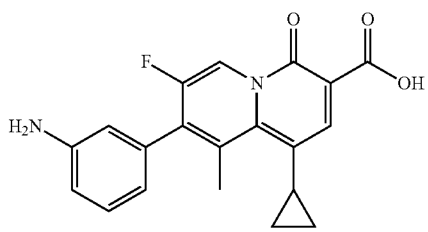 [SMILES: Cc1c(-c2cccc(N)c2)c(F)cn2c(=O)c(C(=O)O)cc(C3CC3)c12] | 8-(3-amino-phenyl)-1-cyclopropyl-7-fluoro-9-methyl-4-oxo-quinolizine-3-carboxylic acid |
| Example 5 | 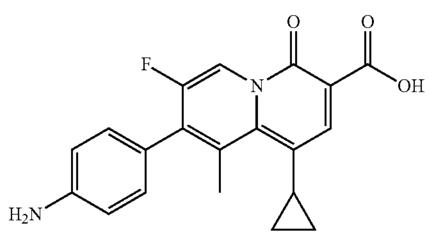 [SMILES: Cc1c(-c2ccc(N)cc2)c(F)cn2c(=O)c(C(=O)O)cc(C3CC3)c12] | 8-(4-amino-phenyl)-1-cyclopropyl-7-fluoro-9-methyl-4-oxo-quinolizine-3-carboxylic acid |
| Example 6 | 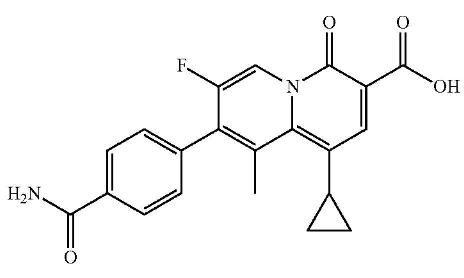 [SMILES: Cc1c(-c2ccc(C(N)=O)cc2)c(F)cn2c(=O)c(C(=O)O)cc(C3CC3)c12] | 8-(4-carbamoyl-phenyl)-1-cyclopropyl-7-fluoro-9-methyl-4-oxo-quinolizine-3-carboxylic acid |
| Example 7 | 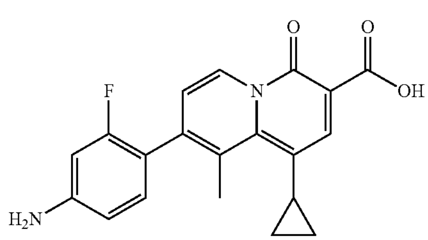 [SMILES: Cc1c(-c2ccc(N)cc2F)ccn2c(=O)c(C(=O)O)cc(C3CC3)c12] | 8-(2-fluoro-4-amino-phenyl)-1-cyclopropyl-9-methyl-4-oxo-quinolizine-3-carboxylic acid |

| Compounds | Structure | Name |
|---|---|---|
| Example 8 | 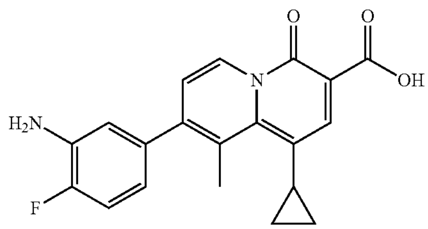 [SMILES: Cc1c(-c2ccc(F)c(N)c2)ccn2c(=O)c(C(=O)O)cc(C3CC3)c12] | 8-(3-amino-4-fluoro-phenyl)-1-cyclopropyl-9-methyl-4-oxo-quinolizine-3-carboxylic acid |
| Example 9 | 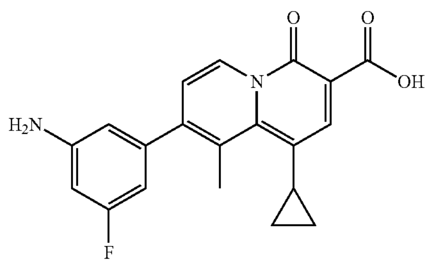 [SMILES: Cc1c(-c2cc(N)cc(F)c2)ccn2c(=O)c(C(=O)O)cc(C3CC3)c12] | 8-(3-amino-5-fluoro-phenyl)-1-cyclopropyl-9-methyl-4-oxo-quinolizine-3-carboxylic acid |
| Example 10 | 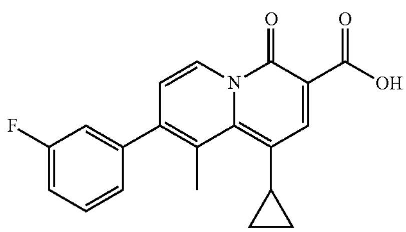 [SMILES: Cc1c(-c2cccc(F)c2)ccn2c(=O)c(C(=O)O)cc(C3CC3)c12] | 8-(3-fluoro-phenyl)-1-cyclopropyl-9-methyl-4-oxo-quinolizine-3-carboxylic acid |
| Example 11 | 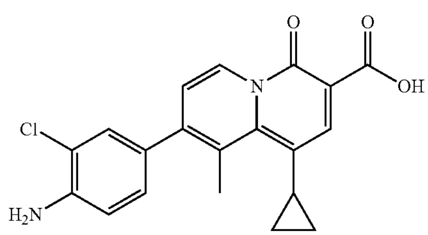 [SMILES: Cc1c(-c2ccc(N)c(Cl)c2)ccn2c(=O)c(C(=O)O)cc(C3CC3)c12] | 8-(3-chloro-4-amino-phenyl)-1-cyclopropyl-9-methyl-4-oxo-quinolizine-3-carboxylic acid |
| Example 12 | 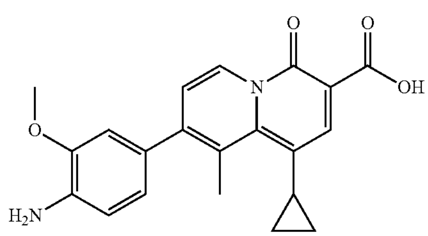 [SMILES: COc1cc(-c2ccn3c(=O)c(C(=O)O)cc(C4CC4)c3c2C)ccc1N] | 8-(3-methoxy-4-amino-phenyl)-1-cyclopropyl-9-methyl-4-oxo-quinolizine-3-carboxylic acid |
| Example 13 | 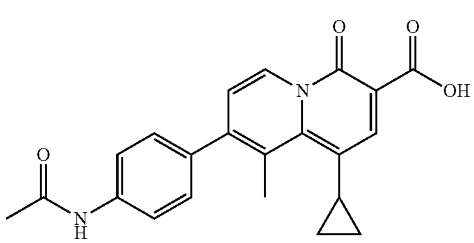 [SMILES: CC(=O)Nc1ccc(-c2ccn3c(=O)c(C(=O)O)cc(C4CC4)c3c2C)cc1] | 8-(4-acetamido-phenyl)-1-cyclopropyl-9-methyl-4-oxo-quinolizine-3-carboxylic acid |

-continued

| Compounds | Structure | Name |
|---|---|---|
| Example 14 | 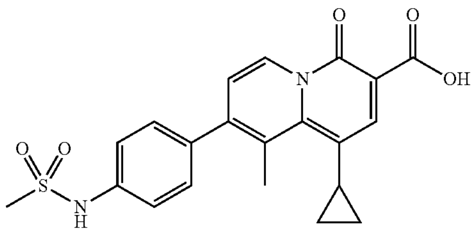 [SMILES: Cc1c(-c2ccc(NS(C)(=O)=O)cc2)ccn2c(=O)c(C(=O)O)cc(C3CC3)c12] | 8-(4-sulfonamido-phenyl)-1-cyclopropyl-9-methyl-4-oxo-quinolizine-3-carboxylic acid |
| Example 15 | 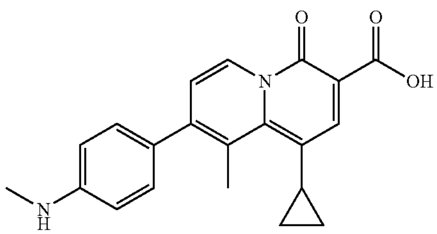 [SMILES: CNc1ccc(-c2ccn3c(=O)c(C(=O)O)cc(C4CC4)c3c2C)cc1] | 8-(4-methylamino-phenyl)-1-cyclopropyl-9-methyl-4-oxo-quinolizine-3-carboxylic acid |
| Example 16 | 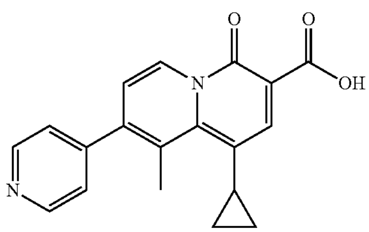 [SMILES: Cc1c(-c2ccncc2)ccn2c(=O)c(C(=O)O)cc(C3CC3)c12] | 8-(4-pyridyl)-1-cyclopropyl-9-methyl-4-oxo-quinolizine-3-carboxylic acid |
| Example 17 | 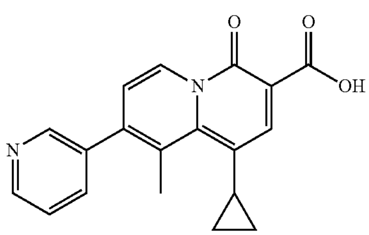 [SMILES: Cc1c(-c2cccnc2)ccn2c(=O)c(C(=O)O)cc(C3CC3)c12] | 8-(3-pyridyl)-1-cyclopropyl-9-methyl-4-oxo-quinolizine-3-carboxylic acid |
| Example 18 | 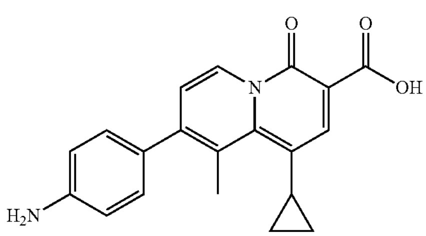 [SMILES: Cc1c(-c2ccc(N)cc2)ccn2c(=O)c(C(=O)O)cc(C3CC3)c12] | 8-(4-amino-phenyl)-1-cyclopropyl-9-methyl-4-oxo-quinolizine-3-carboxylic acid |
| Example 19 | 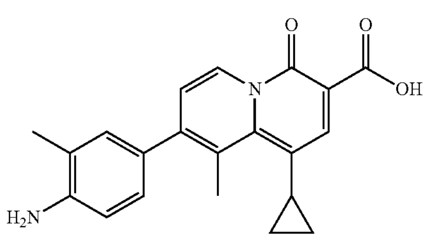 [SMILES: Cc1cc(-c2ccn3c(=O)c(C(=O)O)cc(C4CC4)c3c2C)ccc1N] | 8-(3-methyl-4-amino-phenyl)-1-cyclopropyl-9-methyl-4-oxo-quinolizine-3-carboxylic acid |

-continued

| Compounds | Structure | Name |
| --- | --- | --- |
| Example 20 | 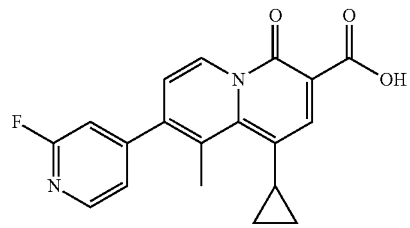 [SMILES: Cc1c(-c2ccnc(F)c2)ccn2c(=O)c(C(=O)O)cc(C3CC3)c12] | 8-(2-fluoro-4-pyridyl)-1-cyclopropyl-9-methyl-4-oxo-quinolizine-3-carboxylic acid |
| Example 21 | 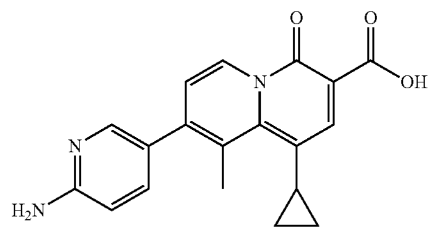 [SMILES: Cc1c(-c2ccc(N)nc2)ccn2c(=O)c(C(=O)O)cc(C3CC3)c12] | 8-(6-amino-3-pyridyl)-1-cyclopropyl-9-methyl-4-oxo-quinolizine-3-carboxylic acid |
| Example 22 | 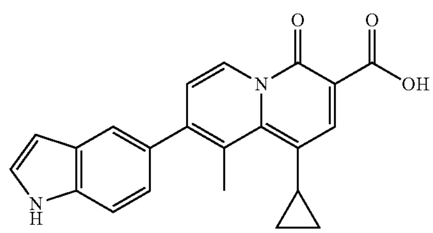 [SMILES: Cc1c(-c2ccc3[nH]ccc3c2)ccn2c(=O)c(C(=O)O)cc(C3CC3)c12] | 8-(1H-indol-5-yl)-1-cyclopropyl-9-methyl-4-oxo-quinolizine-3-carboxylic acid |
| Example 23 | 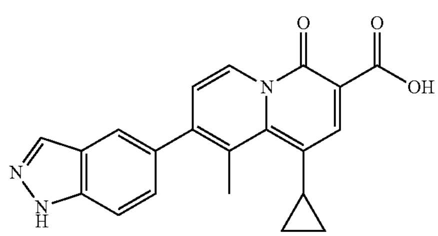 [SMILES: Cc1c(-c2ccc3[nH]ncc3c2)ccn2c(=O)c(C(=O)O)cc(C3CC3)c12] | 8-(1H-indazol-5-yl)-1-cyclopropyl-9-methyl-4-oxo-quinolizine-3-carboxylic acid |
| Example 24 | 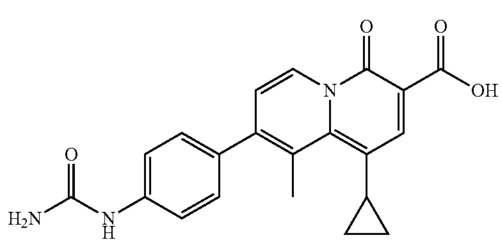 [SMILES: Cc1c(-c2ccc(NC(N)=O)cc2)ccn2c(=O)c(C(=O)O)cc(C3CC3)c12] | 8-(4-ureido-phenyl)-1-cyclopropyl-9-methyl-4-oxo-quinolizine-3-carboxylic acid |
| Example 25 | 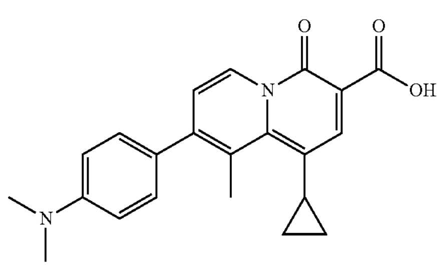 [SMILES: Cc1c(-c2ccc(N(C)C)cc2)ccn2c(=O)c(C(=O)O)cc(C3CC3)c12] | 8-(4-dimethylamino-phenyl)-1-cyclopropyl-9-methyl-4-oxo-quinolizine-3-carboxylic acid |

| Compounds | Structure | Name |
|---|---|---|
| Example 26 | 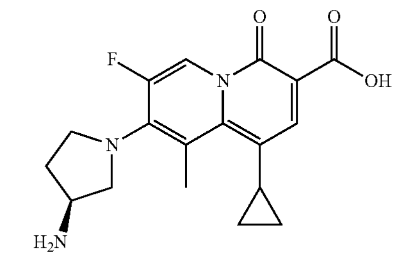 [SMILES: Cc1c(N2CC[C@H](N)C2)c(F)cn2c(=O)c(C(=O)O)cc(C3CC3)c12] | 8-[(3S)-3-aminopyrrolidin-1-yl]-1-cyclopropyl-7-fluoro-9-methyl-4-oxo-quinolizine-3-carboxylic acid |
| Example 27 | 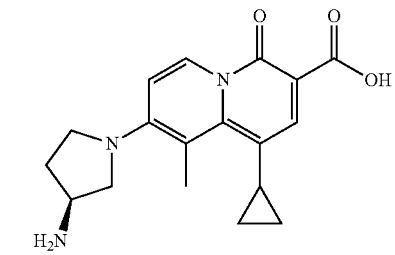 [SMILES: Cc1c(N2CC[C@H](N)C2)ccn2c(=O)c(C(=O)O)cc(C3CC3)c12] | 8-[(3S)-3-aminopyrrolidin-1-yl]-1-cyclopropyl-9-methyl-4-oxo-quinolizine-3-carboxylic acid |
| Example 28 | 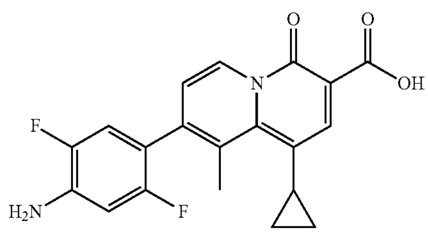 [SMILES: Cc1c(-c2cc(F)c(N)cc2F)ccn2c(=O)c(C(=O)O)cc(C3CC3)c12] | 8-(3,6-difluoro-4-amino-phenyl)-1-cyclopropyl-9-methyl-4-oxo-quinolizine-3-carboxylic acid |
| Example 29 | 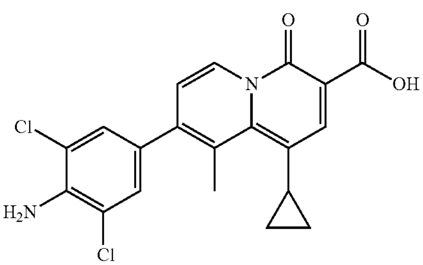 [SMILES: Cc1c(-c2cc(Cl)c(N)c(Cl)c2)ccn2c(=O)c(C(=O)O)cc(C3CC3)c12] | 8-(3,5-dichloro-4-amino-phenyl)-1-cyclopropyl-9-methyl-4-oxo-quinolizine-3-carboxylic acid |
| Example 30 | 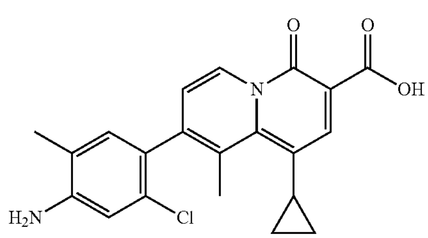 [SMILES: Cc1cc(-c2ccn3c(=O)c(C(=O)O)cc(C4CC4)c3c2C)c(Cl)cc1N] | 8-(2-chloro-4-amino-5-methyl-phenyl)-1-cyclopropyl-9-methyl-4-oxo-quinolizine-3-carboxylic acid |
| Example 31 | 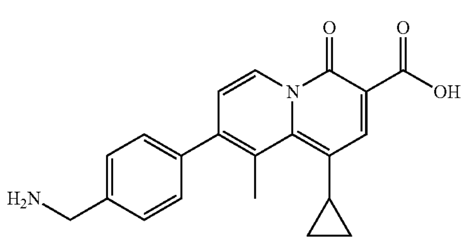 [SMILES: Cc1c(-c2ccc(CN)cc2)ccn2c(=O)c(C(=O)O)cc(C3CC3)c12] | 8-(4-aminomethyl-phenyl)-1-cyclopropyl-9-methyl-4-oxo-quinolizine-3-carboxylic acid |

-continued

| Compounds | Structure | Name |
|---|---|---|
| Example 32 | 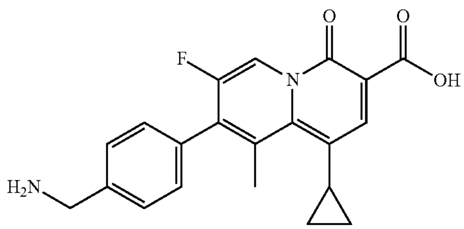 [SMILES: Cc1c(-c2ccc(CN)cc2)c(F)cn2c(=O)c(C(=O)O)cc(C3CC3)c12] | 8-(4-aminomethyl-phenyl)-1-cyclopropyl-7-fluoro-9-methyl-4-oxo-quinolizine-3-carboxylic acid |
| Example 33 | 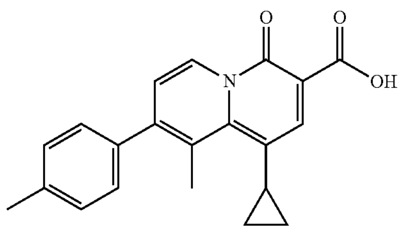 [SMILES: Cc1ccc(-c2ccn3c(=O)c(C(=O)O)cc(C4CC4)c3c2C)cc1] | 8-(4-toluyl)-1-cyclopropyl-9-methyl-4-oxo-quinolizine-3-carboxylic acid |
| Example 34 | 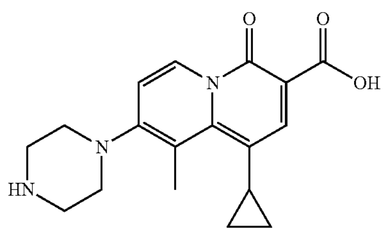 [SMILES: Cc1c(N2CCNCC2)ccn2c(=O)c(C(=O)O)cc(C3CC3)c12] | 8-(piperazin-1-yl)-1-cyclopropyl-9-methyl-4-oxo-quinolizine-3-carboxylic acid |
| Example 35 | 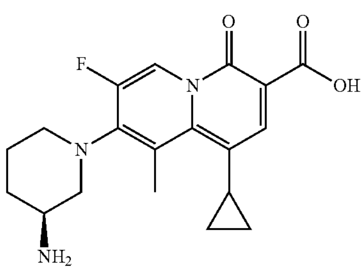 [SMILES: Cc1c(N2CCC[C@H](N)C2)c(F)cn2c(=O)c(C(=O)O)cc(C3CC3)c12] | 8-[(3S)-3-amino-1-piperidyl]-1-cyclopropyl-9-methyl-4-oxo-quinolizine-3-carboxylic acid |
| Example 36 | 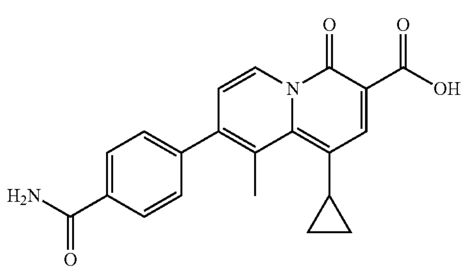 [SMILES: Cc1c(-c2ccc(C(N)=O)cc2)ccn2c(=O)c(C(=O)O)cc(C3CC3)c12] | 8-(4-carbamoyl-phenyl)-1-cyclopropyl-9-methyl-4-oxo-quinolizine-3-carboxylic acid |
| Example 37 | 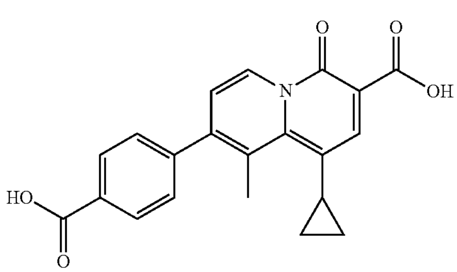 [SMILES: Cc1c(-c2ccc(C(=O)O)cc2)ccn2c(=O)c(C(=O)O)cc(C3CC3)c12] | 8-(4-carboxy-phenyl)-1-cyclopropyl-9-methyl-4-oxo-quinolizine-3-carboxylic acid |

| Compounds | Structure | Name |
|---|---|---|
| Example 38 | 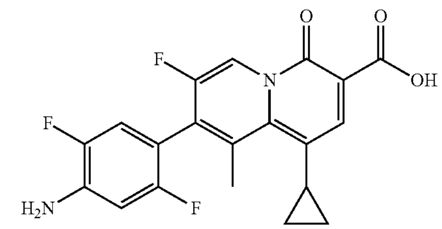 [SMILES: Cc1c(-c2cc(F)c(N)cc2F)c(F)cn2c(=O)c(C(=O)O)cc(C3CC3)c12] | 8-(2,5-difluoro-4-amino-phenyl)-1-cyclopropyl-7-fluoro-9-methyl-4-oxo-quinolizine-3-carboxylic acid |
| Example 39 | 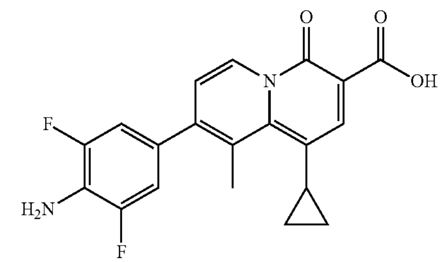 [SMILES: Cc1c(-c2cc(F)c(N)c(F)c2)ccn2c(=O)c(C(=O)O)cc(C3CC3)c12] | 8-(3,5-difluoro-4-amino-phenyl)-1-cyclopropyl-9-methyl-4-oxo-quinolizine-3-carboxylic acid |
| Example 40 | 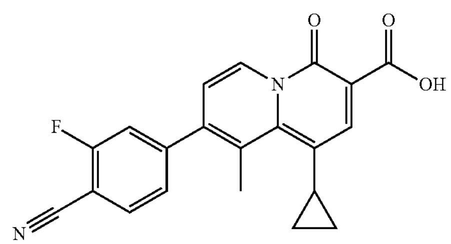 [SMILES: Cc1c(-c2ccc(C#N)c(F)c2)ccn2c(=O)c(C(=O)O)cc(C3CC3)c12] | 8-(3-fluoro-4-cyano-phenyl)-1-cyclopropyl-9-methyl-4-oxo-quinolizine-3-carboxylic acid |
| Example 41 | 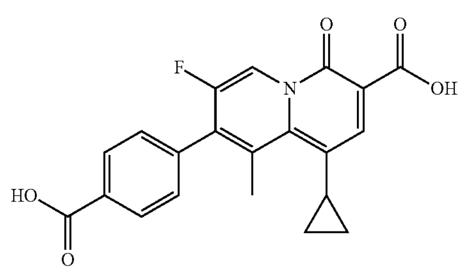 [SMILES: Cc1c(-c2ccc(C(=O)O)cc2)c(F)cn2c(=O)c(C(=O)O)cc(C3CC3)c12] | 8-(4-carboxy-phenyl)-1-cyclopropyl-7-fluoro-9-methyl-4-oxo-quinolizine-3-carboxylic acid |
| Example 42 | 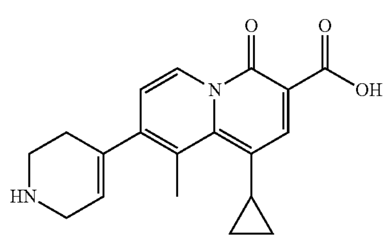 [SMILES: Cc1c(C2=CCNCC2)ccn2c(=O)c(C(=O)O)cc(C3CC3)c12] | 8-(1,2,3,6-tetrahydro-pyridin-4-yl)-1-cyclopropyl-9-methyl-4-oxo-quinolizine-3-carboxylic acid |
| Example 43 | 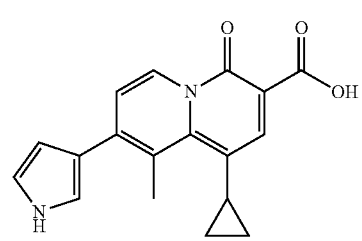 [SMILES: Cc1c(-c2cc[nH]c2)ccn2c(=O)c(C(=O)O)cc(C3CC3)c12] | 8-(1H-pyrrol-3-yl)-1-cyclopropyl-9-methyl-4-oxo-quinolizine-3-carboxylic acid |

-continued

| Compounds | Structure | Name |
|---|---|---|
| Example 44 | 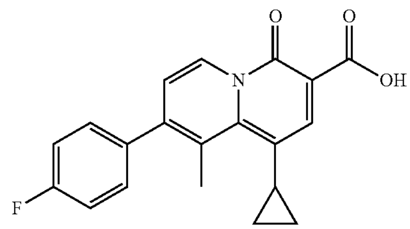 [SMILES: Cc1c(-c2ccc(F)cc2)ccn2c(=O)c(C(=O)O)cc(C3CC3)c12] | 8-(4-fluoro-phenyl)-1-cyclopropyl-9-methyl-4-oxo-quinolizine-3-carboxylic acid |
| Example 45 | 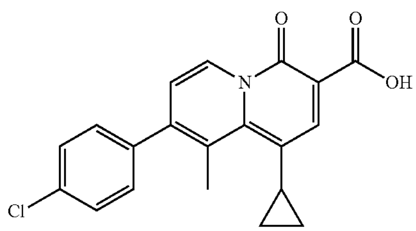 [SMILES: Cc1c(-c2ccc(Cl)cc2)ccn2c(=O)c(C(=O)O)cc(C3CC3)c12] | 8-(4-chloro-phenyl)-1-cyclopropyl-9-methyl-4-oxo-quinolizine-3-carboxylic acid |
| Example 46 | 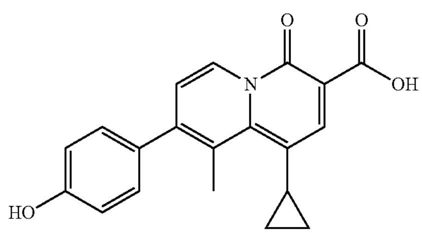 [SMILES: Cc1c(-c2ccc(O)cc2)ccn2c(=O)c(C(=O)O)cc(C3CC3)c12] | 8-(4-hydroxy-phenyl)-1-cyclopropyl-9-methyl-4-oxo-quinolizine-3-carboxylic acid |
| Example 47 | 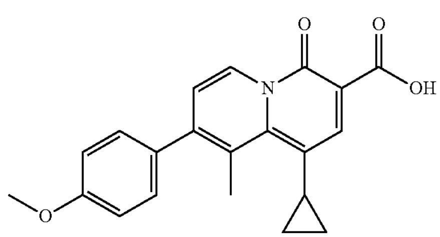 [SMILES: COc1ccc(-c2ccn3c(=O)c(C(=O)O)cc(C4CC4)c3c2C)cc1] | 8-(4-methoxy-phenyl)-1-cyclopropyl-9-methyl-4-oxo-quinolizine-3-carboxylic acid |
| Example 48 | 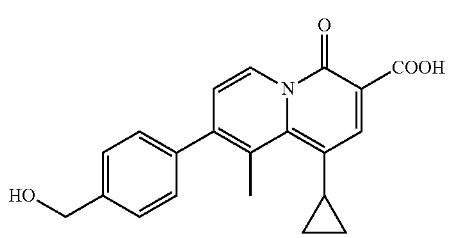 [SMILES: Cc1c(-c2ccc(CO)cc2)ccn2c(=O)c(C(=O)O)cc(C3CC3)c12] | 8-(4-hydroxymethyl-phenyl)-1-cyclopropyl-9-methyl-4-oxo-quinolizine-3-carboxylic acid |
| Example 49 | 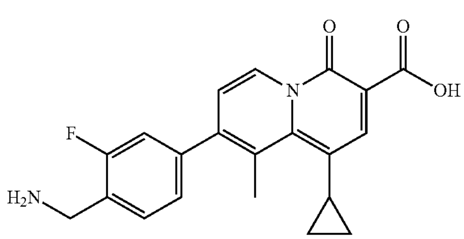 [SMILES: Cc1c(-c2ccc(CN)c(F)c2)ccn2c(=O)c(C(=O)O)cc(C3CC3)c12] | 8-(3-fluoro-4-aminomethyl-phenyl)-1-cyclopropyl-9-methyl-4-oxo-quinolizine-3-carboxylic acid |

-continued

| Compounds | Structure | Name |
|---|---|---|
| Example 50 | 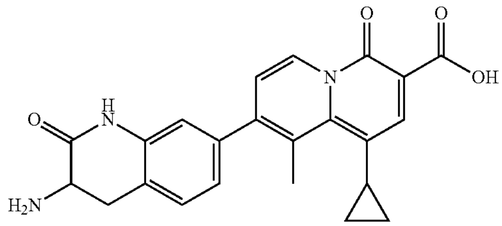 [SMILES: Cc1c(-c2ccc3c(c2)NC(=O)C(N)C3)ccn2c(=O)c(C(=O)O)cc(C3CC3)c12] | 8-(3-amino-2-oxo-3,4-dihydro-1H-quinolin-7-yl)-1-cyclopropyl-9-methyl-4-oxo-quinolizine-3-carboxylic acid |
| Example 51 | 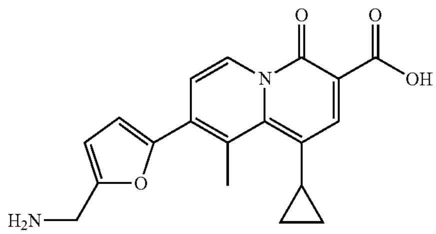 [SMILES: Cc1c(-c2ccc(CN)o2)ccn2c(=O)c(C(=O)O)cc(C3CC3)c12] | 8-[5-(aminomethyl)-2-furyl]-1-cyclopropyl-9-methyl-4-oxo-quinolizine-3-carboxylic acid |
| Example 52 | | 8-(4-cyano-phenyl)-1-cyclopropyl-9-methyl-4-oxo-quinolizine-3-carboxylic acid | and pharmaceutically acceptable salts thereof (e.g., a potassium salt thereof).

In certain other embodiments, the compound for use in the preceding method is selected from the group consisting of, 8-(3-fluoro-4-amino-phenyl)-1-cyclopropyl-9-methyl-4-oxo-quinolizine-3-carboxylic acid;
8-(6-amino-3-pyridyl)-1-cyclopropyl-9-methyl-4-oxo-quinolizine-3-carboxylic acid;
8-(1H-indazol-5-yl)-1-cyclopropyl-9-methyl-4-oxo-quinolizine-3-carboxylic acid;
8-(3,6-difluoro-4-amino-phenyl)-1-cyclopropyl-9-methyl-4-oxo-quinolizine-3-carboxylic acid;
8-(4-hydroxy-phenyl)-1-cyclopropyl-9-methyl-4-oxo-quinolizine-3-carboxylic acid;
and pharmaceutically acceptable salts thereof (e.g., a potassium salt thereof).

In an embodiment of any of the preceding embodiments, the pathogen can be selected from the group consisting of, (a) *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter* sp, *Enterobacter cloacae, Enterococcus faecium, Enterococcus gallinarum, Francisella tularensis, Klebsiella aerogenes, Listeria monocytogenes, Moraxella catarrhalis, Morganella morganii, Neisseria meningitides, Proteus mirabilis, Providencia stuartii, Serratia marcescens, Shigella* sp, *Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pyogenes, Streptococcus oralis, Streptococcus sanguis*, Group C *Streptococcus*, and *Yersinia pestis*, (b) drug-resistant strains of any pathogen of part (a); and (c) and drug-resistant strains of *Staphylococcus aureus, Staphylococcus epidermis, Streptococcus pneumoniae, Enterococcus faecalis, Escherichia coli, Klebsiella pneumoniae, Pseudomonas aeruginosa*, and *Haemophilus influenza*.

In another embodiment of any of the preceding embodiments, the pathogen can be selected from the group consisting of *Acinetobacter baumannii, Staphylococcus aureus, Enterococcus faecalis, Enterococcus faecium, Escherichia coli, Pseudomonas aeruginosa, Klebsiella pneumoniae, Haemophilus influenza, Stenotrophomonas maltophilia, Streptococcus pneumoniae*, and drug-resistant strains thereof.

In another embodiment of any of the preceding embodiments, the pathogen can be *Burkholderia mallei, Burkholderia pseudomallei, Bacillus anthracis, Francisella tularensis, Yersinia pestis*, or *Brucella abortus*.

In another embodiment of any of the preceding embodiments, the pathogen is *Acinetobacter baumannii*, or a drug-resistant strain thereof.

In another embodiment of any of the preceding embodiments, the pathogen is *Burkholderia cepacia, Burkholderia mallei, Burkholderia pseudomallei, Burkholderia thailandensis*, or a drug-resistant strain thereof.

In another embodiment of any of the preceding embodiments, the pathogen is *Citrobacter freundii*, or a drug-resistant strain thereof.

In another embodiment of any of the preceding embodiments, the pathogen is *Corynebacterium jeikeium*, or a drug-resistant strain thereof.

In another embodiment of any of the preceding embodiments, the pathogen is *Enterobacter* sp, *Enterobacter cloacae, Enterococcus faecalis, Enterococcus faecium*, or a drug-resistant strain thereof.

In another embodiment of any of the preceding embodiments, the pathogen is *Enterococcus gallinarum*, or a drug-resistant strain thereof.

In another embodiment of any of the preceding embodiments, the pathogen is *Escherichia coli*, or a drug-resistant strain thereof.

In another embodiment of any of the preceding embodiments, the pathogen is *Haemophilus influenza*, or a drug-resistant strain thereof.

In another embodiment of any of the preceding embodiments, the pathogen is *Klebsiella aerogenes, Klebsiella pneumoniae*, or a drug-resistant strain thereof.

In another embodiment of any of the preceding embodiments, the pathogen is *Listeria monocytogenes*, or a drug-resistant strain thereof.

In another embodiment of any of the preceding embodiments, the pathogen is *Moraxella catarrhalis*, or a drug-resistant strain thereof.

In another embodiment of any of the preceding embodiments, the pathogen is *Morganella morganii*, or a drug-resistant strain thereof.

In another embodiment of any of the preceding embodiments, the pathogen is *Neisseria meningitides*, or a drug-resistant strain thereof.

In another embodiment of any of the preceding embodiments, the pathogen is *Proteus mirabilis*, or a drug-resistant strain thereof.

In another embodiment of any of the preceding embodiments, the pathogen is *Providencia stuartii*, or a drug-resistant strain thereof.

In another embodiment of any of the preceding embodiments, the pathogen is *Pseudomonas aeruginosa*, or a drug-resistant strain thereof.

In another embodiment of any of the preceding embodiments, the pathogen is *Serratia marcescens*, or a drug-resistant strain thereof.

In another embodiment of any of the preceding embodiments, the pathogen is *Shigella* sp, or a drug-resistant strain thereof.

In another embodiment of any of the preceding embodiments, the pathogen is *Staphylococcus aureus, Staphylococcus epidermis, Staphylococcus haemolyticus, Staphylococcus saprophyticus*, or a drug-resistant strain thereof.

In another embodiment of any of the preceding embodiments, the pathogen is *Stenotrophomonas maltophilia*, or a drug-resistant strain thereof.

In another embodiment of any of the preceding embodiments, the pathogen is *Streptococcus agalactiae, Streptococcus bovis, Streptococcus constellatus, Streptococcus mitis, Streptococcus pneumoniae, Streptococcus pyogenes, Streptococcus oralis, Streptococcus sanguis*, Group C *Streptococcus*, or a drug-resistant strain thereof.

In another embodiment of any of the preceding embodiments, the pathogen is a drug-resistant strain.

In another embodiment of any of the preceding embodiments, the pathogen is *Staphylococcus aureus* ATCC 25923, *Staphylococcus aureus* ATCC 43300, *Staphylococcus aureus* BAA-1720, *Enterobacter faecium* ATCC 19434, *Enterobacter faecalis* ATCC 29212, *Streptococcus pneumoniae* ATCC 49619, *Escherichia coli* ATCC 25922, *Acinetobacter baumannii* ATCC 19606, *Pseudomonas aeruginosa* ATCC 27853 *Klebsiella pneumoniae* ATCC 33495, *Haemophilus influenzae* ATCC 49247, or *Stenotrophomonas maltophilia* ATCC 17677.

In another embodiment of any of the preceding embodiments, the pathogen is *Staphylococcus aureus, Staphylococcus epidermidis, Staphylococcus haemolyticus, Staphylococcus saprophyticus, Enterococcus faecalis, Enterococcus faecium, Enterococcus gallinarum, Streptococcus pneumoniae, Streptococcus pyogenes, Streptococcus agalactiae, Streptococcus agalactiae*, Group C *Streptococcus, Streptococcus mitis, Streptococcus constellatus, Streptococcus oralis, Streptococcus bovis, Streptococcus sanguis, Corynebacterium jeikeium, Listeria monocytogenes, Escherichia coli, Klebsiella aerogenes, Klebsiella pneumonia, Enterobacter* sp, *Serratia marcescens, Pseudomonas aeruginosa, Stenotrophomonas maltophila, Burkholderia cepacia, Proteus mirabilis, Shigella* sp, *Morganella morganii, Providencia stuartii, Neisseria meningitidis, Haemophilus influenza, Moraxella catarrhalis, Acinetobacter baumannii*, or *Citrobacter freundii*.

In another embodiment of any of the preceding embodiments, the pathogen is *Staphylococcus aureus*, EMRSA16 *Staphylococcus aureus, Enterococcus faecali, Enterococcus faecium, Streptococcus pneumonia, Escherichia coli Pseudomonas aeruginosa, Providencia stuartii*, or *Acinetobacter baumannii*

In another embodiment of any of the preceding embodiments, the pathogen is a class A or class B select biothreat agents as defined by the CDC (Centers for Disease Control and Prevention).

In another embodiment of any of the preceding embodiments, the pathogen is *Bacillus anthracis* Ames strain, *Brucella abortus* ATCC 23448, *Burkholderia mallei* ATCC 23344, *Burkholderia pseudomallei* ATCC 23343, *Francisella tularensis* Schu S4, or *Yersinia pestis* CO92.

In another embodiment, the pathogen is selected from the group consisting of *Burkholderia cepacia, Acinetobacter baumannii, Staphylococcus aureus, Enterococcus faecalis, Enterococcus faecium, Escherichia coli, Pseudomonas aeruginosa, Klebsiella pneumoniae, Haemophilus influenza, Streptococcus pneumoniae, Streptococcus pyogenes*, Group C *Streptococcus*, and drug-resistant strains thereof; and the compound is 8-(3-fluoro-4-amino-phenyl)-1-cyclopropyl-7-fluoro-9-methyl-4-oxo-quinolizine-3-carboxylic acid;

8-(3-fluoro-4-amino-phenyl)-1-cyclopropyl-9-methyl-4-oxo-quinolizine-3-carboxylic acid;

8-(4-amino-phenyl)-1-cyclopropyl-7-fluoro-9-methyl-4-oxo-quinolizine-3-carboxylic acid;

8-(4-carbamoyl-phenyl)-1-cyclopropyl-7-fluoro-9-methyl-4-oxo-quinolizine-3-carboxylic acid;

8-(4-pyridyl)-1-cyclopropyl-9-methyl-4-oxo-quinolizine-3-carboxylic acid;

8-(6-amino-3-pyridyl)-1-cyclopropyl-9-methyl-4-oxo-quinolizine-3-carboxylic acid;

8-(1H-indazol-5-yl)-1-cyclopropyl-9-methyl-4-oxo-quinolizine-3-carboxylic acid;

8-(3,6-difluoro-4-amino-phenyl)-1-cyclopropyl-9-methyl-4-oxo-quinolizine-3-carboxylic acid;

8-(4-aminomethyl-phenyl)-1-cyclopropyl-9-methyl-4-oxo-quinolizine-3-carboxylic acid;

8-(3,5-difluoro-4-amino-phenyl)-1-cyclopropyl-9-methyl-4-oxo-quinolizine-3-carboxylic acid;

8-(1,2,3,6-tetrahydro-pyridin-4-yl)-1-cyclopropyl-9-methyl-4-oxo-quinolizine-3-carboxylic acid;

8-(4-hydroxy-phenyl)-1-cyclopropyl-9-methyl-4-oxo-quinolizine-3-carboxylic acid;

or a pharmaceutically acceptable salt thereof (e.g., a potassium salt thereof).

In another embodiment, the pathogen is selected from the group consisting of *Burkholderia mallei, Burkholderia pseudomallei, Bacillus anthracis, Yersinia pestis, Francisella tularensis*, and *Brucella abortus*, and the compound is 8-(3-fluoro-4-amino-phenyl)-1-cyclopropyl-7-fluoro-9-methyl-4-oxo-quinolizine-3-carboxylic acid;
8-(3-fluoro-4-amino-phenyl)-1-cyclopropyl-9-methyl-4-oxo-quinolizine-3-carboxylic acid;
8-(3-amino-phenyl)-1-cyclopropyl-9-methyl-4-oxo-quinolizine-3-carboxylic acid;
8-(3-amino-4-fluoro-phenyl)-1-cyclopropyl-9-methyl-4-oxo-quinolizine-3-carboxylic acid;
8-(3-amino-5-fluoro-phenyl)-1-cyclopropyl-9-methyl-4-oxo-quinolizine-3-carboxylic acid;
8-(4-pyridyl)-1-cyclopropyl-9-methyl-4-oxo-quinolizine-3-carboxylic acid;
8-(2-fluoro-4-pyridyl)-1-cyclopropyl-9-methyl-4-oxo-quinolizine-3-carboxylic acid;
8-(6-amino-3-pyridyl)-1-cyclopropyl-9-methyl-4-oxo-quinolizine-3-carboxylic acid;
8-(1H-indazol-5-yl)-1-cyclopropyl-9-methyl-4-oxo-quinolizine-3-carboxylic acid;
8-(3,6-difluoro-4-amino-phenyl)-1-cyclopropyl-9-methyl-4-oxo-quinolizine-3-carboxylic acid;
8-(4-aminomethyl-phenyl)-1-cyclopropyl-9-methyl-4-oxo-quinolizine-3-carboxylic acid;
8-(1,2,3,6-tetrahydro-pyridin-4-yl)-1-cyclopropyl-9-methyl-4-oxo-quinolizine-3-carboxylic acid;
8-(4-chloro-phenyl)-1-cyclopropyl-9-methyl-4-oxo-quinolizine-3-carboxylic acid;
8-(4-hydroxy-phenyl)-1-cyclopropyl-9-methyl-4-oxo-quinolizine-3-carboxylic acid;
8-(4-hydroxymethyl-phenyl)-1-cyclopropyl-9-methyl-4-oxo-quinolizine-3-carboxylic acid;
or a pharmaceutically acceptable salt thereof (e.g., a potassium salt thereof).

In another embodiment, the pathogen is selected from the group consisting of *Staphylococcus aureus, Enterococcus faecalis, Enterococcus faecium, Streptococcus pneumoniae, Streptococcus pyogenes*, Group C *Streptococcus, Escherichia coli, Klebsiella pneumoniae, Pseudomonas aeruginosa, Burkholderia cepacia, Haemophilus influenzae, Acinetobacter baumannii*, and drug resistant strains thereof; and the compound is
8-(3-fluoro-4-amino-phenyl)-1-cyclopropyl-7-fluoro-9-methyl-4-oxo-quinolizine-3-carboxylic acid;
8-(3-fluoro-4-amino-phenyl)-1-cyclopropyl-9-methyl-4-oxo-quinolizine-3-carboxylic acid;
8-(4-amino-phenyl)-1-cyclopropyl-7-fluoro-9-methyl-4-oxo-quinolizine-3-carboxylic acid;
8-(4-carbamoyl-phenyl)-1-cyclopropyl-7-fluoro-9-methyl-4-oxo-quinolizine-3-carboxylic acid;
8-(4-pyridyl)-1-cyclopropyl-9-methyl-4-oxo-quinolizine-3-carboxylic acid;
8-(6-amino-3-pyridyl)-1-cyclopropyl-9-methyl-4-oxo-quinolizine-3-carboxylic acid;
8-(1H-indazol-5-yl)-1-cyclopropyl-9-methyl-4-oxo-quinolizine-3-carboxylic acid;
8-(3,6-difluoro-4-amino-phenyl)-1-cyclopropyl-9-methyl-4-oxo-quinolizine-3-carboxylic acid;
8-(4-aminomethyl-phenyl)-1-cyclopropyl-9-methyl-4-oxo-quinolizine-3-carboxylic acid;
8-(3,5-difluoro-4-amino-phenyl)-1-cyclopropyl-9-methyl-4-oxo-quinolizine-3-carboxylic acid;
8-(1,2,3,6-tetrahydro-pyridin-4-yl)-1-cyclopropyl-9-methyl-4-oxo-quinolizine-3-carboxylic acid;
8-(4-hydroxy-phenyl)-1-cyclopropyl-9-methyl-4-oxo-quinolizine-3-carboxylic acid;
or a pharmaceutically acceptable salt thereof (e.g., a potassium salt thereof).

In another embodiment, the pathogen is selected from the group consisting of *Staphylococcus aureus, Staphylococcus epidermidis, Staphylococcus haemolyticus, Staphylococcus saprophyticus, Enterococcus faecalis, Enterococcus faecium, Enterococcus gallinarum, Streptococcus pneumonia, Streptococcus pyogenes, Streptococcus agalactiae*, Group C *Streptococcus, Streptococcus mitis, Streptococcus constellatus, Streptococcus oralis, Streptococcus bovis, Streptococcus sanguis, Corynebacterium jeikeium, Listeria monocytogenes, Escherichia coli, Klebsiella aerogenes, Klebsiella pneumoniae, Enterobacter* sp, *Serratia marcescens, Pseudomonas aeruginosa, Stenotrophomonas maltophilia, Burkholderia cepacia, Proteus mirabilis, Shigella* sp, *Morganella morganii, Providencia stuartii, Neisseria meningitides, Haemophilus influenza, Moraxella catarrhalis, Acinetobacter baumannii, Citrobacter freundii*, and drug resistant strains thereof; and the compound is
8-(3-fluoro-4-amino-phenyl)-1-cyclopropyl-7-fluoro-9-methyl-4-oxo-quinolizine-3-carboxylic acid;
8-(3-fluoro-4-amino-phenyl)-1-cyclopropyl-9-methyl-4-oxo-quinolizine-3-carboxylic acid;
8-(4-amino-phenyl)-1-cyclopropyl-7-fluoro-9-methyl-4-oxo-quinolizine-3-carboxylic acid;
8-(4-carbamoyl-phenyl)-1-cyclopropyl-7-fluoro-9-methyl-4-oxo-quinolizine-3-carboxylic acid;
8-(4-pyridyl)-1-cyclopropyl-9-methyl-4-oxo-quinolizine-3-carboxylic acid;
8-(6-amino-3-pyridyl)-1-cyclopropyl-9-methyl-4-oxo-quinolizine-3-carboxylic acid;
8-(1H-indazol-5-yl)-1-cyclopropyl-9-methyl-4-oxo-quinolizine-3-carboxylic acid;
8-(3,6-difluoro-4-amino-phenyl)-1-cyclopropyl-9-methyl-4-oxo-quinolizine-3-carboxylic acid;
8-(4-aminomethyl-phenyl)-1-cyclopropyl-9-methyl-4-oxo-quinolizine-3-carboxylic acid;
8-(3,5-difluoro-4-amino-phenyl)-1-cyclopropyl-9-methyl-4-oxo-quinolizine-3-carboxylic acid;
8-(1,2,3,6-tetrahydro-pyridin-4-yl)-1-cyclopropyl-9-methyl-4-oxo-quinolizine-3-carboxylic acid;
8-(4-hydroxy-phenyl)-1-cyclopropyl-9-methyl-4-oxo-quinolizine-3-carboxylic acid;
or a pharmaceutically acceptable salt thereof (e.g., a potassium salt thereof).

In another embodiment, the pathogen is selected from the group consisting of *Staphylococcus aureus, Enterococcus faecalis, Enterococcus faecium, Streptococcus pneumoniae, Streptococcus pyogenes*, Group C *Streptococcus, Escherichia coli, Klebsiella pneumoniae, Pseudomonas aeruginosa, Burkholderia cepacia, Haemophilus influenzae, Acinetobacter baumannii*, and drug resistant strains thereof; and the compound is
8-(4-aminomethyl-phenyl)-1-cyclopropyl-9-methyl-4-oxo-quinolizine-3-carboxylic acid;
8-(3,5-difluoro-4-amino-phenyl)-1-cyclopropyl-9-methyl-4-oxo-quinolizine-3-carboxylic acid;
8-(1,2,3,6-tetrahydro-pyridin-4-yl)-1-cyclopropyl-9-methyl-4-oxo-quinolizine-3-carboxylic acid;
8-(4-hydroxy-phenyl)-1-cyclopropyl-9-methyl-4-oxo-quinolizine-3-carboxylic acid;
or a pharmaceutically acceptable salt thereof (e.g., a potassium salt thereof).

In another embodiment, the pathogen is *Methicillin*-resistant *Staphylococcus aureus* and the compound is
8-(3-fluoro-4-amino-phenyl)-1-cyclopropyl-9-methyl-4-oxo-quinolizine-3-carboxylic acid;
8-(6-amino-3-pyridyl)-1-cyclopropyl-9-methyl-4-oxo-quinolizine-3-carboxylic acid;

8-(1H-indazol-5-yl)-1-cyclopropyl-9-methyl-4-oxo-quinolizine-3-carboxylic acid;

8-(3,6-difluoro-4-amino-phenyl)-1-cyclopropyl-9-methyl-4-oxo-quinolizine-3-carboxylic acid;

8-(4-hydroxy-phenyl)-1-cyclopropyl-9-methyl-4-oxo-quinolizine-3-carboxylic acid;

or a pharmaceutically acceptable salt thereof (e.g., a potassium salt thereof).

In another aspect, the present disclosure provides compounds of the formula (II),

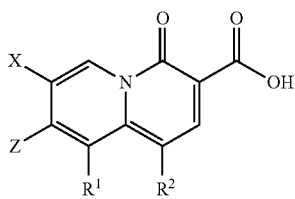

(II)

or a pharmaceutically acceptable salt thereof, wherein $R^1$ is hydrogen, halogen, cyano, $C_{1-8}$ alkyl, $C_{1-8}$ haloalkyl, heterocyclyl, —$OR^{11}$, —$N(R^{11})_2$, or —$C(O)N(R^{11})_2$, wherein each $R^{11}$ is independently hydrogen, $C_{1-8}$ alkyl, or $C_{1-8}$ haloalkyl;

$R^2$ is a $C_{1-8}$ alkyl, $C_{1-8}$ haloalkyl, $C_{3-8}$cycloalkyl, or heteroaryl, wherein the cycloalkyl and heteroaryl are optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl;

Z is a bicyclic heteroaryl, optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Z$, or —$C_{1-8}$ alkyl-$R^Z$, wherein $R^Z$ is nitro, cyano, —$OR^{Z1}$, —$SR^{Z1}$, —$N(R^{Z1})_2$, —$C(O)R^{Z1}$, —$C(O)OR^{Z1}$, —$C(O)N(R^{Z1})_2$, —$OC(O)R^{Z1}$, —$OC(O)OR^{Z1}$, —$OC(O)N(R^{Z1})_2$, —$N(R^{Z1})C(O)R^{Z1}$, —$N(R^{Z1})C(O)OR^{Z1}$, —$N(R^{Z1})C(O)N(R^{Z1})_2$, —$S(O)_2R^{Z1}$, —$S(O)_2OR^{Z1}$, —$S(O)_2N(R^{Z1})_2$, —$OS(O)_2R^{Z1}$, —$OS(O)_2OR^{Z1}$, —$OS(O)_2N(R^{Z1})_2$, —$N(R^{Z1})S(O)_2R^{Z1}$, —$N(R^{Z1})S(O)_2OR^{Z1}$, or —$N(R^{Z1})S(O)_2N(R^{Z1})_2$, wherein each $R^{Z1}$ is independently hydrogen, $C_{1-8}$ alkyl, or $C_{1-8}$ haloalkyl; and X is hydrogen, halogen, cyano, $C_{1-8}$ alkyl, $C_{1-8}$haloalkyl, —$OR^X$, —$N(R^X)_2$, —$C(O)R^X$, —$C(O)OR^X$, or —$C(O)N(R^X)_2$, wherein each $R^X$ is independently hydrogen, $C_{1-8}$ alkyl, or $C_{1-8}$haloalkyl.

In one embodiment of the compounds of formula (II), $R^1$ is hydrogen, halogen, or $C_{1-8}$ alkyl. In another embodiment, $R^1$ is hydrogen or $C_{1-8}$ alkyl. In another embodiment, $R^1$ is hydrogen or methyl. In another embodiment, $R^1$ is halogen or $C_{1-8}$ alkyl. In another embodiment, $R^1$ is $C_{1-8}$ alkyl. In another embodiment, $R^1$ is halogen. In another embodiment of the compounds of formula (II), $R^1$ is $C_{1-8}$ haloalkyl, —$OR^{11}$, or —$C(O)N(R^{11})_2$. In another embodiment of the compounds of formula (II), $R^1$ is trifluoromethyl, methoxy, or —$C(O)NH_2$.

In certain embodiments, the compound for formula (II) is of one of the formulas,

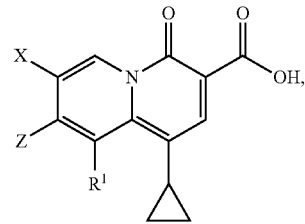

(IIa)

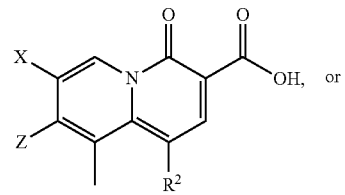

(IIb)

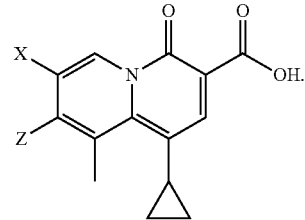

(IIc)

In one embodiment of the compounds of formula (II), (IIa)-(IIc), and any embodiment thereof, X is hydrogen or halogen. In another embodiment, X is hydrogen. In another embodiment, X is halogen. In another embodiment, X is fluoro. In another embodiment, X is hydrogen, halogen, $C_{1-8}$ alkyl, $C_{1-8}$ alkoxy, amino, $C_{1-8}$ alkylamino, or di($C_{1-8}$ alkyl) amino. In another embodiment, X is —$OR^X$, —$N(R^X)_2$, —$C(O)R^X$, —$C(O)OR^X$, or —$C(O)N(R^X)_2$. In another embodiment, X is —$O(R^X)$ or —$N(R^X)_2$. In another embodiment, X is —$C(O)R^X$, —$C(O)OR^X$, or —$C(O)N(R^X)_2$. In another embodiment, X is $C_{1-8}$haloalkyl (e.g., trifluoromethyl).

In particular embodiments of the compounds of formula (II) and (IIa), $R^1$ and X are selected from one of the following combinations:

(a) $R^1$ is hydrogen, halogen, or $C_{1-8}$ alkyl; and X is hydrogen or halogen.
(b) $R^1$ is hydrogen, halogen, or $C_{1-8}$ alkyl; and X is hydrogen.
(c) $R^1$ is hydrogen, halogen, or $C_{1-8}$ alkyl; and X is halogen.
(d) $R^1$ is hydrogen, halogen, or $C_{1-8}$ alkyl; and X is fluoro.
(e) $R^1$ is hydrogen or $C_{1-8}$ alkyl; and X is hydrogen or halogen.
(f) $R^1$ is hydrogen or $C_{1-8}$ alkyl; and X is hydrogen.
(g) $R^1$ is hydrogen or $C_{1-8}$ alkyl; and X is halogen.
(h) $R^1$ is hydrogen or $C_{1-8}$ alkyl; and X is fluoro.
(i) $R^1$ is hydrogen or methyl; and X is hydrogen or halogen.
(j) $R^1$ is hydrogen or methyl; and X is hydrogen.
(k) $R^1$ is hydrogen or methyl; and X is halogen.
(l) $R^1$ is hydrogen or methyl; and X is fluoro.
(m) $R^1$ is halogen or $C_{1-8}$ alkyl; and X is hydrogen or halogen.
(n) $R^1$ is halogen or $C_{1-8}$ alkyl; and X is hydrogen.
(o) $R^1$ is halogen or $C_{1-8}$ alkyl; and X is halogen.
(p) $R^1$ is halogen or $C_{1-8}$ alkyl; and X is fluoro.
(q) $R^1$ is $C_{1-8}$ alkyl; and X is hydrogen or halogen.
(r) $R^1$ is $C_{1-8}$ alkyl; and X is hydrogen.
(s) $R^1$ is $C_{1-8}$ alkyl; and X is halogen.
(t) $R^1$ is $C_{1-8}$ alkyl; and X is fluoro.

In another embodiment of the compounds of formula (II), (IIa)-(IIc), and any embodiment thereof, Z is a benzofuranyl, benzothienyl, indolyl, indazolyl, benzimidazolyl, benzoxazolyl, benzoisoxazolyl, benzothiazolyl, benzoisothiazolyl, or benzotriazolyl, each optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Z$, or —$C_{1-8}$ alkyl-$R^Z$.

In another embodiment of the compounds of formula (II), (IIa)-(IIc), and any embodiment thereof, Z is indazolyl optionally substituted by one to five groups that are each independently halogen, $C_{1-8}$ alkyl, $C_{1-8}$ haloalkyl, $C_{3-8}$cycloalkyl, heterocyclyl, aryl, heteroaryl, $C_{3-8}$cycloalkyl($C_{1-8}$) alkyl, heterocyclyl($C_{1-8}$)alkyl, aryl($C_{1-8}$)alkyl, heteroaryl($C_{1-8}$)alkyl, —$R^Z$, or —$C_{1-8}$ alkyl-$R^Z$.

In another embodiment of the compounds of formula (II), (IIa)-(IIc), and any embodiment thereof, Z is indazolyl.

In one embodiment of the compounds of formula (II) and (IIb), and any embodiment thereof, $R^2$ is a $C_{1-8}$ alkyl, $C_{1-8}$ haloalkyl, or $C_{3-8}$cycloalkyl.

In one embodiment of the compounds of formula (II) and (IIb), and any embodiment thereof, $R^2$ is a $C_{1-8}$ alkyl (e.g., methyl).

In one embodiment of the compounds of formula (II) and (IIb), and any embodiment thereof, $R^2$ is a $C_{1-8}$ haloalkyl (e.g., trifluoromethyl).

In one embodiment of the compounds of formula (II) and (IIb), and any embodiment thereof, $R^2$ is $C_{3-8}$cycloalkyl (e.g., cyclopropyl, cyclobutyl, cyclopentyl, or cyclohexyl).

In one embodiment of the compounds of formula (II) and (IIb), and any embodiment thereof, $R^2$ is $C_{3-8}$cycloalkyl optionally substituted by one or two groups that are each independently halogen or $C_{1-8}$ alkyl (e.g., fluoro or methyl).

In another embodiment of the compounds of formula (II) and (IIb), and any embodiment thereof, $R^2$ is heteroaryl, wherein the heteroaryl is optionally substituted with one to five groups that are each independently halogen, $C_{1-8}$ alkyl, —$OR^{21}$, —$N(R^{21})_2$, or —$C(O)OR^{21}$, wherein each $R^{21}$ is independently hydrogen or $C_{1-8}$ alkyl.

In another aspect, the present disclosure provides pharmaceutical compositions comprising a compound of the formula (I) or (II), a pharmaceutically acceptable salt thereof, or any embodiment thereof, and a pharmaceutically acceptable carrier, excipient, or diluent.

In another aspect, the present disclosure provides compound of the formula (I) or (II), a pharmaceutically acceptable salt thereof, or any of the preceding embodiments thereof, for treating an infection caused by a pathogen selected from the group consisting of *Burkholderia mallei, Burkholderia pseudomallei, Burkholderia cepacia, Bacillus anthracis, Yersinia pestis, Francisella tularensis, Brucella abortus, Burkholderia thailandensis, Acinetobacter baumannii, Acinetobacter baumannii, Staphylococcus aureus, Staphylococcus epidermis, Enterococcus faecalis, Enterococcus faecium, Escherichia coli, Enterobacter cloacae, Pseudomonas aeruginosa, Klebsiella pneumoniae, Haemophilus influenza, Stenotrophomonas maltophilia, Streptococcus pneumoniae, Streptococcus pyogenes*, Group C *Streptococcus*, and drug-resistant strains thereof.

In certain embodiments, the compound of formula (I) or (II) reduces the risk of contagion caused by an infection induced by a pathogen selected from the group consisting of *Burkholderia mallei, Burkholderia pseudomallei, Burkholderia cepacia, Bacillus anthracis, Yersinia pestis, Francisella tularensis, Brucella abortus, Burkholderia thailandensis, Acinetobacter baumannii, Acinetobacter baumannii, Staphylococcus aureus, Staphylococcus epidermis, Enterococcus faecalis, Enterococcus faecium, Escherichia coli, Enterobacter cloacae, Pseudomonas aeruginosa, Klebsiella pneumoniae, Streptococcus pneumoniae, Streptococcus pyogenes*, Group C *Streptococcus*, and drug-resistant strains thereof, in an individual at risk of acquiring the infection by at least 5%, or at least 10%, or at least 15%, or at least 20%, or at least 30% or at least 40%, or at least 50%, or at least 60%, or at least 70% or at least 80%, or at least 90%, or more.

In another aspect, the present disclosure provides methods for treating an infection comprising, providing to a subject infected by a pathogen selected from the group consisting of *Acinetobacter baumannii, Bacillus anthracis, Brucella abortus, Burkholderia cepacia, Burkholderia mallei, Burkholderia pseudomallei, Burkholderia thailandensis, Citrobacter freundii, Corynebacterium jeikeium, Enterobacter* sp, *Enterobacter cloacae, Enterococcus faecalis, Enterococcus faecium, Enterococcus gallinarum, Escherichia coli, Francisella tularensis, Haemophilus influenza, Klebsiella aerogenes, Klebsiella pneumoniae, Listeria monocytogenes, Moraxella catarrhalis, Morganella morganii, Neisseria meningitides, Proteus mirabilis, Providencia stuartii, Pseudomonas aeruginosa, Serratia marcescens, Shigella* sp, *Staphylococcus aureus, Staphylococcus epidermis, Staphylococcus haemolyticus, Staphylococcus saprophyticus, Stenotrophomonas maltophilia, Streptococcus agalactiae, Streptococcus bovis, Streptococcus constellatus, Streptococcus mitis, Streptococcus pneumoniae, Streptococcus pyogenes, Streptococcus oralis, Streptococcus sanguis*, Group C *Streptococcus, Yersinia pestis*, and drug-resistant strains thereof, a therapeutically effective amount of a compound selected from the group consisting of 8-(3-fluoro-4-amino-phenyl)-1-cyclopropyl-9-methyl-4-oxo-quinolizine-3-carboxylic acid 8-(6-amino-3-pyridyl)-1-cyclopropyl-9-methyl-4-oxo-quinolizine-3-carboxylic acid 8-(1H-indazol-5-yl)-1-cyclopropyl-9-methyl-4-oxo-quinolizine-3-carboxylic acid 8-(3,6-difluoro-4-amino-phenyl)-1-cyclopropyl-9-methyl-4-oxo-quinolizine-3-carboxylic acid 8-(4-hydroxy-phenyl)-1-cyclopropyl-9-methyl-4-oxo-quinolizine-3-carboxylic acid and pharmaceutically acceptable salts thereof (e.g., a potassium salt thereof), wherein the compound is provided to the subject as either (a) an oral formulation that, when given orally in a mouse model, has one or more of (i) peak serum concentration ($C_{max}$)>0.15 μg/mL; (ii) $t_{max}$<45 minutes; (iii) half-life ($t_{1/2}$)≥1 hour; and/or (iv) oral bioavailability (F)>40%; or (b) an intravenous formulation that, when given intravenously in a mouse model, has one or more of (i) an apparent volume of distribution ($V_d$)>5000 mL/kg; and/or (ii) half-life ($t_{1/2}$)≥1 hour.

Treatment

According to the present invention, treatment may be given either to a subject infected by the pathogen, or may be a subject at risk of acquiring such an infection. Generally, the subject is mammalian, such as a human or animal mammalian.

The treatment may be ameliorating or curative. By curative, it is intended to mean survival from the infection which otherwise in the absence of the treatment causes the subject suffering from the infection to show increasing pathology or even morbidity.

In another embodiment of the invention the treatment is prophylactic treatment. Thus, the pharmaceutical compositions described herein may be prepared for prophylactic treatment of an infection by a pathogen in an individual at risk of infection by the pathogen.

In one embodiment of the invention, the pharmaceutical composition is for reducing the risk of contagion caused by the infection or in an individual at risk of acquiring an infection by the pathogen. In relation to epidemic or even pandemic infections causing a high mortality rate, even slight reductions in risk of contagion may be of major importance.

In another embodiment, the pharmaceutical composition reduces the risk of contagion in a subject that has acquired the infection by at least 5%, preferably at least 10%, preferably at least 15%, more preferably at least 20%, or at least 30% or at least 40%, or at least 50%, or at least 60%, or at least 70% or at least 80%, or at least 90%, or more.

The pharmaceutical compositions of the invention may also reduce the risk of contagion caused by an infection in an individual at risk of acquiring that infection by at least 5%, or at least 10%, or at least 15%, or at least 20%, or at least 30% or at least 40%, or at least 50%, or at least 60%, or at least 70% or at least 80%, or at least 90%, or more.

Administration of the anti-infective pharmaceutical compositions according to the invention may be only once or administration may be repeated for a number of times. For example, the compositions may be given for a repeatedly with regular intervals, for example in the range of 1 to 5 times daily for in the range of 1 to 100 days, such as in the range of 1 to 50 days, for example in the range of 1 to 25 days, such as in the range of 10 to 16 days. The total daily dose of the compounds of this invention administered to a host in single or in divided doses can be in amounts, Single dose compositions may contain such amounts or submultiples thereof as make up the daily dose.

The pharmaceutical compositions may be prepared for any suitable administration route, for example, topical, parenteral, oral, buccal, systemic, nasal, injection, transdermal, rectal, vaginal, etc., or a form suitable for administration by inhalation or insufflation. For example, the pharmaceutical compositions of the invention are prepared for oral administration or for intraperitoneal administration, such as for oral administration. Similarly, the pharmaceutical compositions of the invention may or may be used at the site of a wound on or in the body, for example as a result of surgery or injury. Equally, the pharmaceutical compositions of the invention may or may be used for an internal infection at the site of a prosthesis.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

A compound, as described above, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged compound with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally.

The pharmaceutical composition may be in unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In therapeutic use, the compounds utilized in the methods of the invention may be administered to subjects at dosage levels suitable to achieve therapeutic benefit. By therapeutic benefit is meant that the administration of compound leads to a beneficial effect in the patient over time.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of the disease. For example, thr dose may vary depending on the symptoms, age, body weight, etc. of the patient. Usually, they are administered to adults in a dose of 0.05 to 100 mg/kg/day, preferably 0.1 to 50 mg/kg/day, in the systemic administration. When they are used for the local treatment, the concentration of the active ingredient is 0.01 to 5%, preferably 0.1 to 3%.

DEFINITIONS

The term "drug-resistant strain" as used herein means that the reference bacterial strain is either β-lactamase positive or resistant to one or more macrolide, beta-lactam, quinolone, carbapenem, aminoside, and/or glycopeptide antibiotic, including, but not limited to penicillin, methicillin, levofloxacin, ciprofloxacin, meropenem, imipenem, amikacin, tetracyclin, vancomycin, and polyoxin.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the phrase "pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucuronic or galacturonic acids and the like (see, e.g., Berge et al, 1977, J. Pharm. Sci. 66:1-19). In certain embodiments of any of the preceding compounds, methods, and embodiments thereof, the compound is a potassium salt.

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl, arylalkyl-, and -alkylaryl indicate the same functionality.

Further, certain terms herein may be used as both monovalent and divalent linking radicals as would be familiar to those skilled in the art, and by their presentation linking between two other moieties. For example, an alkyl group can be both a monovalent radical or divalent radical; in the latter case, it would be apparent to one skilled in the art that an additional hydrogen atom is removed from a monovalent alkyl radical to provide a suitable divalent moiety.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC$($CH_3$)—, —$CH_2CH(CH_2CH_3)CH_2$—.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, and benzo[d][1,3]dioxol-5-yl. In certain embodiments, the bicyclic aryl is naphthyl or a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —$(CH_2)_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, indazolyl, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "oxo" as used herein means a $=$O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a $=$S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

EXAMPLES

Analytical Methods

NMR spectra were recorded on a Bruker Avance-400 NMR or Bruker Avance-300 NMR or with samples in solution in deuterated chloroform ($CDCl_3$), deuterated methanol ($CD_3OD$) or deuterated dimethyl sulfoxide (DMSO-d6). Chemical shifts and coupling constants are respectively expressed in part per million (ppm) and in Herz (Hz). Mass spectrometry (MS) analyses were performed on an Agilent MSD G1946D or a Waters TQD with electrospray ionization (ESI). High resolution mass spectrometry (High-Res MS) analyses were recorded on a Shimadzu IT-TOF apparatus.

The following acronyms and abbreviations are used in the following examples:

| | |
|---|---|
| ACN | Acetonitrile |
| Boc or BOC | t-butoxycarbonyl |
| DMF | N,N-dimethylformamide |
| DMSO | Dimethylsulfoxide |
| ESI-MS | electrospray ionization mass spectrometry |
| HPLC | High-performance liquid chromatography |
| LCMS | Liquid chromatography-mass spectrometry |
| MeOH | methanol |
| nBuLi | n-butyl lithium |
| NMR | Nuclear magnetic resonance |
| Ph | Phenyl |
| TFA | Trifluoroacetic acid |
| THF | Tetrahydrofuran |

Synthetic Procedures and Analytical Data
Preparation of Scaffolds

Scaffold A

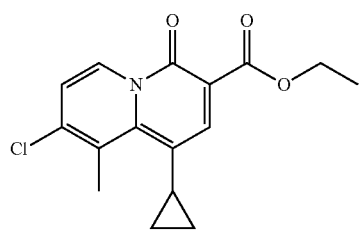

Scaffold B

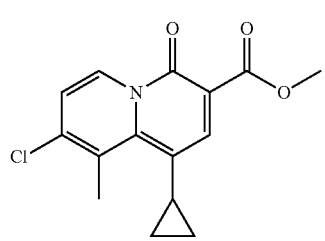

Scaffold C

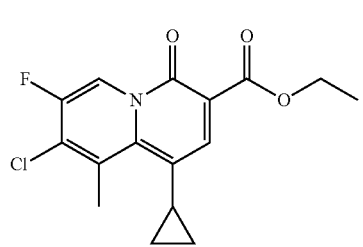

Scaffolds ethyl 8-chloro-1-cyclopropyl-9-methyl-4-oxo-quinolizine-3-carboxylate (Scaffold A) and methyl 8-chloro-1-cyclopropyl-9-methyl-4-oxo-quinolizine-3-carboxylate (Scaffold B) were prepared synthetically. Scaffold ethyl 8-chloro-1-cyclopropyl-7-fluoro-9-methyl-4-oxo-quinolizine-3-carboxylate (Scaffold C) was purchased from Beijing Louston Fine Chemical Co. Ltd., China.

Preparation of scaffold A ethyl 8-chloro-1-cyclopropyl-9-methyl-4-oxo-quinolizine-3-carboxylate Preparation of 2-bromo-3-methyl-4-chloro-pyridine

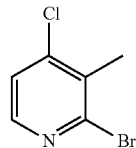

To a solution of 2,2,6,6-tetramethyl-pyridine (21.1 mL, 125 mmol) in freshly distilled THF (120 mL) at −78° C. was added nBuLi (50 mL, 125 mmol) in 30 min. The resulting mixture was stirred at −78° C. for 30 min and was added through a cannula over 30 min to a solution of 3-bromo-4-chloro-pyridine (20.0 g, 104 mmol) in freshly distilled THF (60 mL) that had been cooled to −78° C. prior to the addition. The reaction mixture was stirred at −78° C. for 30 min before iodomethane (7.78 mL, 125 mmol) was added over a period of 10 min. The reaction was stirred at −78° C. for 30 min and was allowed to warm up to room temperature prior to be quenched with aqueous $NH_4Cl$ (65 mL). The aqueous phase was extracted with ethyl acetate (2×150 mL). The organic phases were separated, dried, and concentrated. The residue was purified by flash silica column chromatography (hexane:ethyl acetate, 5:1) to afford the title compound as a yellow solid (10.6 g, 49%). $^1H$ NMR ($CDCl_3$, 300 MHz) δ ppm: 8.10 (d, J=5.1 Hz, 1H), 7.27 (d, J=5.1 Hz, 1H), 2.51 (s, 3H).

Preparation of (3-methyl-4-chloro-pyridin-2-yl)-cyclopropyl-methanol

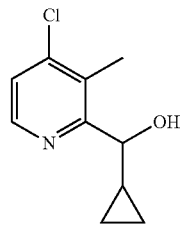

A solution of 2-bromo-3-methyl-4-chloro-pyridine (10.6 g, 57.1 mmol) in freshly distilled THF (120 mL) was cooled down to 0° C. and treated with isopropyl magnesium chloride (45.7 mL, 2.0 M in THF, 91.5 mmol). The resulting mixture was stirred at room temperature for 3 h then cooled to −5° C. Cyclopropane carboxaldehyde (6.83 mL, 91.5 mmol) was added. The reaction mixture was stirred at room temperature for 1 h and quenched by adding water (100 mL), and extracted with ethyl acetate (2×150 mL). The organic phase was separated, dried, and concentrated. The residue was purified by flash silica column chromatography (hexane:ethyl acetate, 3:1) to afford the title compound as a yellow oil (7.01 g, 62%). ESI-MS m/z: 198 (M+H)$^+$; $^1H$ NMR ($CDCl_3$, 300 MHz) δ ppm: 8.28 (d, J=5.4 Hz, 1H), 7.26 (d, J=5.4 Hz, 1H), 4.79 (d, J=5.4 Hz, 1H), 4.55 (br, s, 1H), 2.39 (s, 3H), 1.10-1.28 (m, 1H), 0.58-0.41 (m, 4H).

Preparation of (3-methyl-4-chloro-pyridin-2-yl)-cyclopropyl-methanone

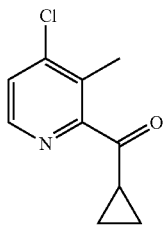

A solution of (3-methyl-4-chloro-pyridin-2-yl)-cyclopropyl-methanol (7.01 g, 35.5 mmol) in dichloromethane (80 mL) was treated with MnO$_2$ (30.8 g, 355 mmol) at room temperature overnight. The reaction mixture was filtered through a pad of Celite and the filtrate was concentrated to dryness, affording the title compound (6.82 g, 98%). ESI-MS m/z: 196 (M+H)$^+$; $^1$H NMR (CDCl$_3$, 300 MHz) δ ppm: 8.41 (d, J=5.4 Hz, 1H), 7.42 (d, J=5.4 Hz, 1H), 2.96-3.04 (m, 1H), 2.57 (s, 3H), 1.20-1.28 (m, 2H), 1.14-1.09 (m, 2H).

Preparation of 2-(1-cyclopropyl-2-methoxy-vinyl)-3-methyl-4-chloro-pyridine

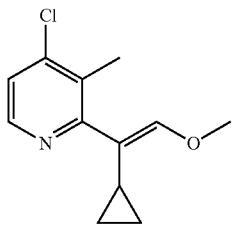

A solution of methoxymethyl triphenylphosphonium chloride (17.9 g, 52.3 mmol) in dry THF (80 mL) was treated with NaH (2.79 g, 69.8 mmol) at 0° C. for 3 h. To this mixture was added a solution of (3-methyl-4-chloro-pyridin-2-yl)-cyclopropyl-methanone (6.82 g, 34.9 mmol) in dry THF (20 mL). The reaction mixture was heated at 40° C. overnight. The reaction mixture was cooled down to room temperature and filtered. The filtrate was concentrated to dryness. The residue was purified by flash silica column chromatography (hexane:ethyl acetate, 3:1) to afford the title compound (6.41 g, 82%). ESI-MS m/z: 224 (M+H)$^+$; $^1$H NMR (CDCl$_3$, 300 MHz) δ ppm: 8.31 (d, J=5.4 Hz, 0.5; H), 8.23 (d, J=5.4 Hz, 0.5; H), 7.17 (d, J=5.4 Hz, 1H), 6.13-6.16 (m, 1H), 3.70 (s, 1.5; H), 3.56 (s, 1.5; H), 2.38 (s, 1.5; H), 2.31 (s, 1.5; H), 1.91-1.94 (m, 0.5; H), 1.63-1.65 (m, 0.5; H), 0.66-0.72 (m, 1H), 0.56-0.62 (m, 1H), 0.35-0.38 (m, 1H), 0.26-0.33 (m, 1H).

Preparation of 2-(3-methyl-4-chloro-pyridin-2-yl)-2-cyclopropyl-acetaldehyde

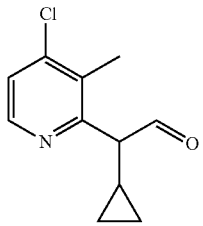

A solution of 2-(1-cyclopropyl-2-methoxy-vinyl)-3-methyl-4-chloro-pyridine (6.41 g, 28.7 mmol) in acetic acid (50 mL) was treated with sulfuric acid (6.52 mL, 143 mmol) at room temperature overnight. The reaction mixture was neutralized with 2N NaOH to pH 8-9 extracted with ethyl acetate (2×100 mL). The organic phases were combined, dried, and concentrated. The residue was purified by flash silica column chromatography (hexane/ethyl acetate=2:1) to afford the title compound as a yellow solid (4.83 g, 80%). ESI-MS m/z: 210 (M+H)$^+$; $^1$H NMR (CDCl$_3$, 300 MHz) δ ppm: 9.89 (d, J=2.4 Hz, 1H), 8.35 (d, J=5.1 Hz, 1H), 7.26 (d, J=5.4 Hz, 1H), 3.26-3.28 (m, 1H), 2.35 (s, 3H), 1.53-1.59 (m, 1H), 0.55-0.79 (m, 2H), 0.25-0.39 (m, 2H).

Preparation of 2-[2-(3-methyl-4-chloro-pyridin-2-yl)-2-cyclopropyl-ethylidene]-malonic acid diethyl ester

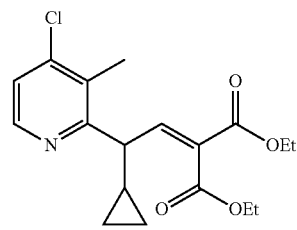 [SMILES: CCOC(=O)C(=CC(c1nccc(Cl)c1C)C1CC1)C(=O)OCC]

A mixture of (3-methyl-4-chloro-pyridin-2-yl)-cyclopropyl-acetaldehyde (4.83 g, 23.0 mmol), diethyl malonate (7.02 g, 43.8 mmol), piperidine (3.62 mL, 36.6 mmol), and acetic acid (4.19 mL, 73.2 mmol) in ethanol (100 mL) was heated to reflux overnight. The reaction mixture was concentrated to dryness. The residue was purified by flash silica column chromatography (hexane:ethyl acetate, 4:1) to afford the title compound as a yellow oil (5.76 g, 71%). ESI-MS m/z: 352 (M+H)$^+$.

Preparation of ethyl 8-chloro-1-cyclopropyl-9-methyl-4-oxo-4H-quinolizine-3-carboxylate

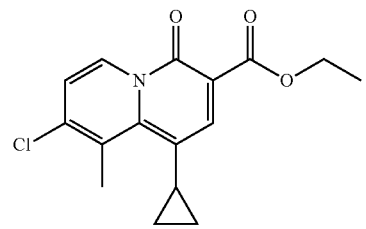 [SMILES: CCOC(=O)c1cc(C2CC2)c2c(C)c(Cl)ccn2c1=O]

A solution of 2-[2-(3-methyl-4-chloro-pyridin-2-yl)-2-cyclopropyl-ethylidene]-malonic acid diethyl ester (5.76 g, 16.4 mmol) in Dowtherm A (80 mL) was heated in a preheated oil bath at 230° C. for 15 min. The reaction mixture was cooled to room temperature and purified by flash silica column chromatography (hexane:ethyl acetate, 2:1 to 1:2) to afford the title compound as a yellow solid (3.76 g, 75%). ESI-MS m/z: 306 (M+H)$^+$; $^1$H NMR (CDCl$_3$, 300 MHz) δ ppm: 9.34 (d, J=7.8 Hz, 1H), 8.40 (s, 1H), 7.12 (d, J=7.8 Hz, 1H), 4.41 (q, 2H), 3.00 (s, 3H), 2.28-2.33 (m, 1H), 1.42 (t, 3H), 1.03-1.08 (m, 2H), 0.71-0.76 (m, 2H).

Preparation of scaffold B methyl 8-chloro-1-cyclopropyl-9-methyl-4-oxo-quinolizine-3-carboxylate Preparation of scaffold methyl 8-chloro-1-cyclopropyl-9-methyl-4-oxo-quinolizine-3-carboxylate

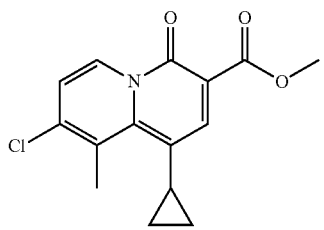 [SMILES: COC(=O)c1cc(C2CC2)c2c(C)c(Cl)ccn2c1=O]

Piperidine (7 mL, 70.9 mmol) and acetic acid (5.5 mL, 95 mmol) were added to a solution of 2-(3-methyl-4-chloro-pyridin-2-yl)-2-cyclopropyl-acetaldehyde (4.98 g, 23.75 mmol) in absolute ethanol (200 mL). Dimethyl malonate (16.44 mL, 144 mmol) was added and the reaction mixture was stirred at 100° C. for 5 h (the reaction mixture turned into a red solution). The solvent was evaporated under reduced pressure. The resulting mixture was diluted with ether (100 mL) and washed with water (100 mL) and brine (50 mL). The organic layer was separated and dried over sodium sulfate. The mixture was evaporated to dryness. Dowtherm A (110 mL) was added. This reaction mixture was heated to 240° C. under microwave irradiation and stirred at this temperature for 0.5 h during which the reaction mixture turned into a black solution. The residue was purified by reversed phase flash chromatography using a 5%-100% acetonitrile gradient in water with 1% TFA yielding the cyclized methyl ester (4 g, 51.4%). ESI-MS m/z: 292 (M+H)$^+$; $^1$H NMR (400 MHz, CDCl$_3$) δ ppm: 9.34 (d, J=7.8 Hz, 1H), 8.42 (s, 1H), 7.13 (d, J=7.8 Hz, 1H), 3.95 (s, 1H), 3.01 (s, 1H), 2.35-2.27 (m, 1H), 1.03-1.08 (m, 2H), 0.72-0.76 (m, 2H); $^{13}$C NMR (100 MHz CDCl$_3$) δ ppm 166.6, 155.4, 148.4, 145.5, 142.3, 130.7, 129.0, 117.6, 115.6, 105.4, 52.3, 19.6, 17.0, 9.9 (2CH2).

Preparation of Examples

Most of the examples were prepared according to the general procedures described below. The preparation of the other examples is otherwise reported specifically in the experimental section.

General Procedure A:

The quinolizine scaffold (1 eq.), boronate (1.3 eq.) and cesium carbonate (3 eq.) were added to a 3:1 mixture of 1,2-dimethoxyethane and water. The mixture was degassed with argon. 1,1'-Bis-diphenylphosphine ferrocene palladium (II) dichloride (0.1 eq.) was added and the mixture was heated at 90° C. under an argon atmosphere for 1 h. The reaction mixture was cooled. The mixture was diluted with CH$_2$Cl$_2$ (3 mL) and water was added (3 mL). The layers were separated using a phase separator and the aqueous layer was extracted with CH$_2$Cl$_2$ (2×5 mL). The combined organic layers were dried over sodium sulfate and concentrated in vacuo. The crude product was purified by flash silica column chromatography and dried in vacuo to afford the desired product.

General Procedure B:

The ester intermediate (1 eq.) was added to a solution of lithium hydroxide (2 eq.) in a 1:1 mixture of tetrahydrofuran and water. The reaction mixture was stirred for 18 h at 30° C. The mixture was acidified using 1M HCl in water. The precipitate was filtered off and dried in vacuo to afford the desired product.

General Procedure C:

The Boc-protected amine intermediate (1 eq.) was suspended in CH$_2$Cl$_2$ and 1 M HCl in diethyl ether (20 eq.) was added. The reaction mixture was stirred for 16 h. The precipitate was filtered off and dried in vacuo to afford the desired product.

General Procedure D:

The free acid (1 eq.) was added to a solution of potassium hydroxide (1.1 eq.) in water and stirred for 1 h. The solution was lyophilized to obtain the desired product.

Example 1

Preparation of ethyl 8-(4-amino-3-fluoro-phenyl)-1-cyclopropyl-7-fluoro-9-methyl-4-oxo-4H-quinolizine-3-carboxylate

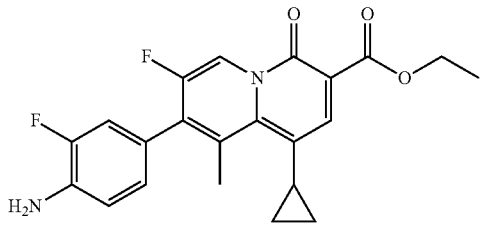 [SMILES: CCOC(=O)c1cc(C2CC2)c2c(C)c(-c3ccc(N)c(F)c3)c(F)cn2c1=O]

Ethyl 8-(4-amino-3-fluoro-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (149 mg, 0.46 mmol) and 2-fluoro-4-(4,4,5,5-tetramethyl-1,3,2-dioxaborolan-2-yl)-aniline (134 mg, 0.58 mmol). Purification by flash silica column chromatography (CH$_2$Cl$_2$:MeOH) (1:0 to 9:1) afforded the title compound as a yellow solid (18 mg, 10%). ESI-MS m/z: 399 (M+H)$^+$.

Preparation of EXAMPLE 1 8-(4-amino-3-fluoro-phenyl)-1-cyclopropyl-7-fluoro-9-methyl-4-oxo-4H-quinolizine-3-carboxylic acid

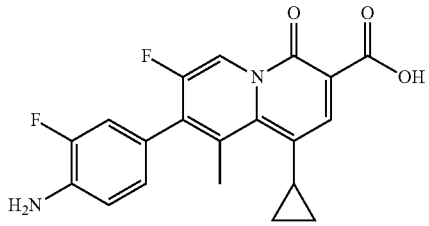

8-(4-Amino-3-fluoro-phenyl)-1-cyclopropyl-7-fluoro-9-methyl-4-oxo-4H-quinolizine-3-carboxylic acid was prepared according to General Procedure B using ethyl 8-(4-amino-3-fluoro-phenyl)-1-cyclopropyl-7-fluoro-9-methyl-4-oxo-4H-quinolizine-3-carboxylate (24 mg, 0.06 mmol) to afford the title compound EXAMPLE 1 as a yellow solid (19 mg, 85%). ESI-MS m/z: 371 (M+H)$^+$; $^1$H NMR (400 MHz, DMSO-d6) δ ppm: 13.99 (br s, 1H), 9.32 (s, 1H), 8.22 (s, 1H), 7.3-6.8 (m, 3H), 5.73 (s, 2H), 2.84 (s, 3H), 2.6-2.5 (m, 1H), 1.04-1.08 (m, 2H), 0.76-0.80 (m, 2H).

Preparation of potassium 8-(4-amino-3-fluoro-phenyl)-1-cyclopropyl-7-fluoro-9-methyl-4-oxo-4H-quinolizine-3-carboxylate

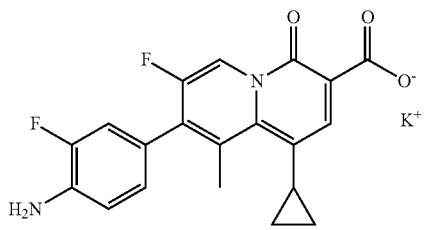

Potassium 8-(4-amino-3-fluorop-phenyl)-1-cyclopropyl-7-fluoro-9-methyl-4-oxo-4H-quinolizine-3-carboxylate was prepared according to General Procedure D using 8-(4-amino-3-fluoro-phenyl)-1-cyclopropyl-7-fluoro-9-methyl-4-oxo-4H-quinolizine-3-carboxylic acid (250 mg, 0.68 mmol) and potassium hydroxide to afford the title compound K salt of EXAMPLE 1 as a yellow solid (276 mg, 90%). ESI-MS m/z: 371 (M−K+ H)+.

Example 2

Preparation of methyl 8-(4-amino-3-fluoro-phenyl)-1-cyclopropyl-9-methyl-4-oxo-4H-quinolizine-3-carboxylate

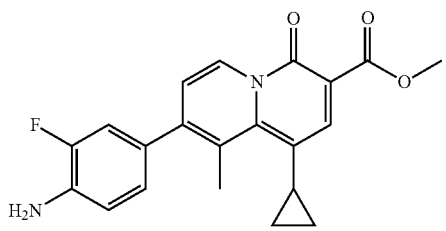

Methyl 8-(4-amino-3-fluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (200 mg, 0.68 mmol) and 2-fluoro-4-(4,4,5,5-tetramethyl-1,3,2-dioxaborolan-2-yl)aniline (195 mg, 0.82 mmol). Purification by flash silica column chromatography (CH$_2$Cl$_2$:MeOH) (1:0 to 9:1) afforded the title compound as a yellow solid (191 mg, 76%). ESI-MS m/z: 367 (M+H)+.

Preparation of EXAMPLE 2 8-(4-amino-3-fluoro-phenyl)-1-cyclopropyl-9-methyl-4-oxo-4H-quinolizine-3-carboxylic acid

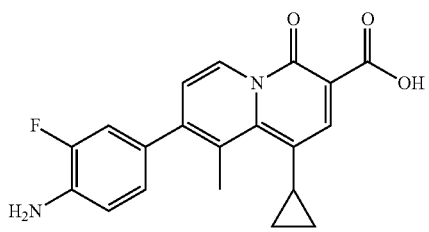 [SMILES: Cc1c(-c2ccc(N)c(F)c2)ccn2c(=O)c(C(=O)O)cc(C3CC3)c12]

8-(4-Amino-3-fluoro-phenyl)-1-cyclopropyl-9-methyl-4-oxo-4H-quinolizine-3-carboxylic acid was prepared according to General Procedure B using methyl 8-(4-amino-3-fluoro-phenyl)-1-cyclopropyl-9-methyl-4-oxo-4H-quinolizine-3-carboxylate (191 mg, 0.52 mmol) to afford the title compound EXAMPLE 2 as a yellow solid (135 mg, 73%). ESI-MS m/z: 353 (M+H)+; $^1$H NMR (400 MHz, DMSO-d6) δ ppm: 14.05 (br s, 1H), 9.55 (d, J=7.3 Hz, 1H), 8.21 (s, 1H), 7.57 (d, J=7.3 Hz, 1H), 7.16-7.34 (m, 2H), 6.92 (t, J=8.8 Hz, 1H), 5.74 (s, 2H), 2.89 (s, 3H), 2.50-2.70 (m, 1H), 1.02-1.05 (m, 2H), 0.73-0.80 (m, 2H).

Preparation of potassium 8-(4-amino-3-fluoro-phenyl)-1-cyclopropyl-9-methyl-4-oxo-4H-quinolizine-3-carboxylate

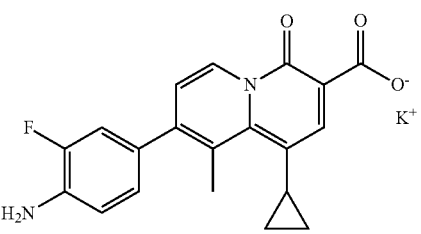 [SMILES: Cc1c(-c2ccc(N)c(F)c2)ccn2c(=O)c(C(=O)[O-])cc(C3CC3)c12 ; [K+]]

Potassium 8-(4-amino-3-fluoro-phenyl)-1-cyclopropyl-9-methyl-4-oxo-4H-quinolizine-3-carboxylate was prepared according to General Procedure D using 8-(4-amino-3-fluoro-phenyl)-1-cyclopropyl-9-methyl-4-oxo-4H-quinolizine-3-carboxylic acid (EXAMPLE 2) (260 mg, 0.74 mmol) to afford the title compound K salt of EXAMPLE 2 as a yellow solid (288 mg, 98%). ESI-MS m/z: 353 (M−K+ H)+.

Example 3

Preparation of methyl 8-(3-amino-phenyl)-1-cyclopropyl-9-methyl-4-oxo-4H-quinolizine-3-carboxylate

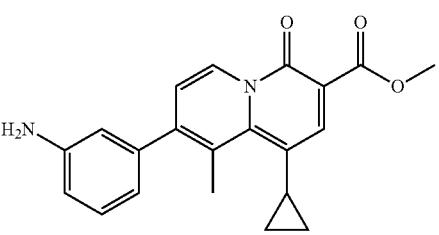 [SMILES: COC(=O)c1cc(C2CC2)c2c(C)c(-c3cccc(N)c3)ccn2c1=O]

Methyl 8-(3-amino-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (195 mg, 0.66 mmol) and (3-aminophenyl)-boronic acid (119 mg, 0.87 mmol). Purification by flash silica column chromatography (CH$_2$Cl$_2$:MeOH) (1:0 to 9:1) afforded the title compound as a yellow solid (91 mg, 39%). ESI-MS m/z: 349 (M+H)+.

Preparation of EXAMPLE 3 8-(3-amino-phenyl)-1-cyclopropyl-9-methyl-4-oxo-4H-quinolizine-3-carboxylic acid

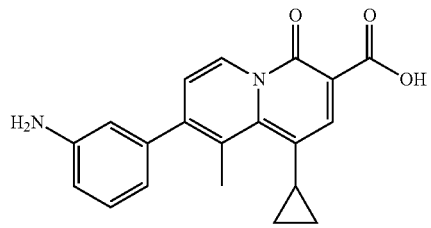 [SMILES: Cc1c(-c2cccc(N)c2)ccn2c(=O)c(C(=O)O)cc(C3CC3)c12]

8-(3-Amino-phenyl)-1-cyclopropyl-9-methyl-4-oxo-4H-quinolizine-3-carboxylic acid was prepared according to General Procedure B using methyl 8-(3-amino-phenyl)-1-cyclopropyl-9-methyl-4-oxo-4H-quinolizine-3-carboxylate (91 mg, 0.26 mmol) to afford the title compound EXAMPLE 3 as a yellow solid (62.4 mg, 72%). ESI-MS m/z: 335 (M+H)$^+$; $^1$H NMR (400 MHz, DMSO-d6) δ ppm: 14.20 (br s, 1H), 9.32 (d, J=7.3 Hz, 1H), 8.26 (s, 1H), 7.52 (d, J=7.3 Hz, 1H), 7.35-7.53 (m, 1H), 6.82-6.93 (m, 3H), 2.86 (s, 3H), 2.50-2.60 (m, 1H), 1.00-1.10 (m, 2H), 0.75-0.85 (m, 2H).

Preparation of EXAMPLE 4 8-(3-amino-phenyl)-1-cyclopropyl-7-fluoro-9-methyl-4-oxo-4H-quinolizine-3-carboxylic acid

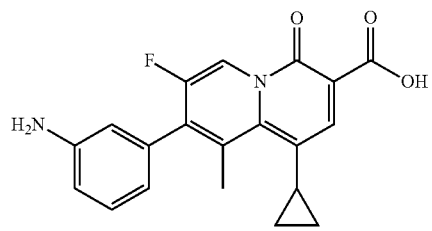

8-(3-Amino-phenyl)-1-cyclopropyl-7-fluoro-9-methyl-4-oxo-4H-quinolizine-3-carboxylic acid was prepared according to General Procedure B using ethyl 8-(3-amino-phenyl)-1-cyclopropyl-7-fluoro-9-methyl-4-oxo-4H-quinolizine-3-carboxylate (140 mg, 0.37 mmol) to afford the title compound EXAMPLE 4 as a yellow solid (30 mg, 25%). ESI-MS m/z: 353 (M+H)$^+$; $^1$H NMR (400 MHz, DMSO-d6) δ ppm: 9.35 (d, J=5.8 Hz, 1H), 8.25 (s, 1H), 7.22 (t, J=7.6 Hz, 1H), 6.71 (dd, J=1.6 Hz and J=8.1 Hz, 1H), 6.57 (s, 1H), 6.51 (d, J=7.6 Hz, 1H), 5.40 (br s, 2H), 2.82 (s, 3H), 2.53-2.63 (m, 1H), 1.04-1.07 (m, 2H), 0.76-0.78 (m, 2H).

Example 4

Preparation of ethyl 8-(3-amino-phenyl)-1-cyclopropyl-7-fluoro-9-methyl-4-oxo-4H-quinolizine-3-carboxylate

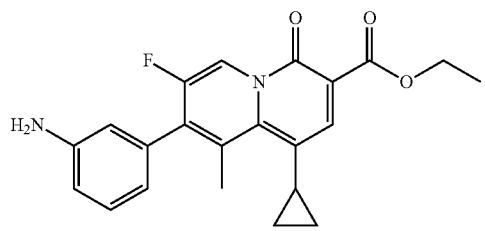 [SMILES: CCOC(=O)c1cc(C2CC2)c2c(C)c(-c3cccc(N)c3)c(F)cn2c1=O]

Ethyl 8-(3-amino-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (102.5 mg, 0.32 mmol) and (3-amino-phenyl)-boronic acid (54.8 mg, 0.40 mmol). Purification by flash silica column chromatography (CH$_2$Cl$_2$:MeOH) (1:0 to 9:1) afforded the title compound as a yellow solid (30 mg, 25%). ESI-MS m/z: 381 (M+H)$^+$.

Example 5

Preparation of ethyl 8-(4-amino-phenyl)-1-cyclopropyl-7-fluoro-9-methyl-4-oxo-4H-quinolizine-3-carboxylate

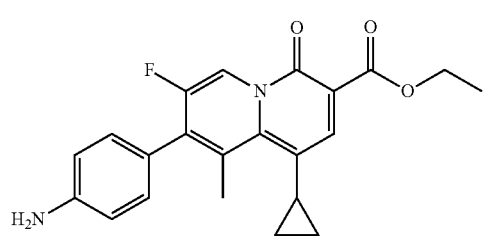 [SMILES: CCOC(=O)c1cc(C2CC2)c2c(C)c(-c3ccc(N)cc3)c(F)cn2c1=O]

Ethyl 8-(4-amino-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (500 mg, 1.54 mmol) and 4-(4,4,5,5-tetramethyl-1,3,2-dioxaborolan-2-yl)-aniline (439 mg, 2.00 mmol). Purification by flash silica column chromatography (CH$_2$Cl$_2$:MeOH) (1:0 to 9:1) afforded the title compound as a yellow solid (550 mg, 93%). ESI-MS m/z: 381 (M+H)$^+$.

Preparation of EXAMPLE 5 8-(4-amino-phenyl)-1-cyclopropyl-7-fluoro-9-methyl-4-oxo-4H-quinolizine-3-carboxylic acid

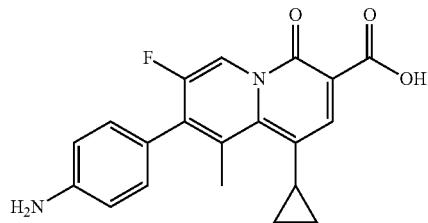 [SMILES: Cc1c(-c2ccc(N)cc2)c(F)cn2c(=O)c(C(=O)O)cc(C3CC3)c12]

8-(4-Amino-phenyl)-1-cyclopropyl-7-fluoro-9-methyl-4-oxo-4H-quinolizine-3-carboxylic acid was prepared according to General Procedure B using ethyl 8-(4-amino-phenyl)-1-cyclopropyl-7-fluoro-9-methyl-4-oxo-4H-quinolizine-3-carboxylate (550 mg, 1.45 mmol) to afford the title compound EXAMPLE 5 as a yellow solid (435 mg, 85%). ESI-MS m/z: 353 (M+H)$^+$; $^1$H NMR (400 MHz, DMSO-d6) δ ppm: 13.95-14.02 (m, 1H), 9.32 (d, J=5.8 Hz, 1H), 8.21 (s, 1H), 7.21 (d, J=6.8 Hz, 2H), 6.79 (d, J=8.3 Hz, 2H), 2.85 (s, 3H), 2.50-2.60 (m, 1H), 1.05-1.07 (m, 2H), 0.76-0.78 (m, 2H).

Preparation of potassium 8-(4-amino-phenyl)-1-cyclopropyl-7-fluoro-9-methyl-4-oxo-4H-quinolizine-3-carboxylate

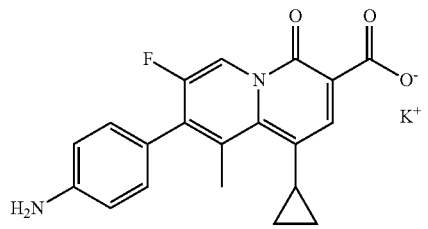

Potassium 8-(4-amino-phenyl)-1-cyclopropyl-7-fluoro-9-methyl-4-oxo-4H-quinolizine-3-carboxylate was prepared according to General Procedure D using 8-(4-amino-phenyl)-1-cyclopropyl-7-fluoro-9-methyl-4-oxo-4H-quinolizine-3-carboxylic acid (460 mg, 0.74 mmol) to afford the title compound K salt of EXAMPLE 5 as a yellow solid (510 mg, 100%). ESI-MS m/z: 353 (M−K$^+$ H)$^+$.

Example 6

Preparation of ethyl 8-(4-carbamoyl-phenyl)-1-cyclopropyl-7-fluoro-9-methyl-4-oxo-4H-quinolizine-3-carboxylate

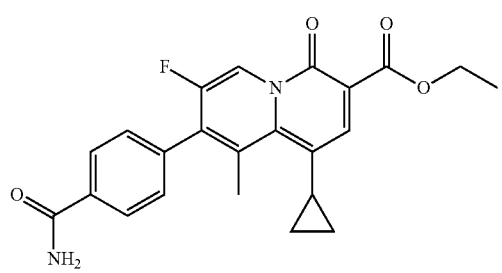 [SMILES: CCOC(=O)c1cc(C2CC2)c2c(C)c(-c3ccc(C(N)=O)cc3)c(F)cn2c1=O]

Ethyl 8-(4-carbamoyl-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (500 mg, 1.54 mmol) and (4-carbamoyl-phenyl)-boronic acid (305.7 mg, 1.85 mmol). Purification by flash silica column chromatography (CH$_2$Cl$_2$:MeOH) (1:0 to 9:1) afforded the title compound as a yellow solid (540 mg, 85%). ESI-MS m/z: 409 (M+H)$^+$, 453 (M+HCOO)$^-$.

Preparation of EXAMPLE 6 8-(4-carbamoyl-phenyl)-1-cyclopropyl-7-fluoro-9-methyl-4-oxo-4H-quinolizine-3-carboxylic acid

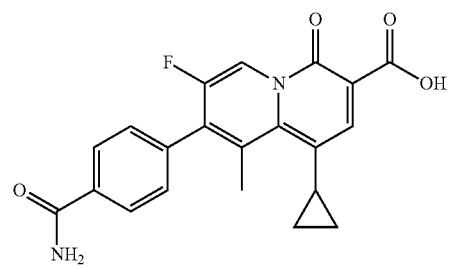 [SMILES: Cc1c(-c2ccc(C(N)=O)cc2)c(F)cn2c(=O)c(C(=O)O)cc(C3CC3)c12]

8-(4-Carbamoyl-phenyl)-1-cyclopropyl-7-fluoro-9-methyl-4-oxo-4H-quinolizine-3-carboxylic acid was prepared according to General Procedure B using ethyl 8-(4-carbamoyl-phenyl)-1-cyclopropyl-7-fluoro-9-methyl-4-oxo-4H-quinolizine-3-carboxylate (540 mg, 1.32 mmol) and reacted for 10 days at 30° C. to afford the title compound EXAMPLE 6 as a yellow solid: (360 mg, 71%). ESI-MS m/z: 381 (M+H)$^+$; $^1$H NMR (400 MHz, DMSO-d6) δ ppm: 13.94 (s, 1H), 9.42 (d, J=5.6 Hz, 1H), 8.28 (s, 1H), 8.16 (s, 1H), 8.08 (d, J=8.1 Hz, 2H), 7.57-7.60 (m, 3H), 2.80 (s, 3H), 2.50-2.60 (m, 1H), 1.06-1.08 (m, 2H), 0.76-0.80 (m, 2H).

Preparation of potassium 8-(4-carbamoyl-phenyl)-1-cyclopropyl-7-fluoro-9-methyl-4-oxo-4H-quinolizine-3-carboxylate

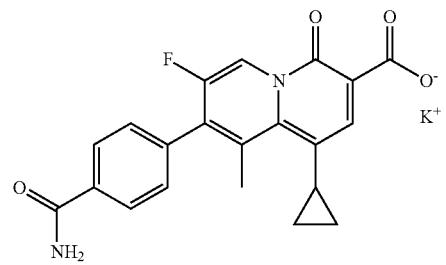 [SMILES: Cc1c(-c2ccc(C(N)=O)cc2)c(F)cn2c(=O)c(C(=O)[O-])cc(C3CC3)c12 ; [K+]]

Potassium 8-(4-carbamoyl-phenyl)-1-cyclopropyl-7-fluoro-9-methyl-4-oxo-4H-quinolizine-3-carboxylate was prepared according to General Procedure D using 8-(4-carbamoyl-phenyl)-1-cyclopropyl-7-fluoro-9-methyl-4-oxo-4H-quinolizine-3-carboxylic acid (310 mg, 0.82 mmol) to afford the title compound K salt of EXAMPLE 6 as a yellow solid (345 mg, 100%). ESI-MS m/z: 381 (M−K$^+$ H)$^+$.

Example 7

Preparation of methyl 8-(4-amino-2-fluoro-phenyl)-1-cyclopropyl-9-methyl-4-oxo-4H-quinolizine-3-carboxylate

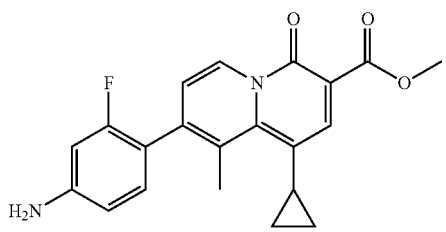 [SMILES: COC(=O)c1cc(C2CC2)c2c(C)c(-c3ccc(N)cc3F)ccn2c1=O]

Methyl 8-(4-amino-2-fluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 3-fluoro-4-(4,4,5,5-tetramethyl-1,3,2-dioxaborolan-2-yl)-aniline (122 mg, 0.51 mmol). Purification by flash silica column chromatography (CH$_2$Cl$_2$:MeOH) (1:0 to 94:6) afforded the title compound as a yellow solid (87 mg, 64%). ESI-MS m/z: 367 (M+H)$^+$.

Preparation of EXAMPLE 7 8-(4-amino-2-fluoro-phenyl)-1-cyclopropyl-9-methyl-4-oxo-4H-quinolizine-3-carboxylic acid

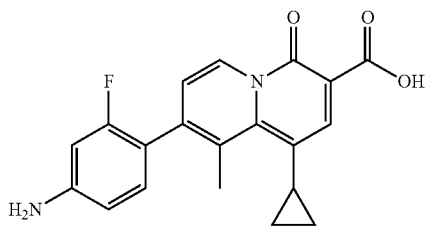 [SMILES: Cc1c(-c2ccc(N)cc2F)ccn2c(=O)c(C(=O)O)cc(C3CC3)c12]

8-(4-Amino-2-fluoro-phenyl)-1-cyclopropyl-9-methyl-4-oxo-4H-quinolizine-3-carboxylic acid was prepared according to General Procedure B using methyl 8-(4-amino-2-fluoro-phenyl)-1-cyclopropyl-9-methyl-4-oxo-4H-quinolizine-3-carboxylate (87 mg, 0.24 mmol) to afford the title compound EXAMPLE 7 as a yellow solid (50 mg, 59%). ESI-MS m/z: 353 (M+H)$^+$; $^1$H NMR (400 MHz, DMSO-d6) δ ppm: 9.27 (d, J=7.3 Hz, 1H), 8.27 (s, 1H), 7.48 (s, 1H), 7.18 (t, J=8.6 Hz, 1H), 6.57 (dd, J=8.3 Hz, J=1.8 Hz, 1H), 6.49 (dd, J=13.4 Hz, J=1.8 Hz, 1H), 5.92 (s, 2H), 2.80 (s, 3H), 2.40-2.60 (m, 1H), 1.03-1.06 (m, 2H), 0.70-0.72 (m, 2H).

Example 8

Preparation of methyl 8-(3-amino-4-fluoro-phenyl)-1-cyclopropyl-9-methyl-4-oxo-4H-quinolizine-3-carboxylate

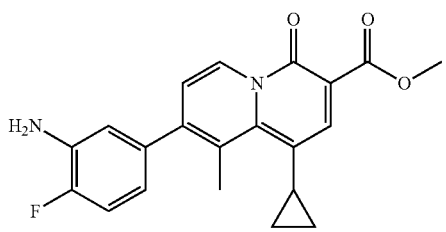 [SMILES: COC(=O)c1cc(C2CC2)c2c(C)c(-c3ccc(F)c(N)c3)ccn2c1=O]

Methyl 8-(3-amino-4-fluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 2-fluoro-5-(4,4,5,5-tetramethyl-1,3,2-dioxaborolan-2-yl)-aniline (122 mg, 0.51 mmol). Purification by flash silica column chromatography (CH$_2$Cl$_2$:MeOH) (1:0 to 94:6) afforded the title compound as a yellow solid (128 mg, 98%). ESI-MS m/z: 367 (M+H)$^+$.

Preparation of EXAMPLE 8 8-(3-amino-4-fluoro-phenyl)-1-cyclopropyl-9-methyl-4-oxo-4H-quinolizine-3-carboxylic acid

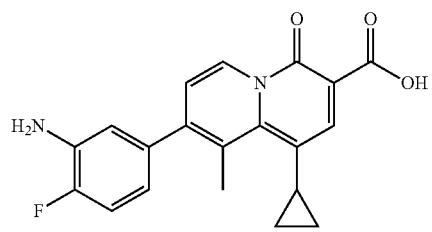 [SMILES: Cc1c(-c2ccc(F)c(N)c2)ccn2c(=O)c(C(=O)O)cc(C3CC3)c12]

8-(3-Amino-4-fluoro-phenyl)-1-cyclopropyl-9-methyl-4-oxo-4H-quinolizine-3-carboxylic acid was prepared according to General Procedure B using methyl 8-(3-amino-4-fluorophenyl)-1-cyclopropyl-9-methyl-4-oxo-4H-quinolizine-3-carboxylate (123 mg, 0.35 mmol) to afford the title compound EXAMPLE 8 as a yellow solid (EXAMPLE 8) (60 mg, 49%). ESI-MS m/z: 353 (M+H)$^+$; $^1$H NMR (400 MHz, DMSO-d6) δ ppm: 9.31 (d, J=7.3 Hz, 1H), 8.26 (s, 1H), 7.50 (d, J=7.3 Hz, 1H), 7.18 (dd, J=8.3 Hz, J=11.4 Hz, 1H), 6.89 (dd, J=2.0 Hz, J=8.6 Hz, 1H), 6.63-6.67 (m, 1H), 5.44 (s, 2H), 2.85 (s, 3H), 2.40-2.54 (m, 1H), 1.04-1.07 (m, 2H), 0.76-0.78 (m, 2H).

Example 9

Preparation of methyl 8-(3-amino-5-fluoro-phenyl)-1-cyclopropyl-9-methyl-4-oxo-4H-quinolizine-3-carboxylate

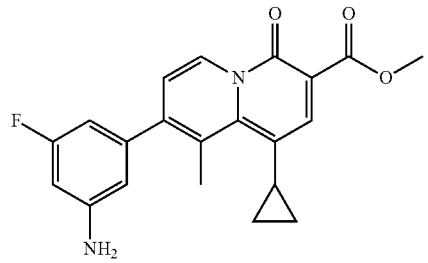 [SMILES: COC(=O)c1cc(C2CC2)c2c(C)c(-c3cc(N)cc(F)c3)ccn2c1=O]

Methyl 8-(3-amino-5-fluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 3-amino-5-fluoro-phenyl-boronic acid (80 mg, 0.51 mmol). Purification by flash silica column chromatography (CH$_2$Cl$_2$:MeOH) (1:0 to 94:6) afforded the title compound as a yellow solid (108 mg, 81%). ESI-MS m/z: 367 (M+H)$^+$.

Preparation of EXAMPLE 9 8-(3-amino-5-fluoro-phenyl)-1-cyclopropyl-9-methyl-4-oxo-4H-quinolizine-3-carboxylic acid

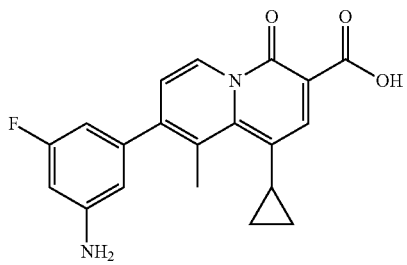 [SMILES: Cc1c(-c2cc(N)cc(F)c2)ccn2c(=O)c(C(=O)O)cc(C3CC3)c12]

8-(3-Amino-5-fluoro-phenyl)-1-cyclopropyl-9-methyl-4-oxo-4H-quinolizine-3-carboxylic acid was prepared according to General Procedure B using methyl 8-(3-amino-5-fluorophenyl)-1-cyclopropyl-9-methyl-4-oxo-4H-quinolizine-3-carboxylate (108 mg, 0.29 mmol) to afford the title compound EXAMPLE 9 as a yellow solid (69 mg, 67%). ESI-MS m/z: 353 (M+H)+; 1H NMR (400 MHz, DMSO-d6) δ ppm: 9.22 (d, J=7.3 Hz, 1H), 8.48 (s, 1H), 7.19 (d, J=7.6 Hz, 1H), 6.36-6.44 (m, 3H), 6.68 (s, 2H), 2.81 (s, 3H), 2.40-2.50 (m, 1H), 1.02-1.04 (m, 2H), 0.70-0.72 (m, 2H).

Example 10

Preparation of methyl 1-cyclopropyl-8-(3-fluoro-phenyl)-9-methyl-4-oxo-4H-quinolizine-3-carboxylate

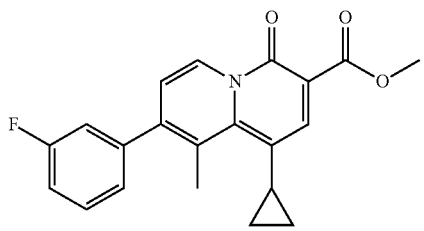 [SMILES: COC(=O)c1cc(C2CC2)c2c(C)c(-c3cccc(F)c3)ccn2c1=O]

Methyl 1-cyclopropyl-8-(3-fluoro-phenyl)-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 3-fluoro-phenyl-boronic acid (71 mg, 0.51 mmol). Purification by flash silica column chromatography (CH2Cl2:MeOH) (1:0 to 94:6) afforded the title compound as a yellow solid (96 mg, 77%). ESI-MS m/z: 352 (M+H)+.

Preparation of EXAMPLE 10 1-cyclopropyl-8-(3-fluoro-phenyl)-9-methyl-4-oxo-4H-quinolizine-3-carboxylic acid

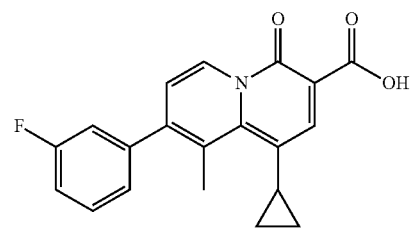

1-Cyclopropyl-8-(3-fluoro-phenyl)-9-methyl-4-oxo-4H-quinolizine-3-carboxylic acid was prepared according to General Procedure B using methyl 1-cyclopropyl-8-(3-fluoro-phenyl)-9-methyl-4-oxo-4H-quinolizine-3-carboxylate (96 mg, 0.27 mmol) to afford the title compound EXAMPLE 10 as a yellow solid (21 mg, 23%). ESI-MS m/z: 338 (M+H)+; 1H NMR (400 MHz, DMSO-d6) δ ppm: 9.34 (d, J=7.3 Hz, 1H), 8.28 (s, 1H), 7.57-7.65 (m, 2H), 7.39-7.47 (m, 3H), 2.86 (s, 3H), 2.40-2.50 (m, 1H), 1.07-1.09 (m, 2H), 0.80-0.82 (m, 2H).

Example 11

Preparation of methyl 8-(4-amino-3-chloro-phenyl)-1-cyclopropyl-9-methyl-4-oxo-4H-quinolizine-3-carboxylate

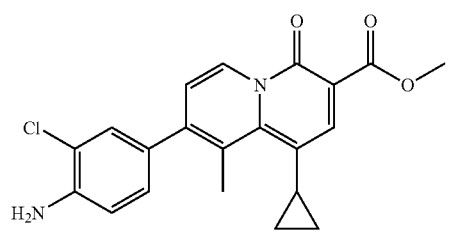

Methyl 8-(4-amino-3-chloro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (76 mg, 0.26 mmol) and 2-chloro-4-(4,4,5,5-tetramethyl-1,3,2-dioxaborolan-2-yl)-aniline (78 mg, 0.31 mmol). Purification by flash silica column chromatography (CH2Cl2:MeOH) (1:0 to 94:6) afforded the title compound as a yellow solid (63 mg, 62%). ESI-MS m/z: 387 (M+H)+.

Preparation of EXAMPLE 11 8-(4-amino-3-chloro-phenyl)-1-cyclopropyl-9-methyl-4-oxo-4H-quinolizine-3-carboxylic acid

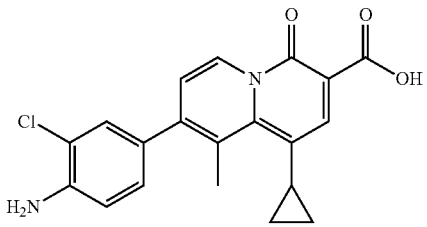 [SMILES: Cc1c(-c2ccc(N)c(Cl)c2)ccn2c(=O)c(C(=O)O)cc(C3CC3)c12]

8-(4-Amino-3-chloro-phenyl)-1-cyclopropyl-9-methyl-4-oxo-4H-quinolizine-3-carboxylic acid was prepared according to General Procedure B using methyl 8-(4-amino-3-chloro-phenyl)-1-cyclopropyl-9-methyl-4-oxo-4H-quinolizine-3-carboxylate (63 mg, 0.16 mmol) to afford the title compound EXAMPLE 11 as a yellow solid (37 mg, 62%). ESI-MS m/z: 369 (M+H)$^+$; $^1$H NMR (400 MHz, DMSO-d6) δ ppm: 9.21 (d, J=7.3 Hz, 1H), 8.38 (s, 1H), 7.43 (s, 1H), 7.30 (s, 1H), 7.26 (d, J=14.5 Hz, 1H), 6.94 (d, J=8.3 Hz, 1H), 5.82 (s, 2H), 2.85 (s, 3H), 2.40-2.50 (m, 1H), 1.04-1.06 (m, 2H), 0.72-0.74 (m, 2H).

Example 12

Preparation of methyl 8-(4-amino-3-methoxy-phenyl)-1-cyclopropyl-9-methyl-4-oxo-4H-quinolizine-3-carboxylate

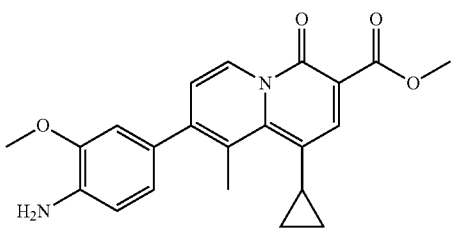

Methyl 8-(4-amino-3-methoxy-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (76 mg, 0.26 mmol) and 2-methoxy-4-(4,4,5,5-tetramethyl-1,3,2-dioxaborolan-2-yl)-aniline (78 mg, 0.31 mmol). Purification by flash silica column chromatography (CH$_2$Cl$_2$:MeOH) (1:0 to 94:6) afforded the title compound as a yellow solid (41 mg, 40%). ESI-MS m/z: 379 (M+H)$^+$.

Preparation of EXAMPLE 12 8-(4-amino-3-methoxy-phenyl)-1-cyclopropyl-9-methyl-4-oxo-4H-quinolizine-3-carboxylic acid

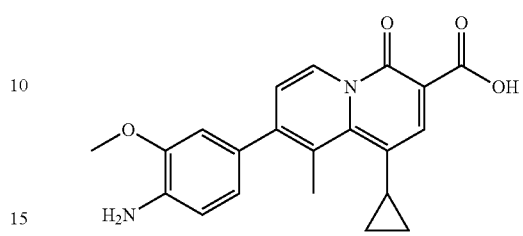

8-(4-Amino-3-methoxy-phenyl)-1-cyclopropyl-9-methyl-4-oxo-4H-quinolizine-3-carboxylic acid was prepared according to General Procedure B using methyl 8-(4-amino-3-methoxy-phenyl)-1-cyclopropyl-9-methyl-4-oxo-4H-quinolizine-3-carboxylate (41 mg, 0.11 mmol) to afford the title compound EXAMPLE 12 as a yellow solid (29 mg, 92%). ESI-MS m/z: 365 (M+H)$^+$; $^1$H NMR (400 MHz, DMSO-d6) δ ppm: 9.27 (d, J=7.3 Hz, 1H), 8.19 (s, 1H), 7.43 (d, J=7.3 Hz, 1H), 7.03 (s, 1H), 6.99 (dd, J=1.8 Hz, J=8.1 Hz, 1H), 6.80 (d, J=8.1 Hz, 1H), 5.38 (s, 2H), 3.86 (s, 3H), 2.92 (s, 3H), 2.40-2.54 (m, 1H), 1.06-1.10 (m, 2H), 0.76-0.80 (m, 2H).

Example 13

Preparation of methyl 8-(4-acetamido-phenyl)-1-cyclopropyl-9-methyl-4-oxo-4H-quinolizine-3-carboxylate

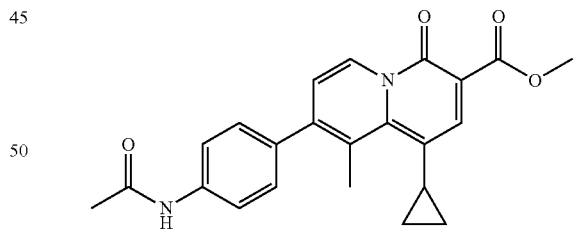

Methyl 8-(4-acetamido-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (77 mg, 0.26 mmol) and (4-acetamido-phenyl)-boronic acid (56 mg, 0.31 mmol). Purification by flash silica column chromatography (CH$_2$Cl$_2$:MeOH) (1:0 to 94:6) afforded the title compound as a yellow solid (93 mg, 90%). ESI-MS m/z: 391 (M+H)$^+$.

Preparation of EXAMPLE 13 8-(4-acetamido-phenyl)-1-cyclopropyl-9-methyl-4-oxo-4H-quinolizine-3-carboxylic acid

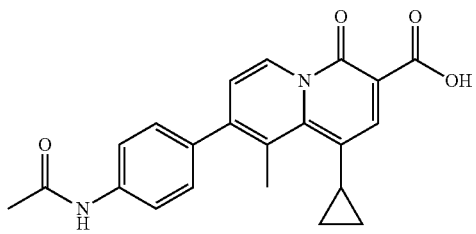 [SMILES: CC(=O)Nc1ccc(-c2ccn3c(=O)c(C(=O)O)cc(C4CC4)c3c2C)cc1]

8-(4-Acetamido-phenyl)-1-cyclopropyl-9-methyl-4-oxo-4H-quinolizine-3-carboxylic acid was prepared according to General Procedure: using methyl 8-(4-acetamido-phenyl)-1-cyclopropyl-9-methyl-4-oxo-4H-quinolizine-3-carboxylate (93 mg, 0.24 mmol) to afford the title compound EXAMPLE 13 as a yellow solid (45 mg, 50%). ESI-MS m/z: 377 (M+H)$^+$; 1H NMR (400 MHz, DMSO-d6) δ ppm: 10.20 (s, 1H), 9.32 (d, J=7.3 Hz, 1H), 8.25 (s, 1H), 7.79 (d, J=8.4 Hz, 2H), 7.58 (d, J=7.3 Hz, 1H), 7.53 (d, J=8.1 Hz, 2H), 2.88 (s, 3H), 2.40-2.54 (m, 1H), 2.10 (s, 3H), 1.07-1.09 (m, 2H), 0.77-0.79 (m, 2H).

Example 14

Preparation of methyl 1-cyclopropyl-9-methyl-8-(4-(methylsulfonamido)-phenyl)-4-oxo-4H-quinolizine-3-carboxylate

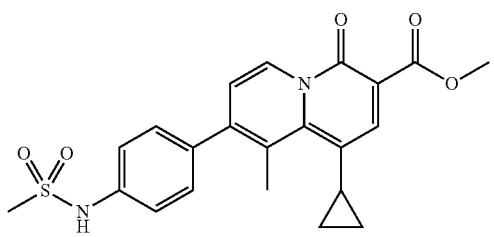

Methyl 1-cyclopropyl-9-methyl-8-(4-(methylsulfonamido)-phenyl)-4-oxo-4H-quinolizine-3-carboxylate was prepared according to General Procedure A using methyl 8-chloro-1-cyclopropyl-9-methyl-4-oxo-4H-quinolizine-3-carboxylate (74 mg, 0.25 mmol) and N-(4-(4,4,5,5-tetramethyl-1,3,2-dioxaborolan-2-yl)-phenyl)-methane-sulfonamide (96 mg, 0.32 mmol). Compound precipitated from solution and was filtered off and dried in vacuo to afford the title compound as a yellow solid (83 mg, 77%). ESI-MS m/z: 427 (M+H)$^+$.

Preparation of EXAMPLE 14 1-cyclopropyl-9-methyl-8-(4-(methylsulfonamido)-phenyl)-4-oxo-4H-quinolizine-3-carboxylic acid

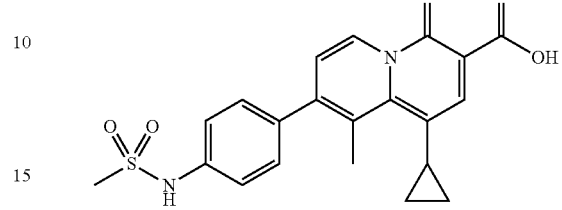

1-Cyclopropyl-9-methyl-8-(4-(methylsulfonamido)-phenyl)-4-oxo-4H-quinolizine-3-carboxylic acid was prepared according to General Procedure B using methyl 1-cyclopropyl-9-methyl-8-(4-(methylsulfonamido)-phenyl)-4-oxo-4H-quinolizine-3-carboxylate (83 mg, 0.20 mmol) to afford the title compound EXAMPLE 14 as a yellow solid (53 mg, 64%). ESI-MS m/z: 413 (M+H)$^+$; $^1$H NMR (400 MHz, DMSO-d6) δ ppm: 10.1 (s, 1H), 9.33 (d, J=7.3 Hz, 1H), 8.26 (s, 1H), 7.55-7.58 (m, 3H), 7.39 (d, J=8.6 Hz, 2H), 3.11 (s, 3H), 2.88 (s, 3H), 2.40-2.55 (m, 1H), 1.06-1.09 (m, 2H), 0.78-0.80 (m, 2H).

Example 15

Preparation of methyl 1-cyclopropyl-9-methyl-8-(4-(methylamino)-phenyl)-4-oxo-4H-quinolizine-3-carboxylate

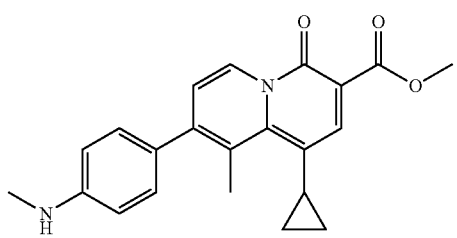

Methyl 1-cyclopropyl-9-methyl-8-(4-(methylamino)-phenyl)-4-oxo-4H-quinolizine-3-carboxylate was prepared according to General Procedure A using methyl 8-chloro-1-cyclopropyl-9-methyl-4-oxo-4H-quinolizine-3-carboxylate (74 mg, 0.25 mmol) and N-methyl-4-(4,4,5,5-tetramethyl-1,3,2-dioxaborolan-2-yl)-aniline (71 mg, 0.31 mmol). Purification by flash silica column chromatography (CH$_2$Cl$_2$:MeOH) (1:0 to 94:6) afforded the title compound as a yellow solid (81 mg, 81%). ESI-MS m/z: 363 (M+H)$^+$.

Preparation of EXAMPLE 15 1-cyclopropyl-9-methyl-8-(4-(methylamino)-phenyl)-4-oxo-4H-quinolizine-3-carboxylic acid

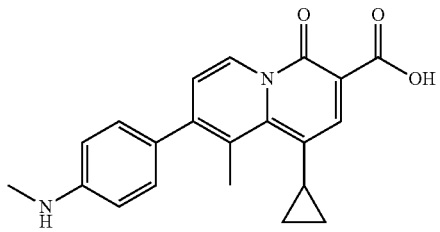 [SMILES: CNc1ccc(-c2ccn3c(=O)c(C(=O)O)cc(C4CC4)c3c2C)cc1]

1-Cyclopropyl-9-methyl-8-(4-(methylamino)-phenyl)-4-oxo-4H-quinolizine-3-carboxylic acid was prepared according to General Procedure B using methyl 1-cyclopropyl-9-methyl-8-(4-(methylamino)-phenyl)-4-oxo-4H-quinolizine-3-carboxylate (81 mg, 0.22 mmol) to afford the title compound EXAMPLE 15 as a yellow solid (55 mg, 72%). ESI-MS m/z: 349 (M+H)$^+$; $^1$H NMR (400 MHz, DMSO-d6) δ ppm: 9.27 (d, J=7.3 Hz, 1H), 8.20 (s, 1H), 9.59 (d, J=7.3 Hz, 1H), 7.39 (d, J=8.6 Hz, 2H), 6.70 (d, J=8.6 Hz, 2H), 6.28 (d, J=5.1 Hz, 1H), 2.90 (s, 3H), 2.76 (d, J=4.8 Hz, 3H), 2.40-2.52 (m, 1H), 1.06-1.08 (m, 2H), 0.75-0.77 (m, 2H).

Example 16

Preparation of methyl 1-cyclopropyl-9-methyl-4-oxo-8-(pyridin-4-yl)-4H-quinolizine-3-carboxylate

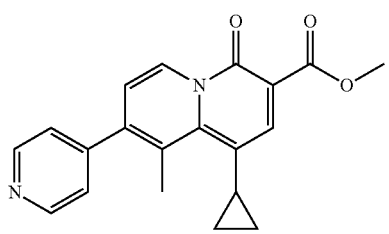 [SMILES: COC(=O)c1cc(C2CC2)c2c(C)c(-c3ccncc3)ccn2c1=O]

Methyl 1-cyclopropyl-9-methyl-4-oxo-8-(pyridin-4-yl)-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and pyridin-4-yl-boronic acid (253 mg, 2.05 mmol). Purification by flash silica column chromatography (CH$_2$Cl$_2$:MeOH) (1:0 to 9:1) afforded the title compound as a yellow solid (400 mg, 69%). ESI-MS m/z: 373 (M+K)$^+$, 357 (M+Na)$^+$, 335 (M+H)$^+$.

Preparation of EXAMPLE 16 1-cyclopropyl-9-methyl-4-oxo-8-(pyridin-4-yl)-4H-quinolizine-3-carboxylic acid

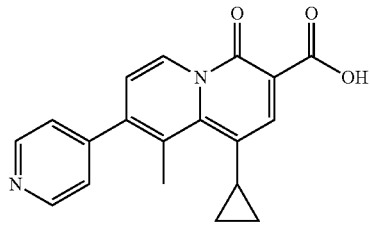 [SMILES: Cc1c(-c2ccncc2)ccn2c(=O)c(C(=O)O)cc(C3CC3)c12]

1-Cyclopropyl-9-methyl-4-oxo-8-(pyridin-4-yl)-4H-quinolizine-3-carboxylic acid was prepared according to General Procedure B using methyl 1-cyclopropyl-9-methyl-4-oxo-8-(pyridin-4-yl)-4H-quinolizine-3-carboxylate (400 mg, 1.20 mmol) to afford the title compound EXAMPLE 16 as a yellow solid (262 mg, 68%). ESI-MS m/z: 321 (M+H)$^+$; 1H NMR (400 MHz, DMSO-d6) δ ppm: 14.05 (s, 1H), 9.36 (d, J=7.3 Hz, 1H), 8.79 (d, J=5.8 Hz, 2H), 8.30 (s, 1H), 7.55-7.59 (m, 3H), 2.83 s, (3H), 2.50-2.60 (m, 1H), 1.05-1.10 (m, 2H), 0.79-0.84 (m, 2H).

Preparation of potassium 1-cyclopropyl-9-methyl-4-oxo-8-(pyridin-4-yl)-4H-quinolizine-3-carboxylate

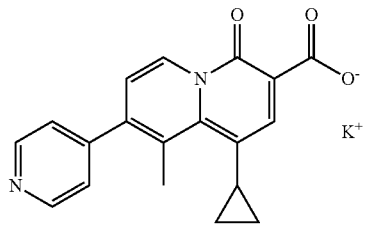 [SMILES: Cc1c(-c2ccncc2)ccn2c(=O)c(C(=O)[O-])cc(C3CC3)c12 ; [K+]]

Potassium 1-cyclopropyl-9-methyl-4-oxo-8-(pyridin-4-yl)-4H-quinolizine-3-carboxylate was prepared according to General Procedure D using 1-cyclopropyl-9-methyl-4-oxo-8-(pyridin-4-yl)-4H-quinolizine-3-carboxylic acid (EXAMPLE 16) (250 mg, 0.78 mmol) to afford the K salt of title compound EXAMPLE 16 as a yellow solid (290 mg, 100%). ESI-MS m/z: 321 (M−K$^+$H)$^+$; $^1$H NMR (400 MHz, CD$_3$OD) δ ppm: 9.43 (d, J=7.3 Hz, 1H), 8.72 (d, J=5.8 Hz, 2H), 8.62 (s, 1H), 7.58 (d, J=5.8 Hz, 2H), 7.20 (d, J=3.6 Hz, 2H), 2.87 (s, 3H), 2.46-2.53 (m, 1H), 0.80-1.10 (m, 2H), 0.84-0.86 (m, 2H).

Example 17

Preparation of methyl 1-cyclopropyl-9-methyl-4-oxo-8-(pyridin-3-yl)-4H-quinolizine-3-carboxylate

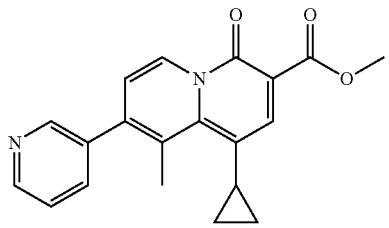 [SMILES: COC(=O)c1cc(C2CC2)c2c(C)c(-c3cccnc3)ccn2c1=O]

Methyl 1-cyclopropyl-9-methyl-4-oxo-8-(pyridin-3-yl)-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and pyridin-3-ylboronic acid (63 mg, 0.51 mmol). Purification by flash silica column chromatography ($CH_2Cl_2$:MeOH) (1:0 to 94:6) afforded the title compound as a yellow solid (100 mg, 87%). ESI-MS m/z: 335 (M+H)$^+$.

Preparation of EXAMPLE 17 1-cyclopropyl-9-methyl-4-oxo-8-(pyridin-3-yl)-4H-quinolizine-3-carboxylic acid

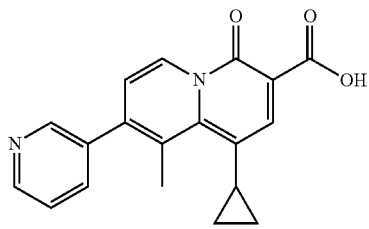

1-Cyclopropyl-9-methyl-4-oxo-8-(pyridin-3-yl)-4H-quinolizine-3-carboxylic acid was prepared according to General Procedure B using methyl 1-cyclopropyl-9-methyl-4-oxo-8-(pyridin-3-yl)-4H-quinolizine-3-carboxylate (100 mg, 0.30 mmol) to afford the title compound EXAMPLE 17 as a yellow solid (84 mg, 87%). ESI-MS m/z: 321 (M+H)$^+$; $^1$H NMR (400 MHz, DMSO-d6) δ ppm: 9.35 (d, J=7.3 Hz, 1H), 8.73-8.78 (s, 2H), 8.28 (s, 1H), 8.02-8.05 (m, 1H), 7.61-7.65 (m, 2H), 2.86 (s, 3H), 2.40-2.54 (m, 1H), 1.06-1.10 (m, 2H), 0.80-0.83 (m, 2H).

Example 18

Preparation of methyl 8-(4-amino-phenyl)-1-cyclopropyl-9-methyl-4-oxo-4H-quinolizine-3-carboxylate

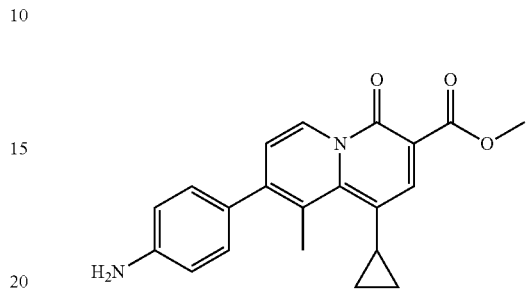

Methyl 8-(4-amino-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (150 mg, 0.51 mmol) and 4-(4,4,5,5-tetramethyl-1,3,2-dioxaborolan-2-yl)-aniline (135 mg, 0.62 mmol). Purification by flash silica column chromatography ($CH_2Cl_2$:MeOH) (1:0 to 9:1) afforded the title compound as a yellow solid (25 mg, 14%). ESI-MS m/z: 349 (M+H)$^+$.

Preparation of EXAMPLE 18 8-(4-amino-phenyl)-1-cyclopropyl-9-methyl-4-oxo-4H-quinolizine-3-carboxylic acid

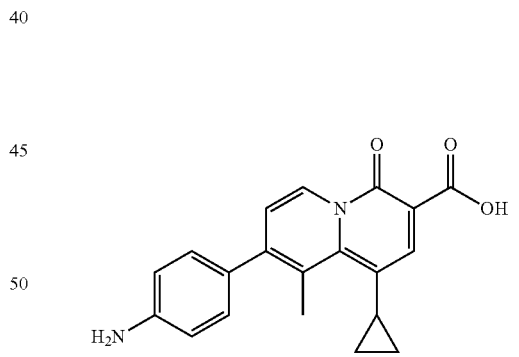

8-(4-Amino-phenyl)-1-cyclopropyl-9-methyl-4-oxo-4H-quinolizine-3-carboxylic acid was prepared according to General Procedure B using methyl 8-(4-amino-phenyl)-1-cyclopropyl-9-methyl-4-oxo-4H-quinolizine-3-carboxylate (25 mg, 0.07 mmol) to afford the title compound EXAMPLE 18 as a yellow solid (18 mg, 77%). ESI-MS m/z: 335 (M+H)$^+$; $^1$H NMR (400 MHz, DMSO-d6) δ ppm: 14.11 (s, 1H), 9.24 (d, J=7.1 Hz, 1H), 8.22 (s, 1H), 7.53 (s, 1H), 7.30 (d, J=8.1 Hz, 2H), 6.72 (d, J=8.4 Hz, 2H), 5.67 (s, 2H), 2.89 (s, 3H), 2.40-2.50 (m, 1H), 1.05-1.07 (m, 2H), 0.73-0.75 (m, 2H).

Example 19

Preparation of 2-methyl-4-(4,4,5,5-tetramethyl-1,3,2-dioxaborolan-2-yl)-aniline

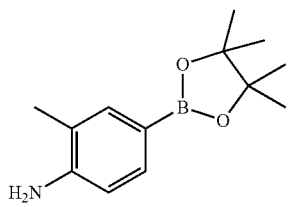 [SMILES: Cc1cc(B2OC(C)(C)C(C)(C)O2)ccc1N]

Potassium acetate (317 mg, 3.22 mmol), 4,4,4',4',5,5,5',5'-octamethyl-2,2'-bi(1,3,2-dioxaborolane) (300 mg, 1.18 mmol) and 4-bromo-2-methyl-aniline (200 mg, 1.08 mmol) were dissolved in dimethylsulfoxide (3 mL). The reaction mixture was degassed using argon. 1,1'-Bis-diphenylphosphine ferrocene palladium(II) dichloride (24 mg, 0.03 mmol) was added and the reaction mixture was heated at 80° C. for 5 h. The reaction mixture was cooled to room temperature and diluted with ethyl acetate (20 mL). The organic layer was washed with saturated sodium bicarbonate (20 mL) and brine (20 mL). The organic layer was dried with sodium sulfate, filtered and purified by flash silica column chromatography (heptane:ethyl acetate, 0-40%) to obtain a crude mixture of starting material and product. The mixture was purified using reversed phase column chromatography to obtain the title compound as a clear oil (50 mg, 21%). ESI-MS m/z: 234 (M+H)$^+$.

Preparation of methyl 8-(4-amino-3-methyl-phenyl)-1-cyclopropyl-9-methyl-4-oxo-4H-quinolizine-3-carboxylate

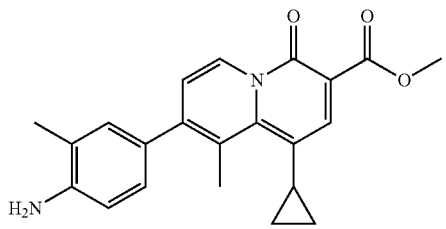

Methyl 8-(4-amino-3-methyl-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (50 mg, 0.17 mmol) and 4-(4,4,5,5-tetramethyl-1,3,2-dioxaborolan-2-yl)-aniline (52 mg, 0.22 mmol). Purification by flash silica column chromatography (CH$_2$Cl$_2$:MeOH) (1:0 to 9:1) afforded the title compound as a yellow solid (31 mg, 50%). ESI-MS m/z: 363 (M+H)$^+$.

Preparation of EXAMPLE 19 8-(4-amino-3-methyl-phenyl)-1-cyclopropyl-9-methyl-4-oxo-4H-quinolizine-3-carboxylic acid

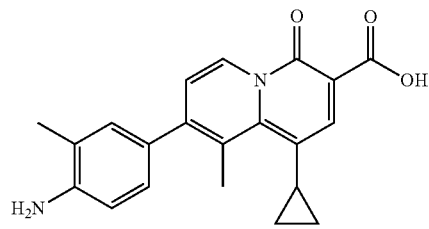

8-(4-Amino-3-methyl-phenyl)-1-cyclopropyl-9-methyl-4-oxo-4H-quinolizine-3-carboxylic acid was prepared according to General Procedure B using methyl 8-(4-amino-3-methyl-phenyl)-1-cyclopropyl-9-methyl-4-oxo-4H-quinolizine-3-carboxylate (31 mg, 0.09 mmol) to afford the title compound EXAMPLE 19 as a yellow solid (19 mg, 60%). ESI-MS m/z: 349 (M+H)$^+$; $^1$H NMR (400 MHz, DMSO-d6) δ ppm: 13.99 (s, 1H), 9.16-9.25 (m, 1H), 8.21-8.34 (m, 1H), 7.52-7.54 (m, 2H), 7.16-7.20 (m, 1H), 6.76 (d, J=8.1 Hz, 1H), 5.43 (s, 2H), 2.99 (s, 3H), 2.89 (s, 3H), 2.40-2.50 (m, 1H), 1.03-1.07 (m, 2H), 0.70-0.75 (m, 2H).

Example 20

Preparation of methyl 1-cyclopropyl-8-(2-fluoro-pyridin-4-yl)-9-methyl-4-oxo-4H-quinolizine-3-carboxylate

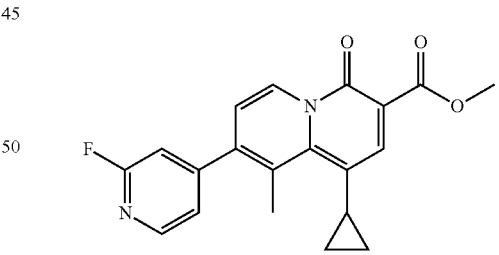

Methyl 1-cyclopropyl-8-(2-fluoro-pyridin-4-yl)-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 2-fluoro-pyridin-4-yl-boronic acid (72 mg, 0.51 mmol). Purification by flash silica column chromatography (CH$_2$Cl$_2$:MeOH) (1:0 to 94:6) afforded the title compound as a yellow solid (107 mg, 89%). ESI-MS m/z: 353 (M+H)$^+$.

Preparation of EXAMPLE 20 1-cyclopropyl-8-(2-fluoro-pyridin-4-yl)-9-methyl-4-oxo-4H-quinolizine-3-carboxylic acid

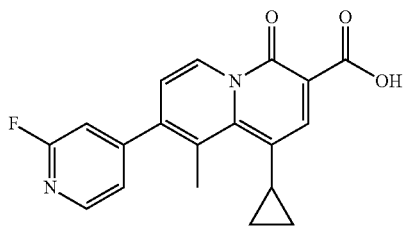 [SMILES: Cc1c(-c2ccnc(F)c2)ccn2c(=O)c(C(=O)O)cc(C3CC3)c12]

1-Cyclopropyl-8-(2-fluoro-pyridin-4-yl)-9-methyl-4-oxo-4H-quinolizine-3-carboxylic acid was prepared according to General Procedure B using methyl 1-cyclopropyl-8-(2-fluoro-pyridin-4-yl)-9-methyl-4-oxo-4H-quinolizine-3-carboxylate (107 mg, 0.30 mmol) to afford the title compound EXAMPLE 20 as a yellow solid (53 mg, 52%). ESI-MS m/z: 339 (M+H)$^+$; $^1$H NMR (400 MHz, DMSO-d6) δ ppm: 9.21-9.31 (m, 1H), 8.52 (s, 1H), 8.39-8.47 (m, 1H), 7.20-7.60 (m, 3H), 2.80 (s, 3H), 2.50-2.60 (m, 1H), 0.98-1.13 (m, 2H), 0.71-0.81 (m, 2H).

Example 21

Preparation of methyl 8-(6-amino-pyridin-3-yl)-1-cyclopropyl-9-methyl-4-oxo-4H-quinolizine-3-carboxylate

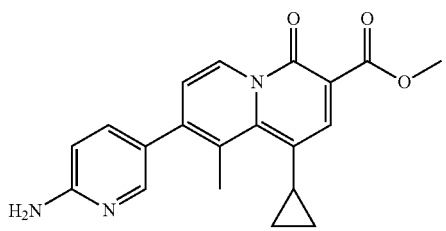 [SMILES: COC(=O)c1cc(C2CC2)c2c(C)c(-c3ccc(N)nc3)ccn2c1=O]

Methyl 8-(6-amino-pyridin-3-yl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 5-(4,4,5,5-tetramethyl-1,3,2-dioxaborolan-2-yl)-pyridin-2-amine (113 mg, 0.51 mmol). Purification by flash silica column chromatography (CH$_2$Cl$_2$:MeOH) (1:0 to 94:6) afforded the title compound as a yellow solid (135 mg, 100%). ESI-MS m/z: 350 (M+H)$^+$.

Preparation of EXAMPLE 21 8-(6-amino-pyridin-3-yl)-1-cyclopropyl-9-methyl-4-oxo-4H-quinolizine-3-carboxylic acid

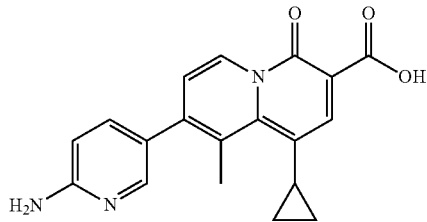 [SMILES: Cc1c(-c2ccc(N)nc2)ccn2c(=O)c(C(=O)O)cc(C3CC3)c12]

8-(6-Amino-pyridin-3-yl)-1-cyclopropyl-9-methyl-4-oxo-4H-quinolizine-3-carboxylic acid was prepared according to General Procedure B using methyl 8-(6-amino-pyridin-3-yl)-1-cyclopropyl-9-methyl-4-oxo-4H-quinolizine-3-carboxylate (61 mg, 0.17 mmol) to afford the title compound EXAMPLE 21 as a yellow solid (34 mg, 60%). ESI-MS m/z: 336 (M+H)$^+$; $^1$H NMR (400 MHz, DMSO-d6) δ ppm: 9.20 (d, J=7.6 Hz, 1H), 8.47 (s, 1H), 8.33 (s, 1H), 8.12 (s, 1H), 7.60 (dd, J=2.3 Hz, J=8.6 Hz, 1H), 8.29 (d, J=6.6 Hz, 1H), 6.59 (d, J=8.8 Hz, 1H), 6.39 (s, 2H), 2.84 (s, 3H), 2.50-2.60 (m, 1H), 1.23 (s, 2H), 1.03-1.07 (m, 4H) 0.70-0.72 (m, 2H).

Preparation of potassium 8-(6-amino-pyridin-3-yl)-1-cyclopropyl-9-methyl-4-oxo-4H-quinolizine-3-carboxylate

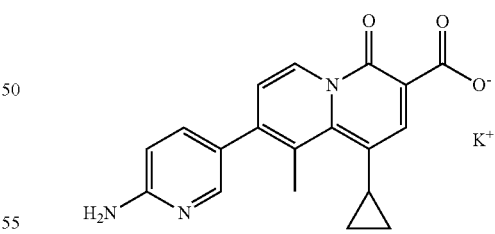

Potassium 8-(6-amino-pyridin-3-yl)-1-cyclopropyl-9-methyl-4-oxo-4H-quinolizine-3-carboxylate was prepared according to General Procedure D using 8-(6-amino-pyridin-3-yl)-1-cyclopropyl-9-methyl-4-oxo-4H-quinolizine-3-carboxylic acid (EXAMPLE 21) (510 mg, 1.52 mmol) to afford the K salt of the title compound as a yellow solid (564 mg, 99%). ESI-MS m/z: 336 (M−K$^+$ H)$^+$.

Example 22

Preparation of methyl 1-cyclopropyl-8-(1H-indol-5-yl)-9-methyl-4-oxo-4H-quinolizine-3-carboxylate

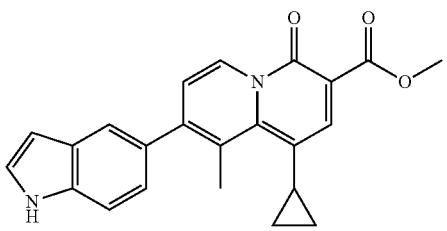 [SMILES: COC(=O)c1cc(C2CC2)c2c(C)c(-c3ccc4[nH]ccc4c3)ccn2c1=O]

Methyl 1-cyclopropyl-8-(1H-indol-5-yl)-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 1H-indol-5-yl-boronic acid (83 mg, 0.51 mmol) to afford the title compound as a yellow solid (60 mg, 47%). ESI-MS m/z: 373 (M+H)$^+$.

Preparation of EXAMPLE 22 1-cyclopropyl-8-(1H-indol-5-yl)-9-methyl-4-oxo-4H-quinolizine-3-carboxylic acid

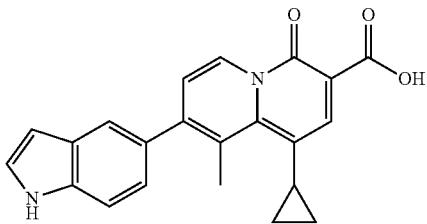 [SMILES: Cc1c(-c2ccc3[nH]ccc3c2)ccn2c(=O)c(C(=O)O)cc(C3CC3)c12]

1-Cyclopropyl-8-(1H-indol-5-yl)-9-methyl-4-oxo-4H-quinolizine-3-carboxylic acid was prepared according to General Procedure B using methyl 1-cyclopropyl-8-(1H-indol-5-yl)-9-methyl-4-oxo-4H-quinolizine-3-carboxylate (60 mg, 0.16 mmol) to afford the title compound EXAMPLE 22 as a yellow solid (20 mg, 35%). ESI-MS m/z: 359 (M+H)$^+$; $^1$H NMR (400 MHz, DMSO-d6) δ ppm: 11.35 (s, 1H), 9.24 (d, J=7.0 Hz, 1H), 8.48 (s, 1H), 7.70 (s, 1H), 7.50-7.60 (m, 2H), 7.46 (s, 1H), 7.31 (d, J=7.6 Hz, 1H), 7.22 (d, J=7.8 Hz, 1H), 6.54 (s, 1H), 2.84 (s, 3H), 2.50-2.60 (m, 1H), 1.00-1.08 (m, 2H), 0.72-0.76 (m, 2H).

Example 23

Preparation of methyl 1-cyclopropyl-8-(1H-indazol-5-yl)-9-methyl-4-oxo-4H-quinolizine-3-carboxylate

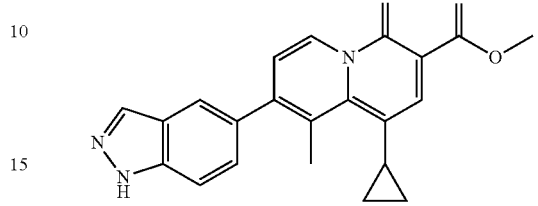

Methyl 8-chloro-1-cyclopropyl-9-methyl-4-oxo-4H-quinolizine-3-carboxylate (100 mg, 0.34 mmol), cesium carbonate (335 mg, 1.03 mmol) and 5-(4,4,5,5-tetramethyl-1,3,2-dioxaborolan-2-yl)-1H-indazole (92 mg, 0.38 mmol) were added to a mixture of 1,2-dimethoxyethane (3 mL) and water (1 mL). The mixture was degassed with argon. 1,1'-Bis-(diphenylphosphino)-ferrocene) palladium dichloride (28 mg, 0.03 mmol) was added. The reaction mixture was heated at 150° C. under argon atmosphere for 0.25 h. The reaction mixture was cooled. The mixture was diluted with $CH_2Cl_2$ (3 mL) and water was added (3 mL). The layers were separated using a phase separator and the aqueous layer was extracted with $CH_2Cl_2$ (2×5 mL). The combined organic layers were concentrated in vacuo. The crude product was purified by flash silica column chromatography ($CH_2Cl_2$:MeOH) (1:0 to 9:1) and dried in vacuo to afford the title compound as a yellow solid (93 mg, 72%). ESI-MS m/z: 374 (M+H)$^+$.

Preparation of EXAMPLE 23 1-cyclopropyl-8-(1H-indazol-5-yl)-9-methyl-4-oxo-4H-quinolizine-3-carboxylic acid

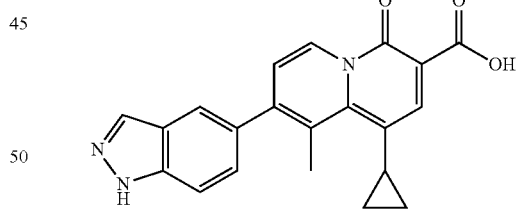

1-Cyclopropyl-8-(1H-indazol-5-yl)-9-methyl-4-oxo-4H-quinolizine-3-carboxylic acid was prepared according to General Procedure B using methyl 1-cyclopropyl-8-(1H-indazol-5-yl)-9-methyl-4-oxo-4H-quinolizine-3-carboxylate (555 mg, 1.49 mmol) to afford the title compound EXAMPLE 23 as a yellow solid (200 mg, 37%). ESI-MS m/z: 360 (M+H)$^+$; ([M−H]$^-$=358.2; 100%); $^1$H NMR (400 MHz, DMSO-d6) δ ppm: 14.13 (s, 1H), 13.35 (s, 1H), 9.36 (d, J=7.3 Hz, 1H), 8.25 (d, J=15.9 Hz, 2H), 8.01 (s, 1H), 7.74 (d, J=8.6 Hz, 1H), 7.67 (d, J=7.6 Hz, 1H), 7.54 (d, J=9.6 Hz, 1H), 2.90 (s, 3H), 2.40-2.60 (m, 1H), 1.07-1.11 (m, 2H), 0.79-0.82 (m, 2H).

Preparation of potassium 1-cyclopropyl-8-(1H-indazol-5-yl)-9-methyl-4-oxo-4H-quinolizine-3-carboxylate

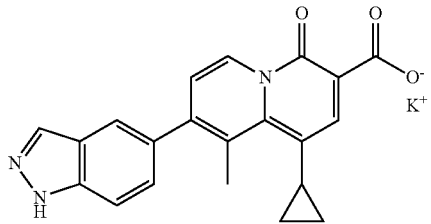 [SMILES: Cc1c(-c2ccc3[nH]ncc3c2)ccn2c(=O)c(C(=O)[O-])cc(C3CC3)c12 ; [K+]]

Potassium 1-cyclopropyl-8-(1H-indazol-5-yl)-9-methyl-4-oxo-4H-quinolizine-3-carboxylate was prepared according to General Procedure D using 1-cyclopropyl-8-(1H-indazol-5-yl)-9-methyl-4-oxo-4H-quinolizine-3-carboxylic acid (180 mg, 0.50 mmol) to afford the K salt of EXAMPLE 23 as a yellow solid (195 mg, 98%). ESI-MS m/z: 360 (M−K+ H)+.

Example 24

Preparation of methyl 1-cyclopropyl-9-methyl-4-oxo-8-(4-ureido-phenyl)-4H-quinolizine-3-carboxylate

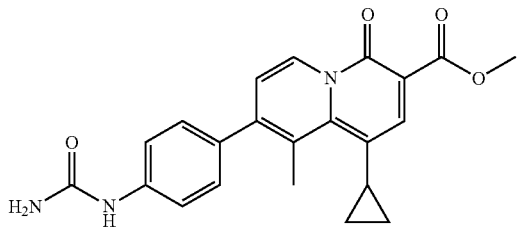 [SMILES: COC(=O)c1cc(C2CC2)c2c(C)c(-c3ccc(NC(N)=O)cc3)ccn2c1=O]

Methyl 1-cyclopropyl-9-methyl-4-oxo-8-(4-ureido-phenyl)-4H-quinolizine-3-carboxylate was prepared according to General Procedure A using methyl 8-chloro-1-cyclopropyl-9-methyl-4-oxo-4H-quinolizine-3-carboxylate (75 mg, 0.26 mmol) and 1-(4-(4,4,5,5-tetramethyl-1,3,2-dioxaborolan-2-yl)-phenyl)-urea (84 mg, 0.32 mmol). Compound precipitated from solution and was filtered off and dried in vacuo to afford the title compound as a yellow solid (29 mg, 26%). ESI-MS m/z: 392 (M+H)+.

Preparation of EXAMPLE 24 1-cyclopropyl-9-methyl-4-oxo-8-(4-ureido-phenyl)-4H-quinolizine-3-carboxylic acid

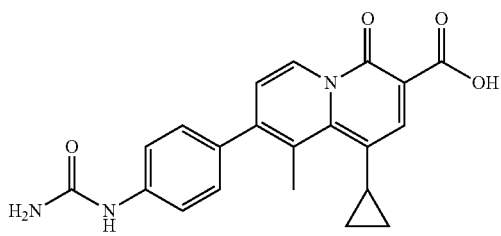 [SMILES: Cc1c(-c2ccc(NC(N)=O)cc2)ccn2c(=O)c(C(=O)O)cc(C3CC3)c12]

1-Cyclopropyl-9-methyl-4-oxo-8-(4-ureido-phenyl)-4H-quinolizine-3-carboxylic acid was prepared according to General Procedure B using methyl 1-cyclopropyl-9-methyl-4-oxo-8-(4-ureido-phenyl)-4H-quinolizine-3-carboxylate (28 mg, 0.07 mmol) to afford the title compound EXAMPLE 24 as a yellow solid (15 mg, 58%). ESI-MS m/z: 378 (M+H)+; $^1$H NMR (400 MHz, DMSO-d6) δ ppm: 14.10 (s, 1H), 9.30 (d, J=7.6 Hz, 1H), 9.09 (s, 1H), 8.23 (s, 1H), 7.57-7.63 (m, 3H), 7.46 (d, J=8.6 Hz, 2H), 6.04 (s, 2H), 2.89 (s, 3H), 2.40-2.55 (m, 1H), 1.06-1.08 (m, 2H), 0.76-0.78 (m, 2H).

Example 25

Preparation of methyl 1-cyclopropyl-8-(4-(dimethylamino)-phenyl)-9-methyl-4-oxo-4H-quinolizine-3-carboxylate

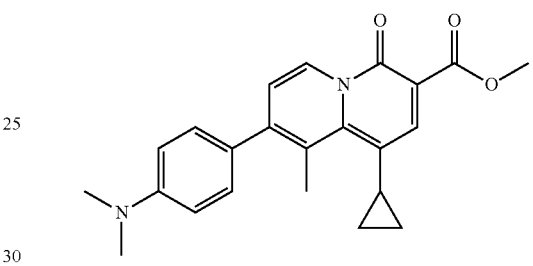

Methyl 1-cyclopropyl-8-(4-(dimethylamino)-phenyl)-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (77 mg, 0.26 mmol) and (4-(dimethylamino)-phenyl)-boronic acid (56 mg, 0.34 mmol). Purification by flash silica column chromatography (CH$_2$Cl$_2$:MeOH) (1:0 to 94:6) afforded the title compound as a yellow solid (39 mg, 31%). ESI-MS m/z: 377 (M+H)+.

Preparation of EXAMPLE 25 1-cyclopropyl-8-(4-(dimethylamino)-phenyl)-9-methyl-4-oxo-4H-quinolizine-3-carboxylic acid

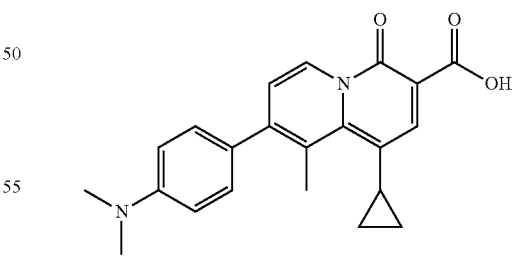

1-Cyclopropyl-8-(4-(dimethylamino)-phenyl)-9-methyl-4-oxo-4H-quinolizine-3-carboxylic acid was prepared according to General Procedure B using methyl 1-cyclopropyl-8-(4-(dimethylamino)-phenyl)-9-methyl-4-oxo-4H-quinolizine-3-carboxylate (34 mg, 0.09 mmol) to afford the title compound EXAMPLE 25 as a yellow solid (5.1 mg, 15%). ESI-MS m/z: 363 (M+H)+; $^1$H NMR (400 MHz, DMSO-d6) δ ppm: 9.10-9.20 (m, 1H), 8.44 (s, 1H), 7.20-7.40

(m, 3H), 6.80-6.85 (m, 2H), 2.88 (s, 6H), 2.82 (s, 3H), 2.50-2.60 (m, 1H), 0.98-1.05 (m, 1H), 0.65-0.70 (m, 1H).

Example 26

Preparation of methyl 8-(3-S-((tert-butoxycarbonyl)-amino)-pyrrolidin-1-yl)-1-cyclopropyl-9-methyl-4-oxo-4H-quinolizine-3-carboxylate

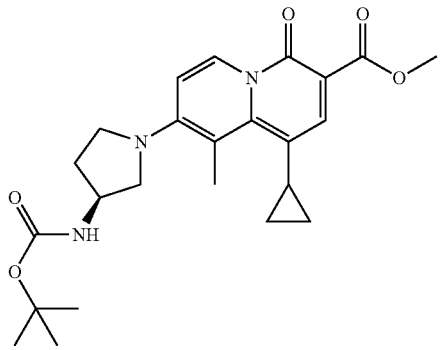 [SMILES: COC(=O)c1cc(C2CC2)c2c(C)c(N3CC[C@H](NC(=O)OC(C)(C)C)C3)ccn2c1=O]

Methyl 8-chloro-1-cyclopropyl-9-methyl-4-oxo-4H-quinolizine-3-carboxylate (100 mg, 0.34 mmol), tert-butyl-pyrrolidin-3-S-yl-carbamate (313 mg, 1.68 mmol) and tri-ethylamine (0.5 mL, 3.6 mmol) were added to 2-propanol (20 mL). The reaction mixture was heated at 130° C. and stirred for 6 h. The reaction mixture was cooled and evaporated to dryness. The crude product was purified by flash silica column chromatography (CH$_2$Cl$_2$:MeOH) (1:0 to 9:1) and dried in vacuo to afford the title compound as a yellow foam (70 mg, 46%). ESI-MS m/z: 442 (M+H)$^+$.

Preparation of EXAMPLE 26 8-(3-S-amino-pyrrolidin-1-yl)-1-cyclopropyl-9-methyl-4-oxo-4H-quinolizine-3-carboxylic acid

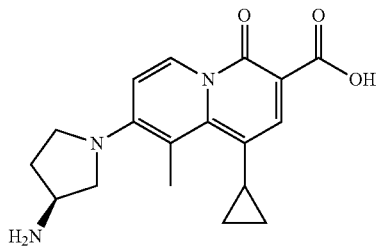 [SMILES: Cc1c(N2CC[C@H](N)C2)ccn2c(=O)c(C(=O)O)cc(C3CC3)c12]

8-(3-S-amino-pyrrolidin-1-yl)-1-cyclopropyl-9-methyl-4-oxo-4H-quinolizine-3-carboxylic acid was prepared according to General Procedure B using methyl 8-(3-S-((tert-butoxycarbonyl)-amino)-pyrrolidin-1-yl)-1-cyclopropyl-9-methyl-4-oxo-4H-quinolizine-3-carboxylate (76 mg, 0.17 mmol) to afford a yellow residue. The residue was treated according to General Procedure C and purified using preparative LCMS to afford the title compound EXAMPLE 26 as a yellow solid (5.5 mg, 10% over 2 steps). ESI-MS m/z: 328 (M+H)$^+$; $^1$H NMR (400 MHz, DMSO-d6) δ ppm: 9.03 (d, J=10.8 Hz, 1H), 7.90 (s, 1H), 5.41 (s, 1H), 3.90-4.00 (m, 1H), 3.80-3.90 (m, 1H), 3.65-3.80 (m, 1H), 3.50-3.60 (m, 1H), 3.30-3.40 (m, 2H), 2.58 (s, 3H), 2.40-2.60 (m, 1H), 2.26-2.30 (m, 1H), 2.01-2.06 (m, 1H), 1.72-1.76 (m, 1H), 0.95-0.98 (m, 2H), 0.57-0.60 (m, 2H).

Example 27

Preparation of methyl 8-(3-S-((tert-butoxycarbonyl)-amino)-pyrrolidin-1-yl)-1-cyclopropyl-7-fluoro-9-methyl-4-oxo-4H-quinolizine-3-carboxylate

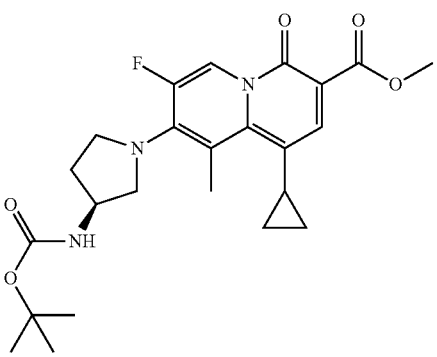 [SMILES: COC(=O)c1cc(C2CC2)c2c(C)c(N3CC[C@H](NC(=O)OC(C)(C)C)C3)c(F)cn2c1=O]

Ethyl 8-chloro-1-cyclopropyl-7-fluoro-9-methyl-4-oxo-4H-quinolizine-3-carboxylate (100 mg, 0.34 mmol), (S)-tert-butyl-pyrrolidin-3-ylcarbamate (313 mg, 1.68 mmol) and tri-ethylamine (0.5 mL, 3.6 mmol) were added to 2-propanol (20 mL). The reaction mixture was heated at 130° C. and stirred for 6 h. The reaction mixture was cooled and evaporated to dryness. The crude product was purified by flash silica column chromatography (CH$_2$Cl$_2$:MeOH) (1:0 to 9:1) and dried in vacuo to afford the title compound as a yellow foam (70 mg, 46%). ESI-MS m/z: 442 (M+H)$^+$.

Preparation of EXAMPLE 27 8-(3-S-amino-pyrrolidin-1-yl)-1-cyclopropyl-7-fluoro-9-methyl-4-oxo-4H-quinolizine-3-carboxylic acid

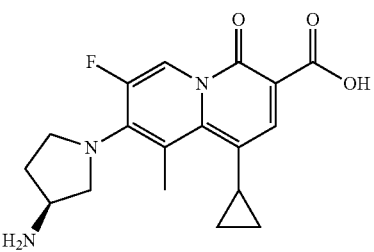 [SMILES: Cc1c(N2CC[C@H](N)C2)c(F)cn2c(=O)c(C(=O)O)cc(C3CC3)c12]

8-(3-S-Amino-pyrrolidin-1-yl)-1-cyclopropyl-7-fluoro-9-methyl-4-oxo-4H-quinolizine-3-carboxylic acid was prepared according to General Procedure B using (85 mg, 0.18 mmol) followed by hydrolysis according to General Procedure C. Purification using preparative LCMS afforded the title compound EXAMPLE 27 as a yellow solid (20.5 mg, 33% over 2 steps). ESI-MS m/z: 346 (M+H)$^+$; $^1$H NMR (400 MHz, DMSO-d6) δ ppm: 9.02 (d, J=8.1 Hz, 1H), 7.82 (s, 1H), 7.21 (d, J=8.1 Hz, 1H), 5.68 (s, 1H), 3.70-3.90 (m, 2H), 3.59-3.61 (m, 2H), 3.24-3.29 (m, 2H), 2.60 (s, 3H), 2.40-2.60

(m, 1H), 2.23-2.29 (m, 1H), 2.00-2.10 (m, 1H), 1.70-1.85 (m, 1H), 0.95-0.98 (m, 2H), 0.57-0.59 (m, 2H).

Example 28

Preparation of 2,5-difluoro-4-(4,4,5,5-tetramethyl-1,3,2-dioxaborolan-2-yl)-aniline

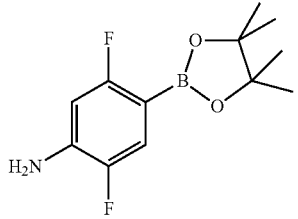 [SMILES: CC1(C)OB(c2cc(F)c(N)cc2F)OC1(C)C]

Potassium acetate (7.08 g, 72 mmol), 4,4,4',4',5,5,5',5'-octamethyl-2,2'-bi(1,3,2-dioxaborolane) (7.94 g, 31 mmol) and 4-bromo-2,5-difluoro-aniline (5 g, 24 mmol) were dissolved in 1,2-dimethoxyethane (60 mL), followed by the addition of 1'-Bis-diphenylphosphine ferrocene palladium (II) dichloride (2.1 g, 2.6 mmol). The reaction mixture was heated at 90° C. for 16 h. The reaction mixture was evaporated to dryness in vacuo. The mixture was coated onto hydromatrix and purified by flash silica column chromatography (heptane:ethyl acetate, 3:1). The product was dried in vacuo and crystallized from $CH_2Cl_2$ and heptane to give the title compound as a white solid (3.5 g, 57%). ESI-MS m/z: 297 $(M+MeCN+H)^+$, 256.2 $(M+H)^+$; $^1H$ NMR (400 MHz, $CDCl_3$) δ ppm: 7.30 (dd, J=5.0 Hz and J=11.1 Hz, 1H), 6.41 (q, J=6.8 Hz, 1H), 4.06 (br s, 1H), 1.33 (s, 12H).

Preparation of methyl 8-(4-amino-2,5-difluoro-phenyl)-1-cyclopropyl-9-methyl-4-oxo-4H-quinolizine-3-carboxylate

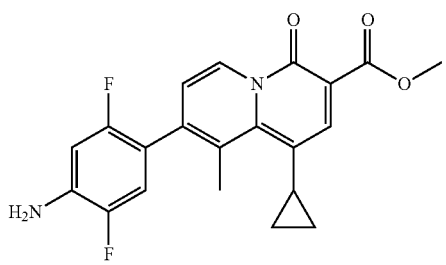 [SMILES: COC(=O)c1cc(C2CC2)c2c(C)c(-c3cc(F)c(N)cc3F)ccn2c1=O]

Methyl 8-(4-amino-2,5-difluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and 2,5-difluoro-4-(4,4,5,5-tetramethyl-1,3,2-dioxaborolan-2-yl)-aniline (667 mg, 2.06 mmol). Purification by flash silica column chromatography ($CH_2Cl_2$: MeOH) (1:0 to 9:1) afforded the title compound as a yellow solid (500 mg, 75%). ESI-MS m/z: 407 $(M+Na)^+$.

Preparation of EXAMPLE 28 8-(4-amino-2,5-difluoro-phenyl)-1-cyclopropyl-9-methyl-4-oxo-4H-quinolizine-3-carboxylic acid

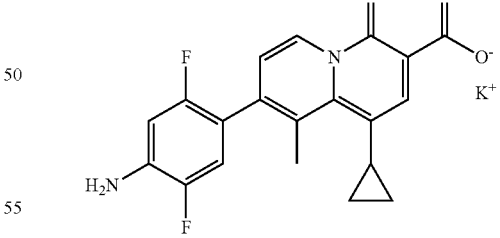

8-(4-Amino-2,5-difluoro-phenyl)-1-cyclopropyl-9-methyl-4-oxo-4H-quinolizine-3-carboxylic acid was prepared according to General Procedure B using methyl 8-(4-amino-2,5-difluoro-phenyl)-1-cyclopropyl-9-methyl-4-oxo-4H-quinolizine-3-carboxylate (1 g, 2.6 mmol) to afford the title compound EXAMPLE 28 as a yellow solid (639 mg, 66%). ESI-MS m/z: 371 $(M+H)^+$; $^1H$ NMR (400 MHz, DMSO-d6) δ ppm: 13.97 (s, 1H), 9.32 (d, J=5.5 Hz, 1H), 8.24 (s, 1H), 7.21 (d, J=12.1 Hz, 1H), 7.03 (d, J=8.1 Hz, 1H), 6.92 (t, J=8.7 Hz, 1H), 6.00 (s, 2H), 2.85 (s, 3H), 2.40-2.60 (m, 1H), 1.06-1.08 (m, 2H), 0.77-0.79 (m, 2H).

Preparation of potassium 8-(4-amino-2,5-difluoro-phenyl)-1-cyclopropyl-9-methyl-4-oxo-4H-quinolizine-3-carboxylate Potassium 8-(4-amino-2,5-difluoro-phenyl)-1-cyclopropyl-9-methyl-4-oxo-4H-quinolizine-3-carboxylate was prepared according to General Procedure D using 8-(4-amino-2,5-difluoro-phenyl)-1-cyclopropyl-9-methyl-4-oxo-4H-quinolizine-3-carboxylic acid (290 mg, 0.78 mmol) to afford the K salt of EXAMPLE 28 as a yellow solid (287 mg, 90%). ESI-MS m/z: 371 $(M-K^+ H)^+$.

Example 29

Preparation of ethyl 1-cyclopropyl-8-(4-amino-3,5-dichloro-phenyl)-9-methyl-4-oxo-4H-quinolizine-3-carboxylate

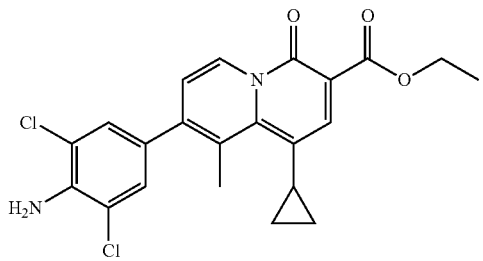 [SMILES: CCOC(=O)c1cc(C2CC2)c2c(C)c(-c3cc(Cl)c(N)c(Cl)c3)ccn2c1=O]

A mixture of 8-chloro-1-cyclopropyl-9-methyl-4-oxo-4H-quinolizine-3-carboxylic acid ethyl ester (120 mg, 0.400 mmol), 2,6-dichloro-[4-(4,4,5,5-tetramethyl-[1,3,2]dioxaborolan-2-yl)-aniline (138 mg, 0.48 mmol), $(Ph_3P)_2PdCl_2$ (28 mg, 0.040 mmol), and $Na_2CO_3$ (190 mg in 0.8 mL of water, 1.80 mmol) in THF (5 mL) was degassed 3 times under $N_2$ and heated to 80° C. overnight. The reaction mixture was diluted with ethyl acetate (50 mL) and washed with water (2×20 mL). The organic phase was separated, dried, and concentrated. The residue was purified by flash silica column chromatography (hexane:ethyl acetate, 2:3) to afford the title compound as a yellow solid (140 mg, 81%). ESI-MS m/z: 431 (M+H)+.

Preparation of EXAMPLE 29 1-cyclopropyl-8-(4-amino-3,5-dichloro-phenyl)-9-methyl-4-oxo-4H-quinolizine-3-carboxylic acid

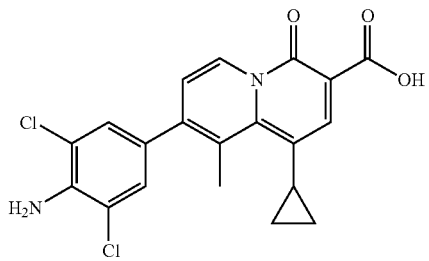

A solution of ethyl 1-cyclopropyl-8-(4-amino-3,5-dichloro-phenyl)-9-methyl-4-oxo-4H-quinolizine-3-carboxylate (140 mg, 0.326 mmol) in THF (6 mL) and water (2 mL) was treated with LiOH (55 mg, 1.31 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 29 as yellow solid (90 mg, 69%). ESI-MS m/z: 403 (M+H)+; $^1$H NMR (300 MHz, DMSO-d6) δ ppm: 9.30 (d, J=7.5 Hz, 1H), 8.25 (s, 1H), 7.64 (d, J=7.5 Hz, 1H), 7.57 (s, 2H), 6.12 (s, 2H), 2.92 (s, 3H), 2.54-2.51 (m, 1H), 1.13-1.10 (m, 2H), 0.84-0.83 (m, 2H).

Example 30

Preparation of ethyl 1-cyclopropyl-8-(4-amino-2-chloro-5-methyl-phenyl)-9-methyl-4-oxo-4H-quinolizine-3-carboxylate

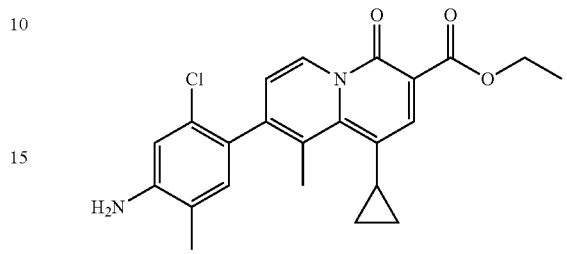

A mixture of ethyl 8-chloro-1-cyclopropyl-9-methyl-4-oxo-4H-quinolizine-3-carboxylate (120 mg, 0.4 mmol), 3-chloro-6-methyl-[4-(4,4,5,5-tetramethyl-[1,3,2]dioxaborolan-2-yl)-aniline (128 mg, 0.48 mmol), $(Ph_3P)_2PdCl_2$ (28 mg, 0.040 mmol), and $Na_2CO_3$ (190 mg in 0.8 mL of water, 1.80 mmol) in THF (5 mL) was degassed 3 times under $N_2$ and heated to 80° C. overnight. The reaction mixture was diluted with ethyl acetate (20 mL), and washed with water (20 mL). The organic phase was separated, dried, and concentrated. The residue was purified by flash silica column chromatography (hexane:ethyl acetate, 1:3) to afford the title compound as a yellow solid (70 mg, 43%). ESI-MS m/z: 411 (M+H)+.

Preparation of EXAMPLE 30 1-cyclopropyl-8-(4-amino-2-chloro-5-methyl-phenyl)-9-methyl-4-oxo-4H-quinolizine-3-carboxylic acid

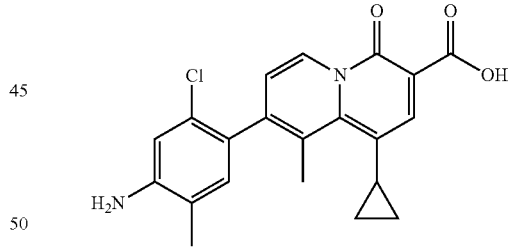

A solution of ethyl 1-cyclopropyl-8-(4-amino-2-chloro-5-methyl-phenyl)-9-methyl-4-oxo-4H-quinolizine-3-carboxylate (70 mg, 0.171 mmol) in THF (6 mL) and water (2 mL) was treated with LiOH (29 mg, 0.690 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 30 as yellow solid (51 mg, 78%). ESI-MS m/z: 383 (M+H)+; $^1$H NMR (300 MHz, DMSO-d6) δ ppm: 9.28 (d, J=7.5 Hz, 1H), 8.24 (s, 1H), 7.43 (d, J=7.5 Hz, 1H), 6.99 (s, 1H), 6.81 (s, 1H), 5.55 (s, 2H), 2.75 (s, 3H), 2.54-2.52 (m, 1H), 2.07 (s, 3H), 1.03-1.01 (m, 2H), 0.74-0.70 (m, 2H).

Example 31

Preparation of methyl 8-(4-(((tert-butoxycarbonyl)-amino)-methyl)-phenyl)-1-cyclopropyl-9-methyl-4-oxo-4H-quinolizine-3-carboxylate

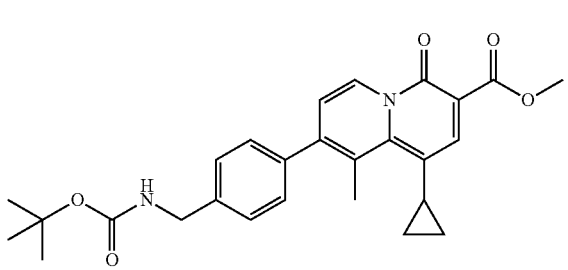 [SMILES: COC(=O)c1cc(C2CC2)c2c(C)c(-c3ccc(CNC(=O)OC(C)(C)C)cc3)ccn2c1=O]

Methyl 8-(4-(((tert-butoxycarbonyl)-amino)-methyl)-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and (4-(((tert-butoxycarbonyl)-amino)-methyl)-phenyl)-boronic acid (516 mg, 2.06 mmol). Purification by flash silica column chromatography ($CH_2Cl_2$:MeOH) (1:0 to 9:1) afforded the title compound as a yellow solid (850 mg, 100%). ESI-MS m/z: 485 (M+Na)$^+$, 463 (M+H)$^+$.

Preparation of 8-(4-(((tert-butoxycarbonyl)-amino)-methyl)-phenyl)-1-cyclopropyl-9-methyl-4-oxo-4H-quinolizine-3-carboxylic acid

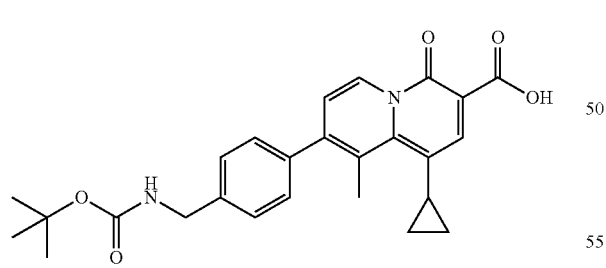

8-(4-(((tert-Butoxycarbonyl)-amino)-methyl)-phenyl)-1-cyclopropyl-9-methyl-4-oxo-4H-quinolizine-3-carboxylic acid was prepared according to General Procedure B using methyl 8-(4-(((tert-butoxycarbonyl)-amino)-methyl)-phenyl)-1-cyclopropyl-9-methyl-4-oxo-4H-quinolizine-3-carboxylate (1050 mg, 2.3 mmol) to afford the title compound as a yellow solid (950 mg, 93%). ESI-MS m/z: 449 (M+H)$^+$.

Preparation of EXAMPLE 31 8-(4-(aminomethyl)-phenyl)-1-cyclopropyl-9-methyl-4-oxo-4H-quinolizine-3-carboxylic acid

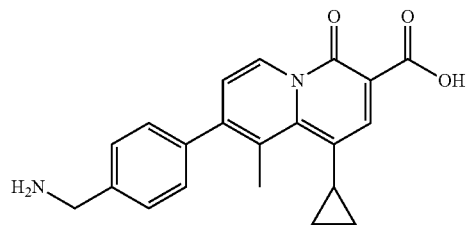 [SMILES: Cc1c(-c2ccc(CN)cc2)ccn2c(=O)c(C(=O)O)cc(C3CC3)c12]

8-(4-(Aminomethyl)-phenyl)-1-cyclopropyl-9-methyl-4-oxo-4H-quinolizine-3-carboxylic acid was prepared according to General Procedure C using 8-(4-(((tert-butoxycarbonyl)-amino)-methyl)-phenyl)-1-cyclopropyl-9-methyl-4-oxo-4H-quinolizine-3-carboxylic acid (540 mg, 1.20 mmol) to afford the title compound EXAMPLE 31 as a yellow solid (360 mg, 86%). ESI-MS m/z: 349 (M+H)$^+$; $^1$H NMR (400 MHz, DMSO-d6) δ ppm: 14.07 (s, 1H), 9.35 (d, J=7.3 Hz, 1H), 8.64 (s, 2H), 8.27 (s, 1H), 7.73 (d, J=7.8 Hz, 2H), 7.56-7.63 (m, 3H), 4.13 (s, 2H), 2.86 (s, 3H), 2.40-2.60 (m, 1H), 1.07-1.09 (m, 2H), 0.78-0.80 (m, 2H).

Preparation of potassium 8-(4-(amino-methyl)-phenyl)-1-cyclopropyl-9-methyl-4-oxo-4H-quinolizine-3-carboxylate

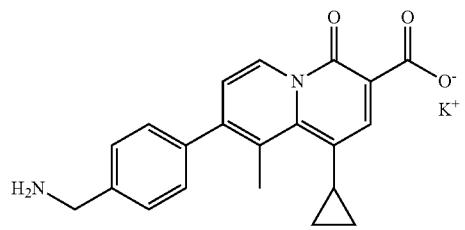 [SMILES: Cc1c(-c2ccc(CN)cc2)ccn2c(=O)c(C(=O)[O-])cc(C3CC3)c12 ; [K+]]

Potassium 8-(4-(amino-methyl)-phenyl)-1-cyclopropyl-9-methyl-4-oxo-4H-quinolizine-3-carboxylate was prepared according to General Procedure D using 8-(4-(amino-methyl)-phenyl)-1-cyclopropyl-9-methyl-4-oxo-4H-quinolizine-3-carboxylic acid (200 mg, 0.52 mmol) to afford the K salt of EXAMPLE 31 as a yellow solid (153 mg, 76%). ESI-MS m/z: 349 (M−K$^+$ H)$^+$.

Example 32

Preparation of ethyl 8-(4-(((tert-butoxycarbonyl)-amino)-methyl)-phenyl)-1-cyclopropyl-7-fluoro-9-methyl-4-oxo-4H-quinolizine-3-carboxylate

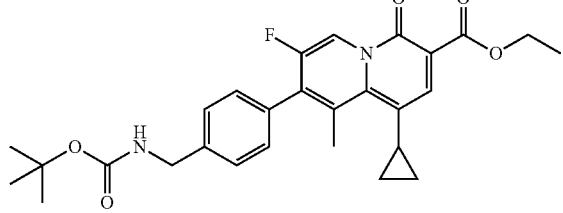

Ethyl 8-(4-(((tert-butoxycarbonyl)-amino)-methyl)-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (100 mg, 0.31 mmol) and (4-(((tert-butoxycarbonyl)-amino)-methyl)-phenyl)-boronic acid (101 mg, 0.40 mmol). Purification by flash silica column chromatography (CH$_2$Cl$_2$:MeOH) (1:0 to 9:1) afforded the title compound as a yellow solid (167 mg, 100%). ESI-MS m/z: 495 (M+Na)$^+$.

Preparation of 8-(4-(((tert-butoxycarbonyl)-amino)-methyl)-phenyl)-1-cyclopropyl-7-fluoro-9-methyl-4-oxo-4H-quinolizine-3-carboxylic acid

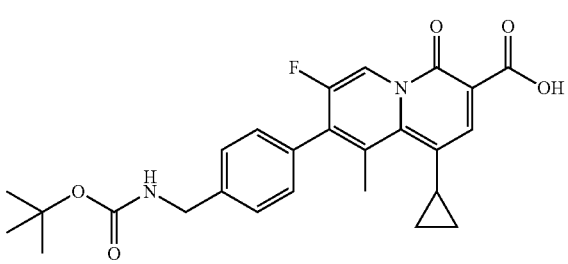 [SMILES: Cc1c(-c2ccc(CNC(=O)OC(C)(C)C)cc2)c(F)cn2c(=O)c(C(=O)O)cc(C3CC3)c12]

8-(4-(((tert-Butoxycarbonyl)-amino)-methyl)-phenyl)-1-cyclopropyl-7-fluoro-9-methyl-4-oxo-4H-quinolizine-3-carboxylic acid was prepared according to General Procedure B using ethyl 8-(4-(((tert-butoxycarbonyl)-amino)-methyl)-phenyl)-1-cyclopropyl-7-fluoro-9-methyl-4-oxo-4H-quinolizine-3-carboxylate (167 mg, 0.34 mmol) to afford the title compound as a yellow solid (150 mg, 95%). ESI-MS m/z: 467 (M+H)$^+$.

Preparation of EXAMPLE 32 8-(4-amino-methyl-phenyl)-1-cyclopropyl-7-fluoro-9-methyl-4-oxo-4H-quinolizine-3-carboxylic acid

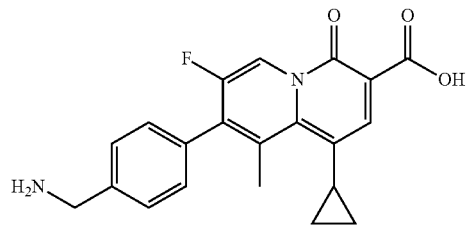 [SMILES: Cc1c(-c2ccc(CN)cc2)c(F)cn2c(=O)c(C(=O)O)cc(C3CC3)c12]

8-(4-Amino-methyl-phenyl)-1-cyclopropyl-7-fluoro-9-methyl-4-oxo-4H-quinolizine-3-carboxylic acid was prepared according to General Procedure C using 8-(4-(((tert-butoxycarbonyl)-amino)-methyl)-phenyl)-1-cyclopropyl-7-fluoro-9-methyl-4-oxo-4H-quinolizine-3-carboxylic acid (150 mg, 0.32 mmol) to afford the title compound EXAMPLE 32 as a yellow solid (137 mg, 100%). ESI-MS m/z: 367 (M+H)$^+$; $^1$H NMR (400 MHz, DMSO-d6) δ ppm: 13.9 (br s, 1H), 9.41 (d, J=7.3 Hz, 1H), 8.50 (br s, 2H), 8.28 (s, 1H), 7.72 (d, J=7.8 Hz, 2H), 7.56 (d, J=7.8 Hz 2H), 4.16 (s, 2H), 2.79 (s, 3H), 2.40-2.60 (m, 1H), 1.05-1.09 (m, 2H), 0.79-0.82 (m, 2H).

Preparation of potassium 8-(4-amino-methyl)-phenyl)-1-cyclopropyl-7-fluoro-9-methyl-4-oxo-4H-quinolizine-3-carboxylate

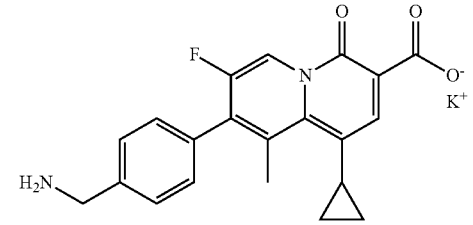 [SMILES: Cc1c(-c2ccc(CN)cc2)c(F)cn2c(=O)c(C(=O)[O-])cc(C3CC3)c12 ; [K+]]

Potassium 8-(4-amino-methyl)-phenyl)-1-cyclopropyl-7-fluoro-9-methyl-4-oxo-4H-quinolizine-3-carboxylate was prepared according to General Procedure D 8-(4-aminomethyl-phenyl)-1-cyclopropyl-7-fluoro-9-methyl-4-oxo-4H-quinolizine-3-carboxylic acid (65 mg, 0.16 mmol) to afford the K salt of EXAMPLE 32 as a yellow solid (79 mg, 100%). ESI-MS m/z: 367 (M−K$^+$H))$^+$; $^1$H NMR (400 MHz, DMSO-d6) δ ppm: 13.9 (br s, 1H), 9.40 (d, J=7.3 Hz, 1H), 8.43 (br s, 2H), 8.28 (s, 1H), 7.72 (d, J=7.8 Hz, 2H), 7.56 (d, J=7.8 Hz, 2H), 4.16 (s, 2H), 2.79 (s, 3H), 2.50-2.55 (m, 1H), 1.05-1.09 (m, 2H), 0.79-0.82 (m, 2H).

Example 33

Preparation of ethyl 1-cyclopropyl-8-(4-methyl-phenyl)-9-methyl-4-oxo-4H-quinolizine-3-carboxylate

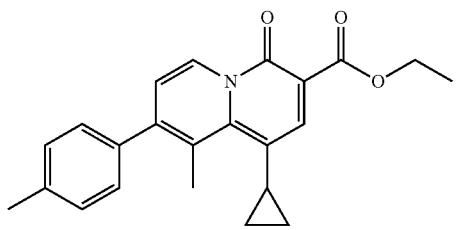 [SMILES: CCOC(=O)c1cc(C2CC2)c2c(C)c(-c3ccc(C)cc3)ccn2c1=O]

A mixture of 8-chloro-1-cyclopropyl-9-methyl-4-oxo-4H-quinolizine-3-carboxylic acid ethyl ester (120 mg, 0.400 mmol), 4-methyl-phenyl boronic acid (65 mg, 0.48 mmol), $(Ph_3P)_2PdCl_2$ (28 mg, 0.040 mmol), and $Na_2CO_3$ (190 mg in 0.8 mL of water, 1.80 mmol) in THF (5 mL) was degassed 3 times under $N_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl acetate, 1:2) to afford the title compound as a yellow solid (90 mg, 62%). ESI-MS m/z: 362 (M+H)+.

Preparation of EXAMPLE 33 1-cyclopropyl-8-(4-methyl-phenyl)-9-methyl-4-oxo-4H-quinolizine-3-carboxylic acid

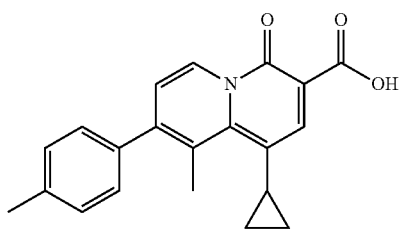 [SMILES: Cc1ccc(-c2ccn3c(=O)c(C(=O)O)cc(C4CC4)c3c2C)cc1]

A solution of ethyl 1-cyclopropyl-8-(4-methylphenyl)-9-methyl-4-oxo-4H-quinolizine-3-carboxylate (90 mg, 0.249 mmol) in THF (6 mL) and water (2 mL) was treated with LiOH (43 mg, 1.02 mmol). The reaction was heated to 60° C. for 2 h and acidified with 1N HCl to pH 4. The precipitate was dissolved with ethyl acetate (20 mL) and washed with brine (20 mL). The organic phase was separated, dried, and concentrated. The precipitate was filtered to afford the title compound EXAMPLE 33 as a yellow solid (65 mg, 78%). ESI-MS m/z: 334 (M+H)+; 1H NMR (300 MHz, DMSO-d6) δ ppm: 9.31 (d, J=7.2 Hz, 1H), 8.24 (s, 1H), 7.54 (d, J=7.2 Hz, 1H), 7.44 (d, J=7.2 Hz, 2H), 7.38 (d, J=7.2 Hz, 2H), 2.84 (s, 3H), 2.54-2.52 (m, 1H), 2.39 (s, 3H), 1.06-1.03 (m, 2H), 0.77-0.75 (m, 2H).

Example 34

Preparation of 1-cyclopropyl-9-methyl-4-oxo-8-piperazin-1-yl-quinolizine-3-carboxylic acid

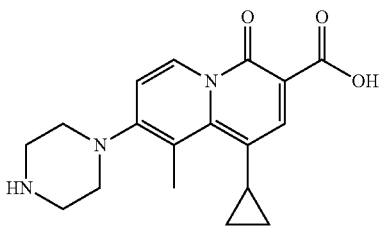 [SMILES: Cc1c(N2CCNCC2)ccn2c(=O)c(C(=O)O)cc(C3CC3)c12]

A mixture of methyl 8-chloro-1-cyclopropyl-9-methyl-4-oxo-4H-quinolizine-3-carboxylate (200 mg, 0.69 mmol), N-(tert-butoxycarbonyl)-piperazine (256 mg, 1.38 mmol) and $NaHCO_3$ (259 mg, 14.64 mmol) in ACN (8.6 mL) was heated in a microwave at 120° C. for 20 min. DMF (2 mL) was added to the mixture and the reaction was heated in a microwave at 120° C. for 20 min. Then the reaction was heated in a microwave at 130° C. for 30 min twice. The reaction mixture was diluted with ethyl acetate (30 mL), and washed with water (30 mL). After extraction of the aqueous phase with ethyl acetate (2×30 mL), the organic phases were combined washed with brine, dried with magnesium sulfate, filtrated, and concentrated. The residue was dissolved in TFA (1 mL) and agitated for 1 hour prior to evaporation of the solvent. The residue was dissolved in THF (1 mL) and an aqueous 4M NaOH solution (0.79 mL) and heated in a microwave at 120° C. for 10 min. More aqueous 4M NaOH solution (0.5 mL) was added and the reaction was heated in a microwave at 120° C. for 10 min. The mixture was evaporated and the residue purified by preparative HPLC. The title compound EXAMPLE 34 was obtained after lyophilization (28 mg, 12.5%). High-Res MS: calculated 328.1656 (M+H)+. found 328.1642 (M+H)+.

Example 35

Preparation of 8-[(3S)-3-amino-1-piperidyl]-1-cyclopropyl-9-methyl-4-oxo-quinolizine-3-carboxylic acid

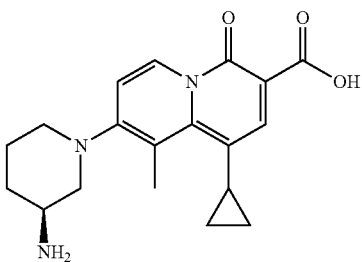 [SMILES: Cc1c(N2CCC[C@H](N)C2)ccn2c(=O)c(C(=O)O)cc(C3CC3)c12]

A mixture of methyl 8-chloro-1-cyclopropyl-9-methyl-4-oxo-4H-quinolizine-3-carboxylate (300 mg, 1 mmol), 3-S—N-(tert-butoxycarbonyl)-amino)-piperidine (413 mg, 2 mmol) and $NaHCO_3$ (390 mg, 14.64 mmol) in ACN (13 mL) was heated in a microwave at 120° C. for 20 min, and twice at 130° C. for 30 min. The reaction mixture was diluted with ethyl acetate (30 mL), and washed with water (30 mL). After extraction of the aqueous phase with ethyl acetate (2×30 mL), the organic phases were combined washed with brine, dried with magnesium sulfate, filtrated, and concentrated. The residue was dissolved in TFA (1 mL) and agitated for 1 hour prior to evaporation of the solvent. The residue was dissolved in THF (1 mL) and an aqueous 4M NaOH solution (1.4 mL) and heated in a microwave at 100° C. for 10 min and at 120° C. for 10 min. The mixture was evaporated and the residue purified by preparative HPLC. The title compound EXAMPLE 35 was obtained after lyophilization (65 mg, 19%). High-Res MS: calculated m/z 342.1812 (M+H)$^+$. found m/z 342.1787 (M+H)$^+$.

Example 36

Preparation of methyl 8-(4-cyano-phenyl)-1-cyclopropyl-9-methyl-4-oxo-4H-quinolizine-3-carboxylate

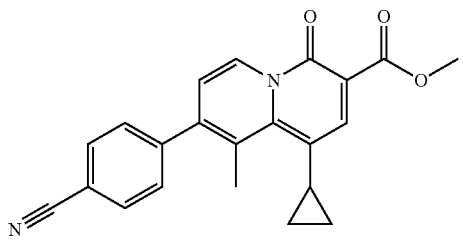 [SMILES: COC(=O)c1cc(C2CC2)c2c(C)c(-c3ccc(C#N)cc3)ccn2c1=O]

Methyl 8-(4-cyano-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (123 mg, 0.42 mmol) and 4-cyano-phenyl-boronic acid (132 mg, 0.90 mmol). Purification by flash silica column chromatography (CH$_2$Cl$_2$:MeOH) (1:0 to 9:1) afforded the title compound as a yellow solid (142 mg, 94%). ESI-MS m/z: 359 (M+H)$^+$.

Preparation of EXAMPLE 36 8-(4-carbamoyl-phenyl)-1-cyclopropyl-9-methyl-4-oxo-4H-quinolizine-3-carboxylic acid

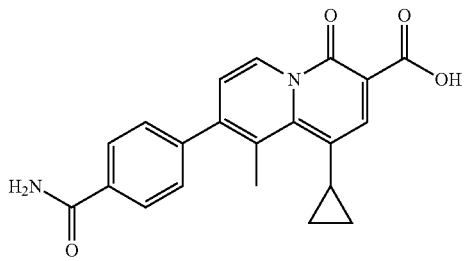

8-(4-Carbamoyl-phenyl)-1-cyclopropyl-9-methyl-4-oxo-4H-quinolizine-3-carboxylic acid was prepared according to General Procedure B using methyl 8-(4-cyano-phenyl)-1-cyclopropyl-9-methyl-4-oxo-4H-quinolizine-3-carboxylate (123 mg, 0.35 mmol) and purified by preparative LCMS to afford the title compound EXAMPLE 36 as a yellow solid (9.1 mg, 7%). ESI-MS m/z: 363 (M+H)$^+$; $^1$H NMR (400 MHz, DMSO-d6) δ ppm: 9.25 (d, J=7.3 Hz, 1H), 8.24 (s, 1H), 8.12 (s, 1H), 8.04 (d, J=8.1 Hz, 1H), 7.61 (d, J=8.1 Hz, 1H), 7.50 (s, 1H), 7.35 (d, J=7.1 Hz, 1H), 2.81 (s, 3H), 2.50-2.60 (m, 1H), 1.02-1.10 (m, 2H), 0.71-0.79 (m, 2H).

Example 37

Preparation of EXAMPLE 37 8-(4-carboxy-phenyl)-1-cyclopropyl-9-methyl-4-oxo-4H-quinolizine-3-carboxylic acid

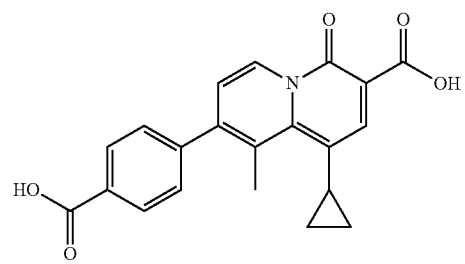

8-(4-Carboxy-phenyl)-1-cyclopropyl-9-methyl-4-oxo-4H-quinolizine-3-carboxylic acid was prepared according to General Procedure B using methyl 8-(4-cyano-phenyl)-1-cyclopropyl-9-methyl-4-oxo-4H-quinolizine-3-carboxylate (123 mg, 0.35 mmol). Preparative LC-MS purification afforded the title compound EXAMPLE 37 as a yellow solid (9.3 mg, 7%). ESI-MS m/z: 364 (M+H)$^+$; $^1$H NMR (400 MHz, DMSO-d6) δ ppm: 9.36 (d, J=7.3 Hz, 1H), 8.50 (br s, 1H), 8.08 (d, J=8.1 Hz, 1H), 7.47 (d, J=8.1 Hz, 1H), 7.32 (br s, 1H), 2.86 (s, 3H), 2.46-2.55 (m, 1H), 1.02-1.12 (m, 1H), 0.78-0.82 (m, 1H).

Example 38

Preparation of ethyl 8-(4-amino-2,5-difluoro-phenyl)-1-cyclopropyl-7-fluoro-9-methyl-4-oxo-4H-quinolizine-3-carboxylate

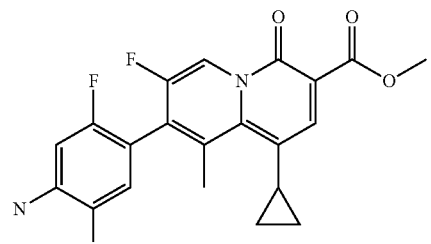

Ethyl 8-chloro-1-cyclopropyl-7-gluoro-9-methyl-4-oxo-4H-quinolizine-3-carboxylate (100 mg, 0.32 mmol), 2,5-difluoro-4-(4,4,5,5-tetramethyl-1,3,2-dioxaborolan-2-yl)-aniline (667 mg, 2.06 mmol), tricyclohexylphosphine (105 mg, 0.41 mmol) and cesium fluoride (482 mg, 3.2 mmol) were added to acetonitrile (5 mL). The reaction mixture was degassed with argon. Palladium(II) acetate (24 mg, 0.11 mmol) was added. The reaction mixture was heated at 85° C. for 2 h. The reaction mixture was cooled and evaporated in vacuo. Purification by flash silica column chromatography (CH₂Cl₂:MeOH) (1:0 to 9:1) afforded the title compound as a yellow solid (100 mg, 35%). ESI-MS m/z: 403 (M+H)⁺.

Preparation of EXAMPLE 38 8-(4-amino-2,5-difluoro-phenyl)-1-cyclopropyl-7-fluoro-9-methyl-4-oxo-4H-quinolizine-3-carboxylic acid

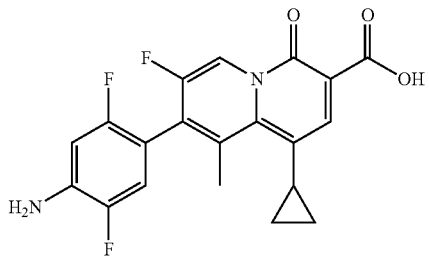 [SMILES: Cc1c(-c2cc(F)c(N)cc2F)c(F)cn2c(=O)c(C(=O)O)cc(C3CC3)c12]

8-(4-Amino-2,5-difluoro-phenyl)-1-cyclopropyl-7-fluoro-9-methyl-4-oxo-4H-quinolizine-3-carboxylic acid was prepared according to General Procedure B using ethyl 8-(4-amino-2,5-difluoro-phenyl)-1-cyclopropyl-7-fluoro-9-methyl-4-oxo-4H-quinolizine-3-carboxylate (100 mg, 0.24 mmol). The compound was purified using preparative LCMS and dried in vacuo to afford the title compound EXAMPLE 38 as a yellow solid (11 mg, 12%). ESI-MS m/z: 389 (M+H)⁺; ¹H NMR (400 MHz, DMSO-d6) δ ppm: 14.0 (br s, 1H), 9.30 (d, J=4.3 Hz, 1H), 8.26 (s, 1H), 7.25 (q, J=6.6 Hz, 1H), 6.72 (t, J=7.6 Hz, 1H), 6.02 (s, 2H), 2.84 (s, 3H), 2.50-2.60 (m, 1H), 0.98-1.12 (m, 2H), 0.63-0.83 (m, 2H).

Example 39

Preparation of 2,6-difluoro-4-(4,4,5,5-tetramethyl-1,3,2-dioxaborolan-2-yl)-aniline

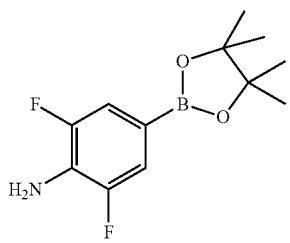 [SMILES: CC1(C)OB(c2cc(F)c(N)c(F)c2)OC1(C)C]

Potassium acetate (7.08 g, 72 mmol), 4,4,4',4',5,5,5',5'-octamethyl-2,2'-bi(1,3,2-dioxaborolane) (6.7 g, 26 mmol) and 4-bromo-2,6-difluoroaniline (5 g, 24 mmol) were dissolved in dimethylsulfoxide (30 mL), followed by the addition of 1'-Bis-diphenylphosphine ferrocene palladium(II) dichloride (0.53 g, 0.7 mmol). The reaction mixture was heated at 80° C. for 16 h. The reaction mixture was diluted in ethyl acetate (150 mL) and washed with saturated sodium bicarbonate and brine (2×100 mL). The organic layer was collected, dried over sodium sulfate and dried in vacuo. Purification by flash silica column chromatography (hexane:ethyl acetate, 3:2) afforded the title compound as a white solid (4.5 g, 73%). ESI-MS m/z: 297 (M+MeCN+H)⁺, 256 (M+H)⁺; ¹H NMR (400 MHz, CDCl₃) δ ppm: 7.20-7.30 (m, 2H), 3.93 (br s, 2H), 1.32 (s, 12H).

Preparation of methyl 8-(4-amino-3,6-difluoro-phenyl)-1-cyclopropyl-9-methyl-4-oxo-4H-quinolizine-3-carboxylate

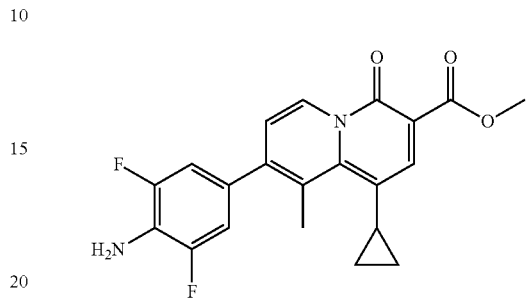

Methyl 8-(4-amino-3,6-difluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and 2,6-difluoro-4-(4,4,5,5-tetramethyl-1,3,2-dioxaborolan-2-yl)-aniline (667 mg, 2.06 mmol). Purification by flash silica column chromatography (CH₂Cl₂: MeOH) (1:0 to 9:1) afforded the title compound as a yellow solid (1140 mg, 86%). ESI-MS m/z: 423 (M+K)⁺, 407 (M+Na)⁺, 385 (M+H)⁺.

Preparation of EXAMPLE 39 8-(4-amino-3,5-difluoro-phenyl)-1-cyclopropyl-9-methyl-4-oxo-4H-quinolizine-3-carboxylic acid

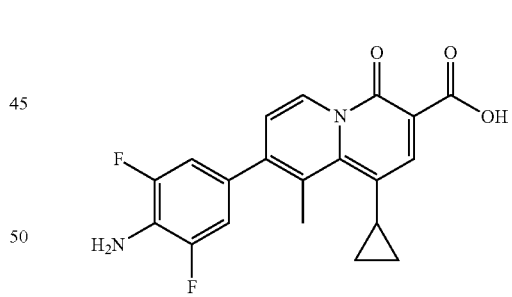

8-(4-Amino-3,5-difluoro-phenyl)-1-cyclopropyl-9-methyl-4-oxo-4H-quinolizine-3-carboxylic acid was prepared according to General Procedure B using methyl 8-(4-amino-3,6-difluoro-phenyl)-1-cyclopropyl-9-methyl-4-oxo-4H-quinolizine-3-carboxylate (1140 mg, 3.0 mmol) to afford the title compound EXAMPLE 39 as a yellow solid (916 mg, 97%). ESI-MS m/z: 371 (M+H)⁺; ¹H NMR (400 MHz, DMSO-d6) δ ppm: 14.08 (s, 1H), 9.26 (d, J=7.3 Hz, 1H), 8.22 (s, 1H), 7.59 (d, J=7.6 Hz, 1H), 7.25 (d, J=7.3 Hz, 2H), 5.80 (s, 2H), 2.89-2.91 (m, 3H), 2.40-2.60 (m, 1H), 1.07-1.09 (m, 2H), 0.77-0.79 (m, 2H).

89
Preparation of potassium 8-(4-amino-3,5-difluoro-phenyl)-1-cyclopropyl-9-methyl-4-oxo-4H-quinolizine-3-carboxylate

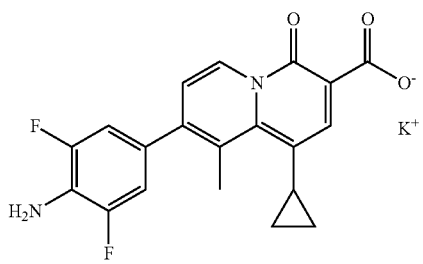 [SMILES: Cc1c(-c2cc(F)c(N)c(F)c2)ccn2c(=O)c(C(=O)[O-])cc(C3CC3)c12 ; [K+]]

Potassium 8-(4-amino-3,5-difluoro-phenyl)-1-cyclopropyl-9-methyl-4-oxo-4H-quinolizine-3-carboxylate was prepared according to General Procedure D using 8-(4-amino-3,5-difluoro-phenyl)-1-cyclopropyl-9-methyl-4-oxo-4H-quinolizine-3-carboxylic acid (300 mg, 0.81 mmol) to afford the title compound as a yellow solid (335 mg, 100%). ESI-MS m/z: 371 (M−K+ H)+.

Example 40

Preparation of methyl 8-(4-cyano-3-fluoro-phenyl)-1-cyclopropyl-9-methyl-4-oxo-4H-quinolizine-3-carboxylate

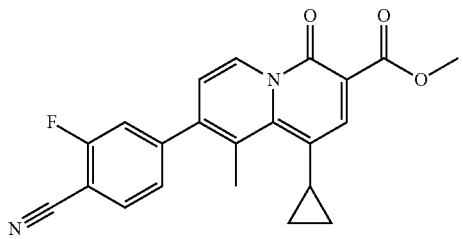 [SMILES: COC(=O)c1cc(C2CC2)c2c(C)c(-c3ccc(C#N)c(F)c3)ccn2c1=O]

Methyl 8-(4-cyano-3-fluoro-phenyl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and 4-cyano-3-fluoro-phenyl-boronic acid (85 mg, 0.51 mmol). Purification by flash silica column chromatography (CH$_2$Cl$_2$:MeOH) (1:0 to 94:6) afforded the title compound as a yellow solid (135 mg, 98%). ESI-MS m/z: 377 (M+H)+.

90
Preparation of EXAMPLE 40 8-(4-cyano-3-fluoro-phenyl)-1-cyclopropyl-9-methyl-4-oxo-4H-quinolizine-3-carboxylic acid

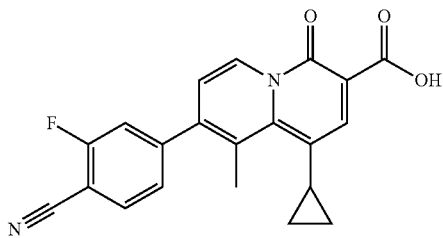 [SMILES: Cc1c(-c2ccc(C#N)c(F)c2)ccn2c(=O)c(C(=O)O)cc(C3CC3)c12]

8-(4-Cyano-3-fluoro-phenyl)-1-cyclopropyl-9-methyl-4-oxo-4H-quinolizine-3-carboxylic acid was prepared according to General Procedure B using me methyl 8-(4-cyano-3-fluoro-phenyl)-1-cyclopropyl-9-methyl-4-oxo-4H-quinolizine-3-carboxylate (135 mg, 0.36 mmol) to afford the title compound EXAMPLE 40 as a yellow solid (37 mg, 28%). ESI-MS m/z: 363 (M+H)+; $^1$H NMR (400 MHz, DMSO-d6) δ ppm: 14.0 (br s, 1H), 9.30 (d, J=7.3 Hz, 1H), 8.33 (s, 1H), 8.15 (t, J=7.6 Hz, 1H), 7.81 (d, J=7.6 Hz, 1H), 7.59-7.61 (m, 1H), 7.38-7.52 (m, 1H), 2.82 (s, 3H), 2.40-2.60 (m, 1H), 1.00-1.18 (m, 2H), 0.73-0.92 (m, 2H).

Example 41

Preparation of ethyl 8-(4-cyano-phenyl)-1-cyclopropyl-7-fluoro-9-methyl-4-oxo-4H-quinolizine-3-carboxylate

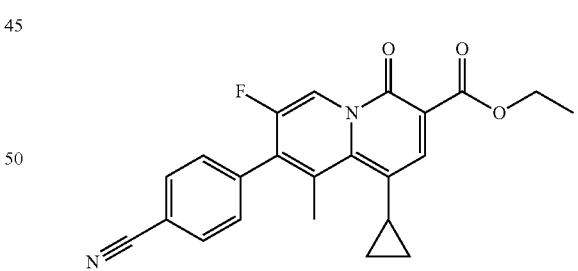

Ethyl 8-(4-cyano-phenyl)-1-cyclopropyl-7-fluoro-9-methyl-4-oxo-4H-quinolizine-3-carboxylate was prepared according to General Procedure A using ethyl 8-chloro-1-cyclopropyl-7-fluoro-9-methyl-4-oxo-4H-quinolizine-3-carboxylate (151 mg, 0.47 mmol) and 4-cyano-phenyl-boronic acid (82 mg, 0.56 mmol). Purification by flash silica column chromatography (CH$_2$Cl$_2$:MeOH, 1:0 to 9:1) afforded the title compound as a yellow solid (189 mg, 100%). ESI-MS m/z: 391 (M+H)+.

Preparation of EXAMPLE 41 8-(4-carboxy-phenyl)-1-cyclopropyl-7-fluoro-9-methyl-4-oxo-4H-quinolizine-3-carboxylic acid

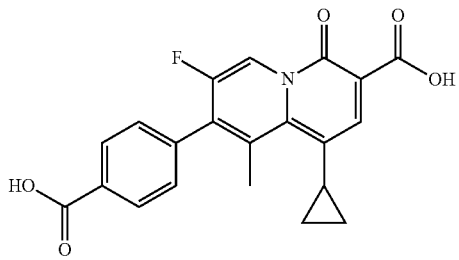 [SMILES: Cc1c(-c2ccc(C(=O)O)cc2)c(F)cn2c(=O)c(C(=O)O)cc(C3CC3)c12]

8-(4-Carboxy-phenyl)-1-cyclopropyl-7-fluoro-9-methyl-4-oxo-4H-quinolizine-3-carboxylic acid was prepared according to General Procedure B using methyl 8-(4-cyano-phenyl)-1-cyclopropyl-7-fluoro-9-methyl-4-oxo-4H-quinolizine-3-carboxylate (123 mg, 0.35 mmol). Preparative LC-MS purification afforded the title compound EXAMPLE 41 as a yellow solid (12 mg, 7%). ESI-MS m/z: 382 (M+H)$^+$; $^1$H NMR (400 MHz, CD$_3$OD) δ ppm 9.40 (br s, 1H), 8.50 (br s, 1H), 8.11 (d, J=8.1 Hz, 2H), 7.40 (d, J=8.1 Hz, 2H), 2.83 (s, 3H), 2.43-2.55 (m, 1H), 0.99-1.15 (m, 2H), 0.82-0.86 (m, 2H).

Example 42

Preparation of methyl 8-(1-(tert-butoxycarbonyl)-1,2,3,6-tetrahydropyridin-4-yl)-1-cyclopropyl-9-methyl-4-oxo-4H-quinolizine-3-carboxylate

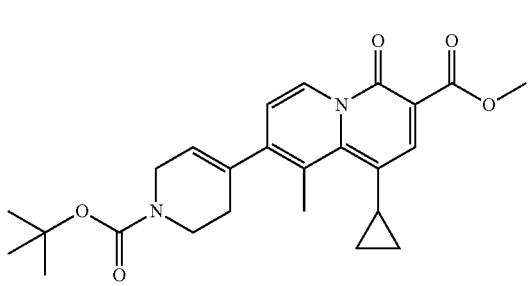 [SMILES: COC(=O)c1cc(C2CC2)c2c(C)c(C3=CCN(C(=O)OC(C)(C)C)CC3)ccn2c1=O]

Methyl 8-(1-(tert-butoxycarbonyl)-1,2,3,6-tetrahydropyridin-4-yl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and tert-butyl 4-(4,4,5,5-tetramethyl-1,3,2-dioxaborolan-2-yl)-5,6-dihydropyridine-1(2H)-carboxylate (467.0 mg, 1.51 mmol). Purification by flash silica column chromatography (CH$_2$Cl$_2$: MeOH) (1:0 to 9:1) afforded the title compound as a brown oil (830 mg, 100%). ESI-MS m/z: 461 (M+Na)$^+$, 439 (M+H)$^+$.

Preparation of 8-(1-(tert-butoxycarbonyl)-1,2,3,6-tetrahydropyridin-4-yl)-1-cyclopropyl-9-methyl-4-oxo-4H-quinolizine-3-carboxylic acid

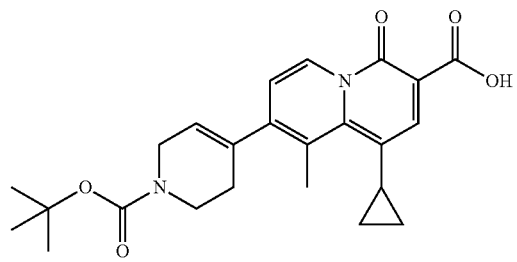 [SMILES: Cc1c(C2=CCN(C(=O)OC(C)(C)C)CC2)ccn2c(=O)c(C(=O)O)cc(C3CC3)c12]

8-(1-(tert-Butoxycarbonyl)-1,2,3,6-tetrahydropyridin-4-yl)-1-cyclopropyl-9-methyl-4-oxo-4H-quinolizine-3-carboxylic acid was prepared according to General Procedure B using methyl 8-(1-(tert-butoxycarbonyl)-1,2,3,6-tetrahydropyridin-4-yl)-1-cyclopropyl-9-methyl-4-oxo-4H-quinolizine-3-carboxylate (830 mg, 1.89 mmol) to afford the title compound as a brown oil (628 mg, 78%). ESI-MS m/z: 425 (M+H)$^+$.

Preparation of EXAMPLE 42 1-cyclopropyl-9-methyl-4-oxo-8-(1,2,3,6-tetrahydropyridin-4-yl)-4H-quinolizine-3-carboxylic acid

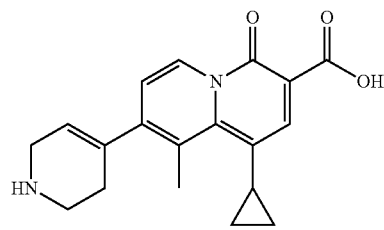 [SMILES: Cc1c(C2=CCNCC2)ccn2c(=O)c(C(=O)O)cc(C3CC3)c12]

1-Cyclopropyl-9-methyl-4-oxo-8-(1,2,3,6-tetrahydropyridin-4-yl)-4H-quinolizine-3-carboxylic acid was prepared according to General Procedure C using 8-(1-(tert-butoxycarbonyl)-1,2,3,6-tetrahydropyridin-4-yl)-1-cyclopropyl-9-methyl-4-oxo-4H-quinolizine-3-carboxylic acid and purified by preparative LCMS to afford the title compound EXAMPLE 42 as a yellow solid (164 mg, 47%). ESI-MS m/z: 325 (M+H)$^+$; $^1$H NMR (400 MHz, DMSO-d6) δ ppm: 14.05 (s, 1H), 9.32 (d, J=7.3 Hz, 1H), 8.25 (s, 1H), 7.41 (d, J=7.3 Hz, 1H), 5.91 (s, 1H), 3.79 (s, 2H), 3.39-3.41 (m, 2H), 2.93 (s, 3H), 2.54-2.59 (s, 2H), 2.40-2.60 (m, 1H), 1.03-1.11 (m, 2H), 0.73-0.77 (m, 2H).

Example 43

Preparation of methyl 8-(1-(tert-butoxycarbonyl)-1H-pyrrol-3-yl)-1-cyclopropyl-9-methyl-4-oxo-4H-quinolizine-3-carboxylate

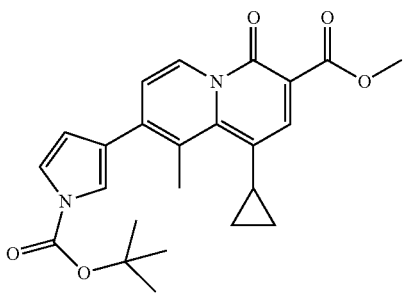 [SMILES: COC(=O)c1cc(C2CC2)c2c(C)c(-c3ccn(C(=O)OC(C)(C)C)c3)ccn2c1=O]

Methyl 8-(1-(tert-butoxycarbonyl)-1H-pyrrol-3-yl)-1-cyclopropyl-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (100 mg, 0.34 mmol) and tert-butyl 3-(4,4,5,5-tetramethyl-1,3,2-dioxaborolan-2-yl)-1H-pyrrole-1-carboxylate (151.0 mg, 0.51 mmol). Purification by flash silica column chromatography ($CH_2Cl_2$:MeOH) (1:0 to 94:6) afforded the title compound as a yellow solid (89 mg, 61%). ESI-MS m/z: 423 $(M+H)^+$.

Preparation of EXAMPLE 43 1-cyclopropyl-9-methyl-4-oxo-8-(1H-pyrrol-3-yl)-4H-quinolizine-3-carboxylic acid

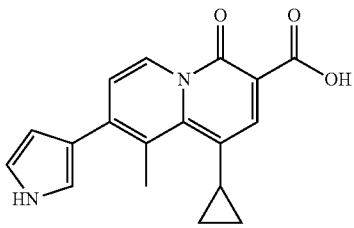 [SMILES: Cc1c(-c2cc[nH]c2)ccn2c(=O)c(C(=O)O)cc(C3CC3)c12]

1-cyclopropyl-9-methyl-4-oxo-8-(1H-pyrrol-3-yl)-4H-quinolizine-3-carboxylic acid was prepared according to General Procedure B using methyl 8-(1-(tert-butoxycarbonyl)-1H-pyrrol-3-yl)-1-cyclopropyl-9-methyl-4-oxo-4H-quinolizine-3-carboxylate (89 mg, 0.22 mmol) followed by BOC removal according to General Procedure C. Purification by preparative LCMS afforded the title compound EXAMPLE 43 as a yellow solid (22 mg, 7% over 2 steps). ESI-MS m/z: 309 $(M+H)^+$; $^1H$ NMR (400 MHz, DMSO-d6) δ ppm: 14.14 (s, 1H), 11.58 (s, 1H), 9.18 (d, J=7.6 Hz, 1H), 8.14 (s, 1H), 7.78 (d, J=7.6 Hz, 1H), 7.53 (s, 1H), 7.01 (s, 1H), 6.64 (s, 1H), 3.04 (s, 3H), 2.50-2.60 (m, 1H), 1.03-1.12 (m, 2H), 0.68-0.72 (m, 2H).

Example 44

Preparation of ethyl 1-cyclopropyl-8-(4-fluoro-phenyl)-9-methyl-4-oxo-4H-quinolizine-3-carboxylate

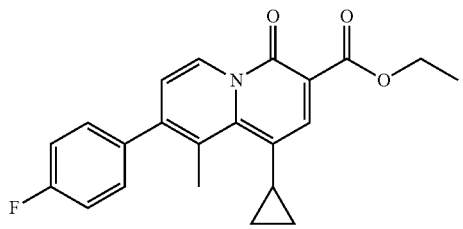 [SMILES: CCOC(=O)c1cc(C2CC2)c2c(C)c(-c3ccc(F)cc3)ccn2c1=O]

A mixture of ethyl 8-chloro-1-cyclopropyl-9-methyl-4-oxo-4H-quinolizine-3-carboxylate (120 mg, 0.400 mmol), 4-fluoro-phenyl boronic acid (67 mg, 0.48 mmol), $(Ph_3P)_2PdCl_2$ (28 mg, 0.040 mmol), and $Na_2CO_3$ (190 mg in 0.8 mL of water, 1.80 mmol) in THF (5 mL) was degassed 3 times under $N_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl acetate, 1:2) to afford the title compound as a yellow solid (120 mg, 82%). ESI-MS m/z: 366 $(M+H)^+$.

Preparation of EXAMPLE 44 1-cyclopropyl-8-(4-fluoro-phenyl)-9-methyl-4-oxo-4H-quinolizine-3-carboxylic acid

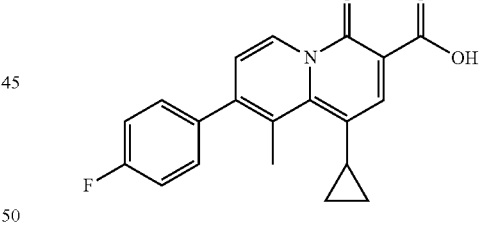

A solution of ethyl 1-cyclopropyl-8-(4-fluoro-phenyl)-9-methyl-4-oxo-4H-quinolizine-3-carboxylate (120 mg, 0.329 mmol) in THF (6 mL) and water (2 mL) was treated with LiOH (55 mg, 1.31 mmol). The reaction was heated to 60° C. for 2 h and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 44 as a yellow solid (110 mg, 99%). ESI-MS m/z: 338 $(M+H)^+$; $^1H$ NMR (300 MHz, DMSO-d6) δ ppm: 9.37 (d, J=7.5 Hz, 1H), 8.30 (s, 1H), 7.70-7.61 (m, 3H), 7.51-7.45 (m, 2H), 2.89 (s, 3H), 2.53-2.51 (m, 1H), 1.13-1.10 (m, 2H), 0.83-0.82 (m, 2H).

Example 45

Preparation of ethyl 1-cyclopropyl-8-(4-chloro-phenyl)-9-methyl-4-oxo-4H-quinolizine-3-carboxylate

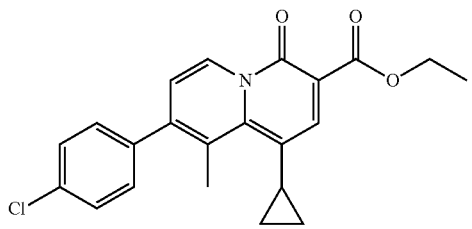 [SMILES: CCOC(=O)c1cc(C2CC2)c2c(C)c(-c3ccc(Cl)cc3)ccn2c1=O]

A mixture of 8-chloro-1-cyclopropyl-9-methyl-4-oxo-4H-quinolizine-3-carboxylic acid ethyl ester (120 mg, 0.400 mmol), 4-chloro-phenyl boronic acid (75 mg, 0.48 mmol), $(Ph_3P)_2PdCl_2$ (28 mg, 0.040 mmol), and $Na_2CO_3$ (190 mg in 0.8 mL of water, 1.80 mmol) in THF (5 mL) was degassed 3 times under $N_2$ and heated to 80° C. overnight. The reaction mixture was diluted with ethyl acetate (50 mL), and washed with water (2×20 mL). The organic phase was separated, dried, and concentrated. The residue was purified by flash silica column chromatography (hexane:ethyl, acetate 2:3) to afford the title compound as a yellow solid (95 mg, 62%). ESI-MS m/z: 382 $(M+H)^+$.

Preparation of EXAMPLE 45 1-cyclopropyl-8-(4-chloro-phenyl)-9-methyl-4-oxo-4H-quinolizine-3-carboxylic acid

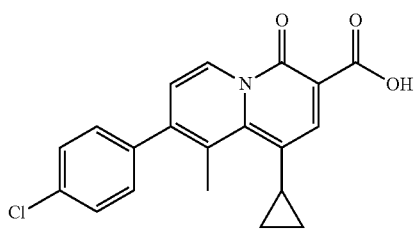 [SMILES: Cc1c(-c2ccc(Cl)cc2)ccn2c(=O)c(C(=O)O)cc(C3CC3)c12]

A solution of ethyl 1-cyclopropyl-8-(4-chloro-phenyl)-9-methyl-4-oxo-4H-quinolizine-3-carboxylate (95 mg, 0.249 mmol) in THF (6 mL) and water (2 mL) was treated with LiOH (43 mg, 1.02 mmol). The reaction was heated to 60° C. for 4 h and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 45 as yellow solid (49 mg, 56%). ESI-MS m/z: 354 $(M+H)^+$; $^1H$ NMR (300 MHz, DMSO-d6) δ ppm: 9.34 (d, J=7.2 Hz, 1H), 8.27 (s, 1H), 7.68-7.56 (m, 5H), 2.84 (s, 3H), 2.55-2.52 (m, 1H), 2.39 (s, 3H), 1.08-1.05 (m, 2H), 0.80-0.78 (m, 2H).

Example 46

Preparation of methyl 1-cyclopropyl-8-(4-hydroxy-phenyl)-9-methyl-4-oxo-4H-quinolizine-3-carboxylate

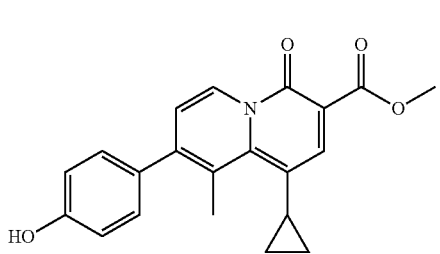 [SMILES: COC(=O)c1cc(C2CC2)c2c(C)c(-c3ccc(O)cc3)ccn2c1=O]

Methyl 1-cyclopropyl-8-(4-hydroxy-phenyl)-9-methyl-4-oxo-4H-quinolizine-3-carboxylate was prepared according to General Procedure A using methyl 8-chloro-1-cyclopropyl-9-methyl-4-oxo-4H-quinolizine-3-carboxylate (500 mg, 1.71 mmol) and 4-hydroxy-phenyl-boronic acid (283 mg, 2.06 mmol). Purification by flash silica column chromatography ($CH_2Cl_2$:MeOH) (1:0 to 9:1) afforded the title compound as a yellow solid (610 mg, 100%). ESI-MS m/z: 388 $(M+K)^+$, 372 $(M+Na)^+$, 350 $(M+H)^+$.

Preparation of EXAMPLE 46 1-cyclopropyl-8-(4-hydroxy-phenyl)-9-methyl-4-oxo-4H-quinolizine-3-carboxylic acid

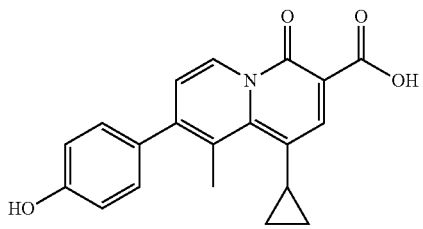 [SMILES: Cc1c(-c2ccc(O)cc2)ccn2c(=O)c(C(=O)O)cc(C3CC3)c12]

1-Cyclopropyl-8-(4-hydroxy-phenyl)-9-methyl-4-oxo-4H-quinolizine-3-carboxylic acid was prepared according to General Procedure B using methyl 1-cyclopropyl-8-(4-hydroxy-phenyl)-9-methyl-4-oxo-4H-quinolizine-3-carboxylate (610 mg, 1.74 mmol) to afford the title compound EXAMPLE 46 as a yellow solid (383 mg, 65%). ESI-MS m/z: 336 $(M+H)^+$, 334.20 $(M-H)^-$; $^1H$ NMR (400 MHz, DMSO-d6) δ ppm: 14.12 (s, 1H), 10.00 (s, 1H), 9.30 (d, J=7.3 Hz, 1H), 8.23 (s, 1H), 7.57 (d, J=7.6 Hz, 1H), 7.43 (d, J=8.6 Hz, 2H), 6.96 (d, J=8.6 Hz, 2H), 2.88 (s, 3H), 2.40-2.60 (m, 1H), 1.05-1.08 (m, 2H), 0.76-0.78 (m, 2H).

Preparation of potassium 1-cyclopropyl-8-(4-hydroxy-phenyl)-9-methyl-4-oxo-4H-quinolizine-3-carboxylate

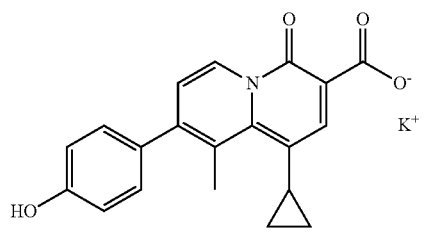 [SMILES: Cc1c(-c2ccc(O)cc2)ccn2c(=O)c(C(=O)[O-])cc(C3CC3)c12 ; [K+]]

Potassium 1-cyclopropyl-8-(4-hydroxy-phenyl)-9-methyl-4-oxo-4H-quinolizine-3-carboxylate was prepared according to General Procedure D using 1-cyclopropyl-8-(4-hydroxy-phenyl)-9-methyl-4-oxo-4H-quinolizine-3-carboxylic acid (370 mg, 0.81 mmol) to afford the K salt of EXAMPLE 46 as a yellow solid (429 mg, 100%). ESI-MS m/z: 336 (M−K+ H)+, 334 (M−K−H)−.

Example 47

Preparation of 1-cyclopropyl-8-(4-methoxy-phenyl)-9-methyl-4-oxo-4H-quinolizine-3-carboxylic acid ethyl ester

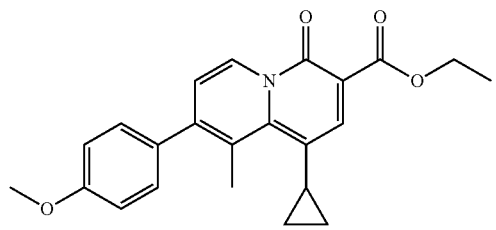 [SMILES: CCOC(=O)c1cc(C2CC2)c2c(C)c(-c3ccc(OC)cc3)ccn2c1=O]

A mixture of 8-chloro-1-cyclopropyl-9-methyl-4-oxo-4H-quinolizine-3-carboxylic acid ethyl ester (120 mg, 0.400 mmol), 4-methoxy-phenyl boronic acid (73 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate, and washed with water. The organic phase was separated, dried, and concentrated. The residue was purified by flash silica column chromatography (hexane:ethyl acetate, 1:2) to afford the title compound as a yellow solid (68 mg, 45%). ESI-MS m/z: 378 (M+H)+.

Preparation of EXAMPLE 47 1-cyclopropyl-8-(4-methoxy-phenyl)-9-methyl-4-oxo-4H-quinolizine-3-carboxylic acid

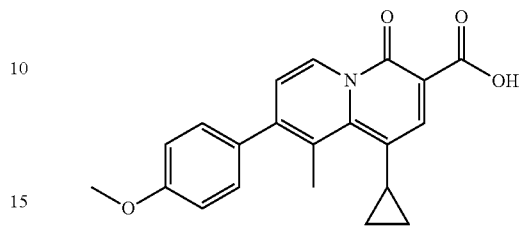

A solution of 1-cyclopropyl-8-(4-methoxy-phenyl)-9-methyl-4-oxo-4H-quinolizine-3-carboxylic acid ethyl ester (68 mg, 0.180 mmol) in THF (6 mL) and water (2 mL) was treated with LiOH (33 mg, 0.78 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 47 as yellow solid (22 mg, 35%). ESI-MS m/z: 350 (M+H)+; $^1$H NMR (300 MHz, DMSO-d6) δ ppm: 9.30 (d, J=7.5 Hz, 1H), 8.23 (s, 1H), 7.57 (d, J=7.5 Hz, 1H), 7.52 (d, J=8.4 Hz, 2H), 7.12 (d, J=7.5 Hz, 2H), 3.84 (s, 3H), 2.86 (s, 3H), 2.53-2.51 (m, 1H), 1.06-1.04 (m, 2H), 0.78-0.75 (m, 2H).

Example 48

Preparation of 1-cyclopropyl-8-(4-hydroxy-methyl-phenyl)-9-methyl-4-oxo-4H-quinolizine-3-carboxylic acid ethyl ester

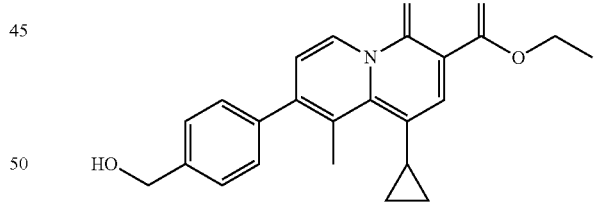

A mixture of 8-chloro-1-cyclopropyl-9-methyl-4-oxo-4H-quinolizine-3-carboxylic acid ethyl ester (120 mg, 0.400 mmol), 4-hydroxy-methyl-phenyl boronic acid (73 mg, 0.48 mmol), (Ph$_3$P)$_2$PdCl$_2$ (28 mg, 0.040 mmol), and Na$_2$CO$_3$ (190 mg in 0.8 mL of water, 1.80 mmol) in THF (5 mL) was degassed 3 times under N$_2$ and heated to 80° C. overnight. The reaction mixture was diluted with ethyl acetate (50 mL) and washed with water (2×20 mL). The organic phase was separated, dried, and concentrated. The residue was purified by flash silica column chromatography (hexane:ethyl acetate, 1:3 to pure ethyl acetate) to afford the title compound as a yellow solid (60 mg, 40%). ESI-MS m/z: 378 (M+H)+.

Preparation of EXAMPLE 48 1-cyclopropyl-8-(4-hydroxy-methyl-phenyl)-9-methyl-4-oxo-4H-quinolizine-3-carboxylic acid

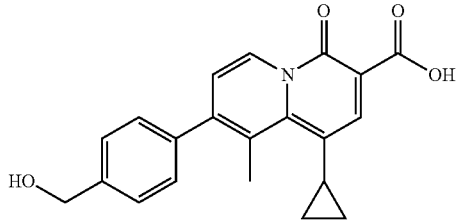 [SMILES: Cc1c(-c2ccc(CO)cc2)ccn2c(=O)c(C(=O)O)cc(C3CC3)c12]

A solution of 1-cyclopropyl-8-(4-hydroxy-methyl-phenyl)-9-methyl-4-oxo-4H-quinolizine-3-carboxylic acid ethyl ester (60 mg, 0.159 mmol) in THF (6 mL) and water (2 mL) was treated with LiOH (27 mg, 0.642 mmol). The reaction was heated to 60° C. overnight and acidified with 1N HCl to pH 4. The precipitate was dissolved with ethyl acetate (50 mL) and washed with brine (2×20 mL). The organic phase was separated, dried, and concentrated. The precipitate was filtered to afford the title compound EXAMPLE 48 as yellow solid (21 mg, 38%). ESI-MS m/z: 350 (M+H)$^+$; $^1$H NMR (300 MHz, DMSO-d6) δ ppm: 9.38 (d, J=7.2 Hz, 1H), 8.30 (s, 1H), 7.62 (d, J=7.5 Hz, 1H), 7.59-7.56 (m, 4H), 5.41 (t, 1H), 4.64 (d, J=5.7 Hz, 2H), 2.91 (s, 3H), 2.54-2.51 (m, 1H), 1.13-1.10 (m, 2H), 0.83-0.81 (m, 2H).

Example 49

Preparation of tert-butyl 4-bromo-2-fluorobenzyl-carbamate

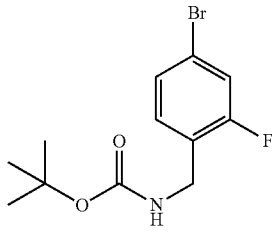 [SMILES: CC(C)(C)OC(=O)NCc1ccc(Br)cc1F]

To a solution of (4-bromo-2-fluorophenyl) methanamine (2.5 g, 12 mmol) in CH$_2$Cl$_2$ (50 mL) at 0° C. was added di-tert-butyl dicarbonate (4.01 g, 18 mmol) and triethylamine (2.6 mL, 18 mmol). The mixture was allowed to warm to room temperature and stirred for 2 h. Water was added (50 mL) and the layers were separated. The organic layer was washed with brine, dried over sodium sulfate and concentrated in vacuo. The crude product was purified by flash silica column chromatography (heptane:ethyl acetate) (1:0 to 4:1) to afford the title compound as a colorless oil. (2.7 g, 71%). $^1$H NMR (400 MHz, DMSO-d6) δ ppm 7.21-7.26 (m, 3H), 4.90 (br s, H), 4.27-4.33 (m, 2H), 1.44 (s, 9H).

Preparation of tert-butyl 2-fluoro-4-(4,4,5,5-tetramethyl-1,3,2-dioxaborolan-2-yl)-benzylcarbamate

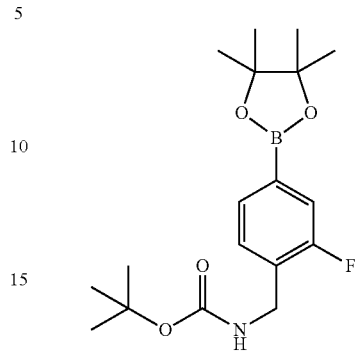

A mixture of tert-butyl 4-bromo-2-fluorobenzyl-carbamate (1.3 g, 4.3 mmol), bis(pinacolato)-diboron (1.6 g, 6.4 mmol), sodium acetate (1.1 g, 13 mmol) in dimethylsulfoxide (dry) (4 mL) was degassed with argon. 1,1'-Bis(diphenylphosphino)-ferrocene palladium(II) dichloride (0.156 g, 0.214 mmol) was added and the mixture was heated at 90° C. for 3 h. After cooling, the reaction mixture was partitioned between ethyl acetate (50 mL) and water (50 mL). The layers were separated and the organic layer was washed with water (50 mL), brine, dried over sodium sulfate and concentrated to give a red/brown crude product. The material was purified by flash silica column chromatography (heptane:ethyl acetate) (1:0 to 4:1) to afford the title compound as a colorless oil (980 mg, 65%). $^1$H NMR (400 MHz, DMSO-d6) δ ppm 7.53 (d, J=7.6 Hz, 1H), 7.45 (d, J=10.4 Hz, 1H), 7.31-7.35 (m, 1H), 4.91 (br s, H), 4.36-4.40 (m, 2H), 1.44 (s, 9H), 1.34 (s, 12H).

Preparation of methyl 8-(4-(((tert-butoxycarbonylamino)-methyl)-3-fluorophenyl)-1-cyclopropyl-9-methyl-4-oxo-4H-quinolizine-3-carboxylate

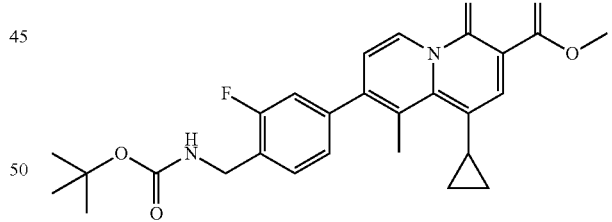

Methyl 8-chloro-1-cyclopropyl-9-methyl-4-oxo-4H-quinolizine-3-carboxylate (46 mg, 0.158 mmol) was dissolved in toluene (500 µL), ethanol (96%) (237 µL) and aqueous sodium carbonate 2M (237 µL, 0.473 mmol). tert-Butyl 2-fluoro-4-(4,4,5,5-tetramethyl-1,3,2-dioxaborolan-2-yl)benzylcarbamate (97 mg, 0.21 mmol) was added. The mixture was degassed with argon and 1,1'-bis(diphenylphosphino)-ferrocene palladium(II) dichloride (11.5 mg, 0.016 mmol) was added. The mixture was heated at 90° C. for 4 h. After cooling, the mixture was diluted with CH$_2$Cl$_2$ (3 mL) and water (3 mL). The layers were separated and the aqueous layer was extracted with CH$_2$Cl$_2$ (3×2 mL). The organic layer was concentrated in vacuo. The crude product was purified with flash silica column chromatography (heptane:ethyl Preparation of 8-(4-((tert-butoxycarbonylamino)methyl)-3-fluorophenyl)-1-cyclopropyl-9-methyl-4-oxo-4H-quinolizine-3-carboxylic acid

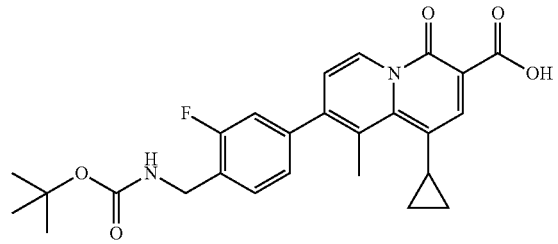 [SMILES: Cc1c(-c2ccc(CNC(=O)OC(C)(C)C)c(F)c2)ccn2c(=O)c(C(=O)O)cc(C3CC3)c12]

Methyl 8-(4-((tert-butoxycarbonylamino)methyl)-3-fluorophenyl)-1-cyclopropyl-9-methyl-4-oxo-4H-quinolizine-3-carboxylate (24 mg, 0.050 mmol) was dissolved in methanol (2 mL) and 1M aqueous sodium hydroxide (0.5 mL, 0.5 mmol) was added. The mixture was stirred at 50° C. for 2 h. After cooling, the methanol was removed in vacuo and the residue was dissolved in water (5 mL) and neutralized with 1M HCl (~0.5 mL). The precipitate formed was extracted with CH$_2$Cl$_2$ (3×4 mL). The organic layer was concentrated to afford the title compound as a yellow solid (20 mg, 86%). ESI-MS m/z: 3467 (M+H)$^+$.

Preparation of EXAMPLE 49 8-(4-(aminomethyl)-3-fluorophenyl)-1-cyclopropyl-9-methyl-4-oxo-4H-quinolizine-3-carboxylic acid hydrochloride

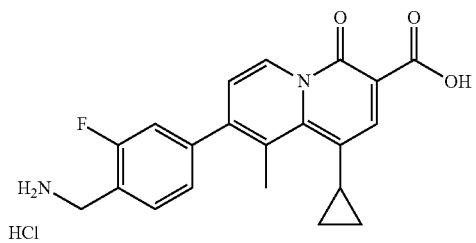 [SMILES: Cc1c(-c2ccc(CN)c(F)c2)ccn2c(=O)c(C(=O)O)cc(C3CC3)c12 ; Cl]

8-(4-((tert-Butoxycarbonylamino)methyl)-3-fluorophenyl)-1-cyclopropyl-9-methyl-4-oxo-4H-quinolizine-3-carboxylic acid (24 mg, 0.051 mmol) was dissolved in acetonitrile (4 mL). HCl 4M in dioxane (1 mL, 4 mmol) was added. The mixture was stirred for 4 h and a suspension was formed affording after filtration the title compound EXAMPLE 49 as a yellow solid (17.7 mg, 86%). ESI-MS m/z: 453 (M+H)$^+$.

Example 50

Preparation of tert-butyl 7-bromo-1-hydroxy-2-oxo-1,2,3,4-tetrahydroquinolin-3-yl-carbamate

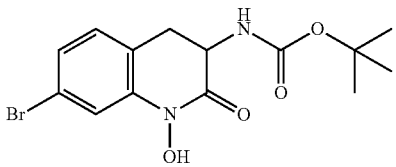 [SMILES: CC(C)(C)OC(=O)NC1Cc2ccc(Br)cc2N(O)C1=O]

To a suspension of 3-amino-7-bromo-1-hydroxy-3,4-dihydroquinolin-2(1H)-one hydrochloride (203 mg, 0.692 mmol) in CH$_2$Cl$_2$ (10 mL) was added di-tert-butyl dicarbonate (226 mg, 1.04 mmol) and triethylamine (0.482 mL, 3.46 mmol). The suspension was stirred at room temperature for 16 h. Water (20 mL) was added to the clear solution and the layers were separated. The organic layer was washed with brine, dried over sodium sulfate and concentrated in vacuo. The crude product was purified by flash silica column chromatography (heptane:ethyl acetate) (1:0 to 7:3) to afford the title compound as a white solid (102 mg, 41%). ESI-MS m/z: 303, 301 (M−tBu+H)$^+$.

Preparation of tert-butyl 2-oxo-7-(4,4,5,5-tetramethyl-1,3,2-dioxaborolan-2-yl)-1,2,3,4-tetrahydroquinolin-3-ylcarbamate

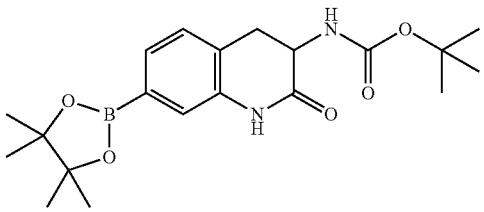 [SMILES: CC(C)(C)OC(=O)NC1Cc2ccc(B3OC(C)(C)C(C)(C)O3)cc2NC1=O]

Sodium acetate (20.7 mg, 0.252 mmol) and bis(pinacolato)diboron (32.0 mg, 0.126 mmol) were placed as solids in a flask under argon. tert-Butyl 7-bromo-1-hydroxy-2-oxo-1,2,3,4-tetrahydroquinolin-3-ylcarbamate (30 mg, 0.084 mmol) in dimethylsulfoxide (dry) (1 mL) was added and the mixture was degassed with argon. trans-Bis(triphenylphosphine)-palladium(II) dichloride (5.9 mg, 8.4 mmol) was added and the reaction mixture was heated at 40° C. for 2 h. After cooling the reaction mixture was concentrated and purified by flash silica column chromatography (heptane:ethyl acetate) (95:5 to 3:2) to afford the title compound as a white solid (13.5 mg, 41%). $^1$H NMR (400 MHz, DMSO-d6) δ ppm 7.78 (s, 1H), 7.46 (d, J=7.6 Hz, 1H), 7.21 (d, J=7.6 Hz, 1H), 5.60 (br s, 1H), (4.34 (br s, 1H), 3.48-3.53 (m, 1H), 2.81-2.89 (m, 2H), 1.47 (s, 9H), 1.34 (s, 12H).

Preparation of methyl 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylate

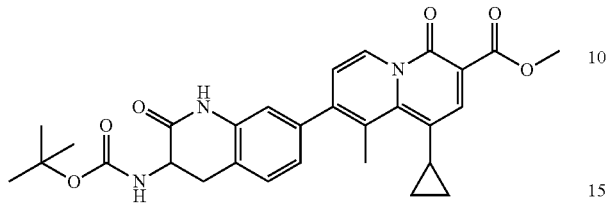

Methyl 8-chloro-1-cyclopropyl-9-methyl-4-oxo-4H-quinolizine-3-carboxylate (45 mg, 0.15 mmol) was dissolved in toluene (330 µL), ethanol (96%) (243 µL) and 2M aqueous sodium carbonate solution (231 µL, 0.463 mmol). tert-Butyl 2-oxo-7-(4,4,5,5-tetramethyl-1,3,2-dioxaborolan-2-yl)-1,2,3,4-tetrahydroquinolin-3-ylcarbamate (78 mg, 0.20 mmol) was added and the mixture was degassed with argon. 1,1'-Bis(diphenylphosphino)-ferrocene palladium(II) dichloride (11.3 mg, 0.015 mmol) was added and the mixture was heated at 80° C. under an argon atmosphere for 16 h. After cooling, the mixture was diluted with $CH_2Cl_2$ (3 mL) and water (3 mL) and the layers were separated. The aqueous layer was extracted with $CH_2Cl_2$ (3×2 mL). The combined organic layers were concentrated and the yellow crude product was purified with flash silica column chromatography (heptane/ethyl acetate) (1:0 to 0:1) to afford the title compound as a yellow solid (43 mg, 53%). ESI-MS m/z: 518 (M+H)$^+$.

Preparation of 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylic acid

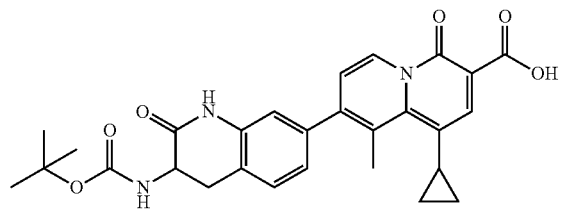 [SMILES: Cc1c(-c2ccc3c(c2)NC(=O)C(NC(=O)OC(C)(C)C)C3)ccn2c(=O)c(C(=O)O)cc(C3CC3)c12]

Methyl 8-(3-(tert-butoxycarbonylamino)-2-oxo-1,2,3,4-tetrahydroquinolin-7-yl)-1-cyclopropyl-9-methyl-4-oxo-4H-quinolizine-3-carboxylate (43 mg, 0.083 mmol) was dissolved in methanol (2 mL) and sodium hydroxide 1M solution in water (0.5 mL, 0.5 mmol) was added. The mixture was stirred at 50° C. for 2 h. After cooling, the methanol was removed in vacuo. The residue was dissolved in water (5 mL) and then neutralized with 1M HCl (~0.5 mL). The precipitate formed was stirred at room temperature overnight. The mixture was extracted with $CH_2Cl_2$ (3×4 mL). The organic layers were concentrated to afford the title compound as a yellow solid (29 mg, 69%). ESI-MS m/z: 504 (M+H)$^+$.

Preparation of EXAMPLE 50 8-(3-amino-2-oxo-1,2,3,4-tetrahydroquinolin-7-yl)-1-cyclopropyl-9-methyl-4-oxo-4H-quinolizine-3-carboxylic acid hydrochloride

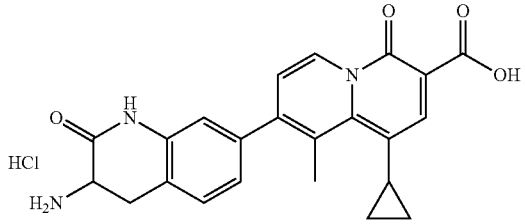 [SMILES: Cl ; Cc1c(-c2ccc3c(c2)NC(=O)C(N)C3)ccn2c(=O)c(C(=O)O)cc(C3CC3)c12]

8-(3-(tert-Butoxycarbonylamino)-2-oxo-1,2,3,4-tetrahydroquinolin-7-yl)-1-cyclopropyl-9-methyl-4-oxo-4H-quinolizine-3-carboxylic acid (29 mg, 0.046 mmol) was dissolved in acetonitrile (4 mL). HCl 4M in dioxane (1 mL, 4 mmol) was added. The mixture was stirred for 4 h and a suspension was formed. The solvents were evaporated and the crude was triturated with diethyl ether (4 mL) to afford the title compound EXAMPLE 50 as a yellow solid (20 mg, 98%). ESI-MS m/z: 404 (M+H)$^+$.

Preparation of potassium salts of EXAMPLES 51 and 52

EXAMPLE 51

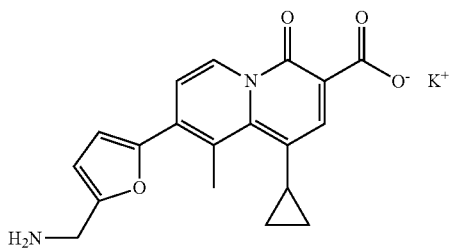

EXAMPLE 52

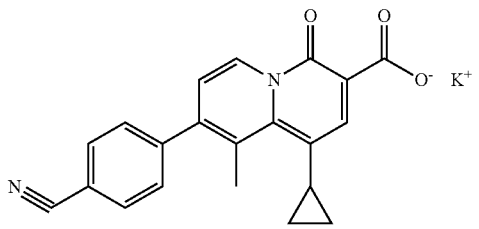

Similarly the potassium salts of EXAMPLES 51 and 52 can be obtained via the application of general procedures A, B, C, and D described earlier.

Biological Example 1

All examples were tested against a select panel of bacterial pathogens. MICs were determined as described in the latest CLSI guidelines—Methods for Dilution Antimicrobial Susceptibility Tests for Bacteria that Grow Aerobically; Approved Standard—Eighth Edition. In brief, a standardized bacterial inoculum containing $5×10^5$ cfu/mL of each strain was exposed to series of 2-fold dilutions of each test compound in 100 μL of Mueller-Hinton Broth (MHB) in 96-well plates. After incubation at 37° C. for 16-20 hours in a humidified incubator, plates were scored visually to determine the lowest test concentration that inhibited visible growth, which corresponds to the Minimum Inhibitory Concentration or MIC. Results are shown for representative gram-positive and gram-negative bacteria in Tables 1 and 2, respectively. Each of the potassium salts tested in Tables 1 and 2 were prepared in situ by titration of a solution of the corresponding free acid with potassium hydroxide.

TABLE 1

MICs (μg/mL) against Gram positive bacteria

| Compounds | S. aureus ATCC 25923 | S. aureus ATCC 43300 (MRSA, FQ-S) | S. aureus BAA-1720 (MRSA, FQ-R) | E. faecium ATCC 19434 | E. faecalis ATCC 29212 | S. pneumonia ATCC 49619 |
|---|---|---|---|---|---|---|
| Example 1 K salt | ≤0.004 | ≤0.004 | 0.125 | 0.25 | 0.008 | 0.016 |
| Example 2 K salt | ≤0.004 | 0.004 | 0.125 | 0.25 | 0.016 | 0.032 |
| Example 3 K salt | 0.016 | 0.016 | 0.5 | 1 | 0.064 | 0.25 |
| Example 4 K salt | 0.016 | 0.016 | 0.25 | 1 | 0.032 | 0.125 |
| Example 5 K salt | 0.008 | 0.008 | 0.25 | 0.5 | 0.016-0.032 | 0.032 |
| Example 6 K salt | 0.008-0.016 | 0.008 | 1 | 1 | 0.016 | 0.032 |
| Example 7 K salt | 0.008 | 0.008 | 0.25 | 0.5 | 0.032 | 0.032-0.064 |
| Example 8 K salt | 0.008 | 0.008 | 0.25 | 0.5 | 0.032 | 0.125 |
| Example 9 K salt | 0.008 | 0.008 | 0.25 | 0.5 | 0.032 | 0.064 |
| Example 10 K salt | 0.008 | 0.008 | 0.5 | 0.5 | 0.032 | 0.125 |
| Example 11 K salt | ≤0.004 | ≤0.004 | 0.125 | 0.25 | 0.016 | 0.032 |
| Example 12 K salt | 0.016-0.032 | 0.016 | 0.5-1 | 1 | 0.064 | 0.25 |
| Example 13 K salt | 0.008-0.016 | 0.008 | 0.25 | 0.5 | 0.016 | 0.032 |
| Example 14 K salt | 0.016 | 0.016 | 0.5 | 8 | 0.064 | 0.125 |
| Example 15 K salt | 0.016 | 0.016 | 1 | >8 | 0.032 | 0.064 |
| Example 16 K salt | 0.016 | 0.016 | 0.5-1 | 1 | 0.064 | 0.125 |
| Example 17 K salt | 0.016 | 0.016 | 1 | 1 | 0.064 | 0.125 |
| Example 18 K salt | 0.008 | 0.008 | 0.25 | 0.25 | 0.032 | 0.064 |
| Example 19 K salt | 0.016 | 0.016 | 0.25 | 1 | 0.032 | 0.064-0.125 |
| Example 20 K salt | 0.032 | 0.016 | 1 | 1 | 0.125 | 0.25 |
| Example 21 K salt | 0.008 | 0.008 | 0.25 | 0.5 | 0.032 | 0.032 |
| Example 22 K salt | 0.008 | 0.016 | 0.5 | 4 | 0.032 | 0.125 |
| Example 23 K salt | ≤0.004 | ≤0.004 | 0.125 | 0.25 | 0.008 | 0.064 |
| Example 24 K salt | 0.032-0.064 | 0.032 | >8 | 0.5 | 0.032 | 0.032 |
| Example 25 K salt | 0.064 | 0.064 | 1 | 8 | 0.125 | 0.25 |
| Example 26 K salt | 0.032 | 0.032 | 1 | 1 | 0.125 | 0.064 |
| Example 27 K salt | 1 | 0.5 | 8 | >8 | 4 | 2 |
| Example 28 K salt | ≤0.004 | ≤0.004 | 0.064 | 0.25 | 0.016 | 0.032 |
| Example 29 K salt | ≤0.004 | 0.008 | 0.125 | 0.5 | 0.008-0.016 | 0.064 |
| Example 30 K salt | 0.064 | 0.032 | 1 | 2 | 0.064 | 0.25 |
| Example 31 K salt | 0.064 | 0.032 | 1 | 2 | 0.25 | 0.125 |
| Example 32 K salt | 0.064 | 0.064 | 1 | 2 | 0.125 | 0.125 |
| Example 33 K salt | 0.016-0.032 | 0.016 | 0.5 | 0.5-1 | 0.064 | 0.25 |
| Example 34 K salt | 0.5 | 0.5 | >8 | >8 | 4 | 2 |
| Example 35 K salt | 0.032 | 0.032 | 0.5 | 2 | 0.125 | 0.032 |
| Example 36 K salt | 0.016-0.032 | 0.016 | 0.5 | 0.5 | 0.032 | 0.064 |
| Example 37 K salt | 2 | 0.125 | 8 | >8 | 0.5 | 1 |
| Example 38 K salt | ≤0.004 | ≤0.004 | 0.064 | >8 | 0.008-0.016 | 0.016 |
| Example 39 K salt | ≤0.004 | ≤0.004 | 0.125 | 0.25 | 0.016 | 0.032 |
| Example 40 K salt | 0.016 | 0.016 | 0.5-1 | 2 | 0.064 | 0.125 |
| Example 41 K salt | 2 | 0.25 | >8 | >8 | 0.25 | 0.5-1 |
| Example 42 | 0.5 | 0.5 | >8 | >8 | 4 | 2 |
| Example 43 K salt | 0.016-0.032 | 0.032 | 2 | 4 | 0.125 | 0.5 |
| Example 44 K salt | 0.016 | 0.016 | 0.5 | 0.5 | 0.064 | 0.25 |
| Example 45 K salt | 0.016-0.032 | 0.016 | 0.5 | 0.5-1 | 0.064 | 0.25 |
| Example 46 K salt | ≤0.004 | ≤0.004 | 0.125 | 0.25 | 0.016 | 0.032 |
| Example 47 K salt | 0.016 | 0.016 | 0.5-1 | 1 | 0.032-0.064 | 0.25 |
| Example 48 K salt | 0.008-0.016 | 0.008 | 0.5 | 1 | 0.032-0.064 | 0.125 |
| Ciprofloxacin | 0.25 | 0.25 | >8 | 8 | 1 | 0.5 |
| Levofloxacin | 0.25 | 0.125 | >8 | 8 | 1 | 0.5 |
| Moxyfloxacin | 0.064 | 0.064 | 4 | 4 | 0.25 | 0.125 |

TABLE 2

MICs (μg/mL) against Gram negative bacteria

| Compounds | E. coli ATCC 25922 | A. baumannii B. ATCC 19606 | P. aeruginosa ATCC 27853 | K. pneumoniae ATCC 33495 | H. influenzae ATCC 49247 | S. maltophilia ATCC 17677 |
|---|---|---|---|---|---|---|
| Example 1 K salt | 0.032-0.064 | 0.064 | 2 | 0.125 | ≤0.004 | 0.125 |
| Example 2 K salt | 0.032 | 0.125 | 1 | 0.125 | ≤0.004 | 0.125 |
| Example 3 K salt | 0.064-0.125 | 0.25 | 2 | 0.25 | 0.016 | 0.25 |
| Example 4 K salt | 0.125 | 0.125 | 8 | 0.25 | 0.008 | 0.25 |
| Example 5 K salt | 0.064 | 0.064 | 2 | 0.125-0.25 | ≤0.004 | 0.125 |
| Example 6 K salt | 0.125 | 0.5 | 8 | 0.5 | ≤0.004 | 0.5 |

TABLE 2-continued

MICs (µg/mL) against Gram negative bacteria

| Compounds | E. coli ATCC 25922 | A. baumannii B. ATCC 19606 | P. aeruginosa ATCC 27853 | K. pneumoniae ATCC 33495 | H. influenzae ATCC 49247 | S. maltophilia ATCC 17677 |
|---|---|---|---|---|---|---|
| Example 7 K salt | 0.064 | 0.125 | 4 | 0.125-0.25 | 0.008 | 0.25 |
| Example 8 K salt | 0.032-0.064 | 0.064-0.125 | 2 | 0.125 | 0.064 | 0.125 |
| Example 9 K salt | 0.064 | 0.125 | 2 | 0.125-0.25 | 0.008 | 0.25 |
| Example 10 K salt | 0.125 | 0.25 | 2 | 0.25 | 0.008 | 0.25-0.5 |
| Example 11 K salt | 0.064 | 0.064 | 2 | 0.125 | ≤0.004 | 0.125 |
| Example 12 K salt | 0.25 | 0.25-0.5 | 8 | 0.5 | 0.032 | 0.5 |
| Example 13 K salt | 0.125 | 0.5 | 8 | 0.5 | 0.016 | 0.5 |
| Example 14 K salt | 0.25 | 0.5-1 | >8 | 1 | 0.016 | 1 |
| Example 15 K salt | 0.125 | 0.5-1 | >8 | 1 | 0.016-0.032 | 0.5 |
| Example 16 K salt | 0.032 | 0.125 | 2 | 0.125 | ≤0.004 | 0.125 |
| Example 17 K salt | 0.064 | 0.125-0.25 | 2-4 | 0.125 | ≤0.004 | 0.25 |
| Example 18 K salt | 0.032 | 0.064 | 1 | 0.064-0.25 | 0.008 | 0.125 |
| Example 19 K salt | 0.064-0.125 | 0.125-0.25 | 2 | 0.25 | 0.008 | 0.25 |
| Example 20 K salt | 0.064 | 0.25 | 2-4 | 0.125-0.25 | ≤0.004 | 0.25 |
| Example 21 K salt | 0.016-0.032 | 0.064-0.125 | 1-2 | 0.064 | ≤0.004 | 0.125 |
| Example 22 K salt | 0.125 | 0.25 | 4 | 0.25 | 0.016 | 0.5 |
| Example 23 K salt | 0.032 | 0.125 | 2 | 0.125 | ≤0.004 | 0.064 |
| Example 24 K salt | 0.125-0.25 | 4 | 8 | 0.5 | 0.016 | >8 |
| Example 25 K salt | 0.5 | 1 | >8 | 1 | 0.064 | 1 |
| Example 26 K salt | ≤0.004 | 0.064 | 0.125 | 0.016 | ≤0.004 | 0.064 |
| Example 27 K salt | 0.064-0.125 | 2 | 2 | 0.25 | 0.125 | 2 |
| Example 28 K salt | 0.032-0.064 | 0.125 | 2 | 0.25-0.5 | ≤0.004 | 0.125 |
| Example 29 K salt | 0.25 | 0.25 | 4 | 0.5-1 | 0.008-0.016 | 0.25 |
| Example 30 K salt | 1 | 1-2 | >8 | 2-4 | 0.064 | 4 |
| Example 31 K salt | 0.032 | 0.25 | 1 | 0.125-0.25 | 0.016 | 0.125 |
| Example 32 K salt | 0.032 | 0.25 | 1 | 0.064.125 | 0.008 | 0.125 |
| Example 33 K salt | 0.25 | 0.5 | 2 | 0.5-1 | 0.016-0.032 | 0.5 |
| Example 34 K salt | 0.064 | 1 | 1 | 0.125-0.5 | 0.064 | 1 |
| Example 35 K salt | 0.032 | 0.25 | 0.5 | 0.125-0.5 | 0.008-0.016 | 0.125 |
| Example 36 K salt | 0.125 | 0.5 | 8 | 0.25 | 0.008 | 0.125 |
| Example 37 K salt | >8 | >8 | >8 | >8 | 0.064 | >8 |
| Example 38 K salt | 0.064-0.125 | 0.125 | >8 | 1-2 | ≤0.004 | 0.25 |
| Example 39 K salt | 0.064 | 0.064 | 2 | 0.125 | ≤0.004 | 0.064 |
| Example 40 K salt | 0.125-0.25 | 0.25 | >8 | 0.5-1 | 0.016 | 0.25 |
| Example 41 K salt | >8 | >8 | >8 | >8 | 0.032 | >8 |
| Example 42 | 0.064 | 2 | 1 | 0.125 | 0.064 | 1 |
| Example 43 K salt | 0.064-0.125 | 0.25 | 4 | 0.125 | 0.008 | 0.25 |
| Example 44 K salt | 0.125 | 0.125-0.25 | 2 | 0.25 | 0.008 | 0.25 |
| Example 45 K salt | 0.25 | 0.25 | 2 | 0.5-1 | 0.016 | 0.25 |
| Example 46 K salt | 0.032 | 0.064 | 1-2 | 0.064 | ≤0.004 | 0.125 |
| Example 47 K salt | 0.25 | 0.5 | 4 | 1-2 | 0.032 | 0.5 |
| Example 48 K salt | 0.064 | 0.125 | 2 | 0.25 | ≤0.004 | 0.25 |
| Ciprofloxacin | 0.008 | 1 | 0.25 | 0.032 | 0.016 | 0.5 |
| Levofloxacin | 0.016 | 0.25 | 1 | 0.032 | 0.016 | 0.25 |
| Moxyfloxacin | 0.032 | 0.5 | 2 | 0.125 | 0.032 | 0.125 |

Biological Example 2

A select number of examples were tested against a broader panel of bacterial pathogens including clinical isolates and quinolone-resistant strains. MICs were determined as described in the latest CLSI guidelines—Methods for Dilution Antimicrobial Susceptibility Tests for Bacteria that Grow Aerobically; Approved Standard—Eighth Edition. In brief, a standardized bacterial inoculum containing $5 \times 10^5$ cfu/mL of each strain was exposed to series of 2-fold dilutions of each test compound in 100 µL of Mueller-Hinton Broth (MHB) in 96-well plates. After incubation at 37° C. for 16-20 hours in a humidified incubator, plates were scored visually to determine the lowest test concentration that inhibited visible growth, which corresponds to the Minimum Inhibitory Concentration or MIC. Results are shown for a selection of various representative bacteria from the Quotient Bioresearch (Cambridgeshire, UK) collection in Tables 3 and 4. The potassium salts of Tables 3 and 4 were prepared synthetically as described in General Procedure D (supra).

TABLE 3

| Cmpd ID | MIC Range (µg/mL) | Staphylococcus aureus (16 strains) | Enterococcus faecalis (5 strains) | Enterococcus faecium (3 strains) | Streptococcus pneumonia (5 strains) | Streptococcus pyogenes (4 strains) | Group C Streptococcus (4 strains) |
|---|---|---|---|---|---|---|---|
| Example 1 K salt | Low | ≤0.015 | 0.12 | 1 | 0.5 | 0.5 | 0.12 |
| | Median | 0.5 | 0.12 | 2 | 0.5 | 0.5 | 0.25 |
| | High | 0.5 | 4 | 8 | 0.5 | 1 | 0.5 |
| Example 2 K salt | Low | ≤0.015 | ≤0.015 | 0.12 | 0.06 | 0.06 | 0.03 |
| | Median | 0.06 | 0.03 | 0.5 | 0.12 | 0.09 | 0.06 |
| | High | 0.25 | 1 | 2 | 0.12 | 0.12 | 0.12 |

TABLE 3-continued

| Cmpd ID | MIC Range (µg/mL) | *Staphylococcus aureus* (16 strains) | *Enterococcus faecalis* (5 strains) | *Enterococcus faecium* (3 strains) | *Streptococcus pneumonia* (5 strains) | *Streptococcus pyogenes* (4 strains) | Group C *Streptococcus* (4 strains) |
|---|---|---|---|---|---|---|---|
| Example 5 | Low | ≤0.015 | 0.03 | 0.25 | 0.12 | 0.12 | 0.06 |
| K salt | Median | 0.12 | 0.06 | 1 | 0.12 | 0.12 | 0.06 |
|  | High | 0.25 | 1 | 4 | 0.25 | 0.5 | 0.12 |
| Example 6 | Low | 0.03 | 0.12 | 1 | 0.25 | 0.12 | 0.06 |
| K salt | Median | 0.5 | 0.25 | 2 | 0.25 | 0.12 | 0.12 |
|  | High | 1 | 4 | 8 | 0.25 | 0.25 | 0.12 |
| Example 16 | Low | ≤0.015 | 0.25 | 1 | 0.5 | 0.25 | 0.25 |
| K salt | Median | 1 | 0.25 | 8 | 0.5 | 0.375 | 0.25 |
|  | High | 1 | 8 | 16 | 1 | 1 | 0.5 |
| Example 21 | Low | ≤0.015 | 0.03 | 0.25 | 0.06 | 0.06 | 0.03 |
| K salt | Median | 0.25 | 0.12 | 1 | 0.06 | 0.06 | 0.03 |
|  | High | 0.5 | 2 | 4 | 0.12 | 0.12 | 0.06 |
| Example 23 | Low | ≤0.015 | ≤0.015 | 0.06 | ≤0.015 | ≤0.015 | ≤0.015 |
| K salt | Median | 0.03 | ≤0.015 | 0.25 | 0.03 | 0.03 | ≤0.015 |
|  | High | 0.12 | 0.25 | 0.5 | 0.03 | 0.03 | 0.03 |
| Example 28 | Low | ≤0.015 | ≤0.015 | 0.12 | 0.03 | 0.03 | 0.03 |
| K salt | Median | 0.06 | 0.25 | 0.25 | 0.06 | 0.06 | 0.045 |
|  | High | 0.12 | 0.5 | 1 | 0.06 | 0.06 | 0.06 |
| Example 31 | Low | ≤0.015 | 0.06 | 0.5 | 0.06 | 0.06 | 0.06 |
| K salt | Median | 0.5 | 0.12 | 4 | 0.12 | 0.09 | 0.09 |
|  | High | 2 | 4 | 8 | 0.25 | 0.25 | 0.12 |
| Example 39 | Low | ≤0.015 | ≤0.015 | 0.12 | 0.12 | 0.06 | 0.03 |
| K salt | Median | 0.06 | 0.03 | 0.5 | 0.12 | 0.12 | 0.09 |
|  | High | 0.12 | 0.5 | 1 | 0.25 | 0.25 | 0.12 |
| Example 42 | Low | 0.5 | 4 | 16 | 4 | 2 | 2 |
|  | Median | 16.25 | 4 | >32 | 4 | 3 | 2 |
|  | High | 32 | 32 | >32 | 8 | 8 | 4 |
| Example 46 | Low | ≤0.015 | ≤0.015 | 0.12 | 0.06 | 0.03 | 0.03 |
| K salt | Median | 0.06 | 0.03 | 0.5 | 0.06 | 0.06 | 0.045 |
|  | High | 0.12 | 0.5 | 1 | 0.12 | 0.12 | 0.06 |
| Levofloxacin | Low | 0.12 | 1 | 2 | 0.5 | 0.5 | 0.5 |
|  | Median | 0.25 | 2 | ≥16 | 1 | 0.75 | 0.75 |
|  | High | ≥16 | ≥16 | ≥16 | 2 | 2 | 1 |

TABLE 4

| Cmpd ID | MIC Range (µg/mL) | *Escherichia coli* (6 strains) | *Klebsiella pneumonia* (4 strains) | *Pseudomonas aeruginosa* (12 strains) | *Burkholderia cepacia* (5 strains) | *Haemophilus influenza* (5 strains) | *Acinetobacter baumannii* (12 strains) |
|---|---|---|---|---|---|---|---|
| Example 1 | Low | 0.06 | 0.5 | 2 | 0.5 | ≤0.015 | 0.25 |
| K salt | Median | >32 | 16 | 16 | 1 | ≤0.015 | 20 |
|  | High | >32 | >32 | 32 | 2 | 0.03 | >32 |
| Example 2 | Low | ≤0.015 | 0.12 | 0.5 | 0.06 | ≤0.015 | 0.06 |
| K salt | Median | 16 | 10 | 4 | 0.12 | ≤0.015 | 6 |
|  | High | 16 | 16 | 16 | 0.25 | ≤0.015 | 16 |
| Example 5 | Low | 0.03 | 0.12 | 1 | 0.12 | ≤0.015 | 0.06 |
| K salt | Median | 8 | 10 | 4 | 0.25 | ≤0.015 | 6 |
|  | High | 16 | 16 | 16 | 0.5 | ≤0.015 | 16 |
| Example 6 | Low | 0.25 | 1 | 8 | 1 | 0.03 | 1 |
| K salt | Median | >32 | >32 | >32 | 2 | 0.03 | >32 |
|  | High | >32 | >32 | >32 | 4 | 0.06 | >32 |
| Example 16 | Low | 0.03 | 0.12 | 2 | 0.25 | ≤0.015 | 0.12 |
| K salt | Median | >32 | 16 | 16 | 0.25 | ≤0.015 | 16 |
|  | High | >32 | >32 | >32 | 0.5 | ≤0.015 | >32 |
| Example 21 | Low | ≤0.015 | 0.06 | 0.5 | 0.12 | ≤0.015 | 0.03 |
| K salt | Median | 16 | 9 | 8 | 0.25 | ≤0.015 | 4 |
|  | High | 32 | 32 | 32 | 0.25 | ≤0.015 | 16 |
| Example 23 | Low | ≤0.015 | 0.06 | 0.25 | ≤0.015 | ≤0.015 | 0.03 |
| K salt | Median | 4 | 5 | 2 | 0.06 | ≤0.015 | 3 |
|  | High | 16 | 16 | 16 | 0.25 | ≤0.015 | 8 |
| Example 28 | Low | 0.03 | 0.12 | 1 | 0.12 | ≤0.015 | 0.06 |
| K salt | Median | 16 | 18 | 6 | 0.25 | ≤0.015 | 8 |
|  | High | 32 | >32 | >32 | 0.5 | ≤0.015 | 16 |
| Example 31 | Low | ≤0.015 | 0.03 | 0.5 | 0.12 | ≤0.015 | 0.03 |
| K salt | Median | 8 | 9 | 8 | 0.5 | ≤0.015 | 8 |
|  | High | 32 | 32 | >32 | 1 | ≤0.015 | >32 |
| Example 39 | Low | ≤0.015 | 0.12 | 0.5 | 0.06 | ≤0.015 | 0.06 |
| K salt | Median | 12 | 9 | 4 | 0.25 | ≤0.015 | 4 |
|  | High | 16 | 32 | 16 | 0.5 | ≤0.015 | 16 |
| Example 42 | Low | 0.06 | 0.12 | 1 | 2 | 0.03 | 0.25 |
|  | Median | 32 | 8 | 32 | 2 | 0.06 | >32 |
|  | High | >32 | >32 | >32 | 2 | 0.06 | >32 |

TABLE 4-continued

| Cmpd ID | MIC Range (μg/mL) | Escherichia coli (6 strains) | Klebsiella pneumonia (4 strains) | Pseudomonas aeruginosa (12 strains) | Burkholderia cepacia (5 strains) | Haemophilus influenza (5 strains) | Acinetobacter baumannii (12 strains) |
|---|---|---|---|---|---|---|---|
| Example 46 | Low | ≤0.015 | 0.06 | 0.25 | 0.06 | ≤0.015 | 0.03 |
| K salt | Median | 12 | 18 | 4 | 0.12 | ≤0.015 | 4 |
|  | High | 32 | >32 | >32 | 0.12 | ≤0.015 | 16 |
| Levofloxacin | Low | 0.015 | 0.03 | 1 | 1 | 0.008 | 0.12 |
|  | Median | ≥16 | 2 | ≥16 | 2 | 0.015 | ≥16 |
|  | High | ≥16 | 2 | ≥16 | 2 | 0.015 | ≥16 |

Gram positive strains in Tables 3 and 4 were as follow: The lab ID is the strain catalogue number of the strains of the Quotient Bioresearch (Cambridgeshire, UK) collection.

| Strains ID | Gram positive strains information |
|---|---|
| GP1 | *Staphylococcus aureus* ATCC 29213 - antibiotic-susceptible type strain |
| GP3 | *Staphylococcus aureus* ATCC 43300 - methicillin-resistant type strain |
| GP4 | *Staphylococcus aureus* - methicillin-resistant clinical isolate |
| GP5 | *Staphylococcus aureus* - multi-drug-resistant clinical isolate |
| GP6 | *Staphylococcus aureus* - teicoplanin-intermediate clinical isolate |
| GP31 | MU50 *Staphylococcus aureus* (MRSA) - VISA type strain |
| GP32 | EMRSA3 *Staphylococcus aureus* (MRSA) - SSCmec type 1 |
| GP33 | EMRSA16 *Staphylococcus aureus* (MRSA) - SSCmec type 2 |
| GP34 | EMRSA1 *Staphylococcus aureus* (MRSA) - SSCmec type 3 |
| GP35 | EMRSA15 *Staphylococcus aureus* (MRSA) - SSCmec type 4 |
| GP36 | HT2001254 *Staphylococcus aureus* (MRSA) - PVL positive |
| GP79 | *Staphylococcus aureus* - levofloxacin-resistant clinical isolate, amino acid changes GrlA & GyrA |
| GP80 | *Staphylococcus aureus* - levofloxacin-resistant clinical isolate, amino acid changes GrlA & GyrA |
| GP81 | *Staphylococcus aureus* - levofloxacin-resistant clinical isolate, amino acid changes GrlA & GyrA |
| GP82 | *Staphylococcus aureus* - levofloxacin-resistant clinical isolate, amino acid changes GrlA, GrlB & GyrA |
| GP83 | *Staphylococcus aureus* - levofloxacin-resistant clinical isolate, amino acid changes GrlA, GrlB & GyrA |
| GP7 | *Staphylococcus epidermidis* - antibiotic susceptible clinical isolate |
| GP8 | *Staphylococcus epidermidis* - methicillin-resistant clinical isolate |
| GP9 | *Staphylococcus haemolyticus* - antibiotic susceptible clinical isolate |
| GP10 | *Staphylococcus saprophyticus* - antibiotic susceptible clinical isolate |
| GP11 | *Enterococcus faecalis* - ATCC 29212 antibiotic-susceptible type strain |
| GP64 | *Enterococcus faecalis* - vancomycin-susceptible clinical isolate |
| GP56 | *Enterococcus faecalis* - vancomycin-resistant (VanA) clinical isolate |
| GP14 | *Enterococcus faecalis* - vancomycin-resistant (VanB) clinical isolate |
| GP58 | *Enterococcus faecalis* - high-level gentamicin-resistant clinical isolate |
| GP16 | *Enterococcus faecium* - vancomycin-susceptible clinical isolate |
| GP17 | *Enterococcus faecium* - vancomycin-resistant (VanA) clinical isolate |
| GP18 | *Enterococcus faecium* - vancomycin-resistant (VanB) clinical isolate |
| GP19 | *Enterococcus gallinarum* - vancomycin-resistant (VanC) clinical isolate |
| GP20 | *Streptococcus pneumoniae* - ATCC 49619 antibiotic-susceptible type strain |
| GP21 | *Streptococcus pneumoniae* - penicillin-susceptible clinical isolate |
| GP22 | *Streptococcus pneumoniae* - penicillin-intermediate clinical isolate |
| GP23 | *Streptococcus pneumoniae* - penicillin-resistant clinical isolate |
| GP24 | *Streptococcus pneumoniae* - multi-drug resistant clinical isolate |
| GP59 | *Streptococcus pyogenes* - antibiotic-susceptible clinical isolate |
| GP61 | *Streptococcus pyogenes* - ATCC 19615 |
| GP26 | *Streptococcus pyogenes* - Macrolide (MLS) resistant clinical isolate |
| GP60 | *Streptococcus pyogenes* - Macrolide (M-type) resistance clinical isolate |
| GP37 | *Streptococcus agalactiae* - antibiotic-susceptible clinical isolate |
| GP38 | *Streptococcus agalactiae* - macrolide-resistant clinical isolate |
| GP39 | Group C *Streptococcus* - antibiotic-susceptible clinical isolate |
| GP55 | Group C *Streptococcus* - macrolide-resistant clinical isolate |
| GP41 | Group G *Streptococcus* - antibiotic-susceptible clinical isolate |
| GP42 | Group G *Streptococcus* - macrolide-resistant clinical isolate |
| GP43 | *Streptococcus mitis* - antibiotic-susceptible clinical isolate |
| GP44 | *Streptococcus mitis* - macrolide-resistant clinical isolate |
| GP62 | *Streptococcus constellatus* - antibiotic-susceptible clinical isolate |
| GP63 | *Streptococcus constellatus* - macrolide-resistant clinical isolate |
| GP47 | *Streptococcus oralis* - antibiotic-susceptible clinical isolate |
| GP48 | *Streptococcus oralis* - macrolide-resistant clinical isolate |
| GP49 | *Streptococcus bovis* - antibiotic-susceptible clinical isolate |
| GP50 | *Streptococcus bovis* - macrolide-resistant clinical isolate |
| GP51 | *Streptococcus sanguis* - antibiotic-susceptible clinical isolate |
| GP52 | *Streptococcus sanguis* - macrolide-resistant clinical isolate |
| GP28 | *Corynebacterium jeikeium* - antibiotic-susceptible clinical isolate |
| GP29 | *Corynebacterium jeikeium* - multi-drug resistant clinical isolate |
| GP30 | *Listeria monocytogenes* - antibiotic-susceptible clinical isolate |

Gram negative strains in Tables 3 and 4 were as follow: (The lab ID is the strain catalogue number of the strains of the Quotient Bioresearch (Cambridgeshire, UK) collection)

| Strains ID | Gram negative strain information |
|---|---|
| GN01 | *Escherichia coli* ATCC 25922 - antibiotic-susceptible type strain |
| GN02 | *Escherichia coli* ATCC 35218 - β-lactamase positive type strain |
| GN03 | *Escherichia coli* - multi-drug resistant clinical isolate |
| GN41 | *Escherichia coli* - ESBL - TEM |
| GN42 | *Escherichia coli* - ESBL - CTXM |
| GN43 | *Escherichia coli* - ESBL - SHV |
| GN04 | *Klebsiella aerogenes* NCTC 11228 - antibiotic-susceptible type strain |
| GN05 | *Klebsiella aerogenes* - multi-drug resistant clinical isolate |
| GN44 | *Klebsiella pneumoniae* - ESBL - TEM + SHV |
| GN45 | *Klebsiella pneumoniae* - ESBL - CTXM |
| GN46 | *Klebsiella pneumoniae* - ESBL - SHV |
| GN48 | *Klebsiella pneumoniae* NCTC 13443 - NDM-1 metallo-β-lactamase |
| GN06 | *Enterobacter sp* - antibiotic-susceptible clinical isolate |
| GN07 | *Enterobacter sp* - multi-drug resistant clinical isolate |
| GN08 | *Serratia marcescens* - antibiotic-susceptible clinical isolate |
| GN09 | *Serratia marcescens* - multi-drug resistant clinical isolate |
| GN10 | *Pseudomonas aeruginosa* ATCC 27853 - antibiotic-susceptible type strain |
| GN11 | *Pseudomonas aeruginosa* - multi-drug resistant clinical isolate |
| GN40 | *Pseudomonas aeruginosa* - Liverpool genotype LES 431 |
| GN63 | *Pseudomonas aeruginosa* - levofloxacin-resistant clinical isolate |

| Strains ID | Gram negative strain information |
|---|---|
| GN64 | *Pseudomonas aeruginosa* - levofloxacin-resistant clinical isolate |
| GN65 | *Pseudomonas aeruginosa* - levofloxacin-resistant clinical isolate |
| GN66 | *Pseudomonas aeruginosa* - levofloxacin-resistant clinical isolate |
| GN67 | *Pseudomonas aeruginosa* - levofloxacin-resistant clinical isolate |
| GN68 | *Pseudomonas aeruginosa* - levofloxacin-resistant clinical isolate |
| GN69 | *Pseudomonas aeruginosa* - levofloxacin-resistant clinical isolate |
| GN70 | *Pseudomonas aeruginosa* - levofloxacin-resistant clinical isolate |
| GN71 | *Pseudomonas aeruginosa* - levofloxacin-resistant clinical isolate |
| GN12 | *Stenotrophomonas maltophilia* - antibiotic-susceptible clinical isolate |
| GN13 | *Stenotrophomonas maltophila* - antibiotic-resistant clinical isolate |
| GN14 | *Burkholderia cepacia* - antibiotic-susceptible clinical isolate |
| GN59 | *Burkholderia cepacia* - antibiotic-susceptible clinical isolate |
| GN60 | *Burkholderia cepacia* - antibiotic-susceptible clinical isolate |
| GN61 | *Burkholderia cepacia* - antibiotic-susceptible clinical isolate |
| GN62 | *Burkholderia cepacia* - antibiotic-susceptible clinical isolate |
| GN15 | *Proteus mirabilis* - antibiotic-susceptible clinical isolate |
| GN16 | *Proteus mirabilis* - multi-drug resistant clinical isolate |
| GN19 | *Shigella sp* - antibiotic-susceptible clinical isolate |
| GN20 | *Shigella sp* - multi-drug resistant clinical isolate |
| GN34 | *Morganella morganii* - antibiotic-susceptible clinical isolate |
| GN22 | *Morganella morganii* - multi-drug resistant clinical isolate |
| GN23 | *Providencia stuartii* - antibiotic-susceptible clinical isolate |
| GN24 | *Providencia stuartii* - multi-drug resistant clinical isolate |
| GN25 | *Neisseria meningitidis* - antibiotic-susceptible clinical isolate susceptible |
| GN35 | *Haemophilus influenzae* - β-lactamase negative clinical isolate |
| GN36 | *Haemophilus influenzae* - β-lactamase positive clinical isolate |
| GN37 | *Haemophilus influenzae* β-lactamase negative ampicillin-resistant clinical isolate |
| GN29 | *Moraxella catarrhalis* β-lactamase positive clinical isolate |
| GN30 | *Moraxella catarrhalis* β-lactamase positive clinical isolate |
| GN31 | *Acinetobacter baumannii* - antibiotic-susceptible clinical isolate |
| GN32 | *Acinetobacter baumannii* - multi-drug resistant clinical isolate |
| GN49 | *Acinetobacter baumannii* - levofloxacin-resistant clinical isolate |
| GN50 | *Acinetobacter baumannii* - levofloxacin-resistant clinical isolate |
| GN51 | *Acinetobacter baumannii* - levofloxacin-resistant clinical isolate |
| GN52 | *Acinetobacter baumannii* - levofloxacin-resistant clinical isolate |
| GN53 | *Acinetobacter baumannii* - levofloxacin-resistant clinical isolate |
| GN54 | *Acinetobacter baumannii* - levofloxacin-resistant clinical isolate |
| GN55 | *Acinetobacter baumannii* - levofloxacin-resistant clinical isolate |
| GN56 | *Acinetobacter baumannii* - levofloxacin-resistant clinical isolate |
| GN57 | *Acinetobacter baumannii* - levofloxacin-resistant clinical isolate |
| GN58 | *Acinetobacter baumannii* - levofloxacin-resistant clinical isolate |
| GN38 | *Citrobacter freundii* - antibiotic-susceptible clinical isolate |
| GN39 | *Citrobacter freundii* - resistant clinical isolate |

Biological Example 3

A select number of examples were tested against a collection of bacterial pathogens resistant against quinolones antibiotics. MICs were determined as described in the latest CLSI guidelines—Methods for Dilution Antimicrobial Susceptibility Tests for Bacteria that Grow Aerobically; Approved Standard—Eighth Edition. In brief, a standardized bacterial inoculum containing $5\times10^5$ cfu/mL of each strain was exposed to series of 2-fold dilutions of each test compound in 100 μL of Mueller-Hinton Broth (MHB) in 96-well plates. After incubation at 37° C. for 16-20 hours in a humidified incubator, plates were scored visually to determine the lowest test concentration that inhibited visible growth, which corresponds to the Minimum Inhibitory Concentration or MIC. Results are shown for representative bacteria in Table 5. The potassium salts of Table 5 were prepared synthetically as described in General Procedure D (supra).

TABLE 5

| | MICs (μg/mL) Quotient Bioresearch Strains Catalogue Number | | | | |
|---|---|---|---|---|---|
| | GP5 | GP33 | GP82 | GP14 | GP17 |
| | Strains Description | | | | |
| | *Staphylococcus aureus* multi-drug-resistant clinical isolate | EMRSA16 *Staphylococcus aureus* (MRSA) - SSCmec type 2 | *Staphylococcus aureus* levofloxacin-resistant clinical isolate, amino acid changes GrlA, GrlB & GyrA | *Enterococcus faecalis* vancomycin-resistant (VanB) clinical isolate | *Enterococcus faecium* vancomycin-resistant (VanA) clinical isolate |
| Example 2 K salt | 0.06 | 0.12 | 0.06 | 0.5 | 2 |
| Example 21 K salt | 0.25 | 0.25 | 0.12 | 1 | 4 |
| Example 23 K salt | 0.03 | 0.03 | ≤0.015 | 0.25 | 0.5 |
| Example 28 K salt | 0.06 | 0.06 | 0.03 | 0.25 | 1 |
| Example 46 K salt | 0.06 | 0.06 | 0.03 | 0.5 | 1 |
| Levofloxacin | ≥16 | ≥16 | 8 | ≥16 | ≥16 |

| | MICs (μg/mL) Quotient Bioresearch Strains Catalogue Number | | | | |
|---|---|---|---|---|---|
| | GP24 | GN03 | GN64 | GN24 | GN54 |
| | Strains Description | | | | |
| | *Streptococcus pneumoniae* multi-drug resistant clinical isolate | *Escherichia coli* multi-drug resistant clinical isolate | *Pseudomonas aeruginosa* levofloxacin-resistant clinical isolate | *Providencia stuartii* multi-drug resistant clinical isolate | *Acinetobacter baumannii* levofloxacin-resistant clinical isolate |
| Example 2 K salt | 0.12 | 16 | 2 | 1 | 2 |

TABLE 5-continued

| | | | | | |
|---|---|---|---|---|---|
| Example 21 K salt | 0.12 | 16 | 4 | 2 | 4 |
| Example 23 K salt | 0.03 | 4 | 2 | 1 | 1 |
| Example 28 K salt | 0.06 | 16 | 4 | 1 | 2 |
| Example 46 K salt | 0.12 | 8 | 4 | 2 | 2 |
| Levofloxacin | 2 | ≥16 | ≥16 | ≥16 | ≥16 |

Biological Example 4

A number of examples were tested against a panel of class A and B select biothreat agents as defined by the CDC (Centers for Disease Control and Prevention). MICs were determined as described in the latest CLSI guidelines—Methods for Dilution Antimicrobial Susceptibility Tests for Bacteria that Grow Aerobically; Approved Standard—Eighth Edition. In brief, a standardized bacterial inoculum containing $5 \times 10^5$ cfu/mL of each strain was exposed to series of 2-fold dilutions of each test compound in 100 μL of Mueller-Hinton Broth (MHB) in 96-well plates. After incubation at 37° C. for the indicated time in a humidified incubator, plates were scored visually to determine the lowest test concentration that inhibited visible growth, which corresponds to the Minimum Inhibitory Concentration or MIC. Experiments were performed under Biosafety Level 3 containment. Results are shown for representative bacteria in Table 6. (*F. tularensis and B. abortus were incubated for 48±2 hours; all other strains were incubated for 24±2 hours.) The potassium salts of Table 6 were prepared synthetically as described in General Procedure D (supra).

Biological Example 5

Inhibition of topoisomerases activity was carried out in vitro. A select number of examples were tested against bacterial gyrase and topoisomerase IV as well as human topoisomerases I and II. Protocols TG1003, TG1007, TG1015 and TG1001 from Topogen Inc., Port Orange, USA were used respectively. Results are shown for representative compounds in Table 7. The potassium salts of Table 7 were prepared synthetically as described in General Procedure D (supra).

TABLE 7

| | $IC_{50}$ (μM) | | | |
|---|---|---|---|---|
| Compounds | Gyrase Assay | Topo IV Assay | hTopo II Assay | hTopo I Assay |
| Example 2 K salt | ≤1.42 | 4.43 | | |
| Example 21 K salt | ≤1.49 | ≤2.33 | | |
| Example 23 K salt | ≤1.39 | 4.34 | >35 | >140 |
| Example 28 K salt | 0.68 | ≤8.45 | 68 | 135 |
| Ciprofloxacin | ≤0.75 | ≤4.71 | >150 | >150 |

TABLE 6

| | MIC (μg/mL) | | | | | |
|---|---|---|---|---|---|---|
| Compounds | Bacillus anthracis Ames strain | *Brucella abortus ATCC 23448 | Burkholderia mallei ATCC 23344 | Burkholderia pseudomallei ATCC 23343 | *Francisella tularensis Schu S4 | Yersinia pestis CO92 |
| Example 1 K salt | 0.004 | 0.031 | 0.25-0.5 | 0.5 | 0.016 | 0.031 |
| Example 2 K salt | 0.004 | 0.016-0.031 | 0.063 | 0.063 | 0.016 | 0.031 |
| Example 3 K salt | 0.008 | 0.125 | 0.5-1 | 0.25 | 0.031 | 0.031-0.063 |
| Example 8 K salt | 0.008 | 0.063 | 0.25 | 0.125 | 0.031 | 0.031 |
| Example 9 K salt | 0.008 | 0.063 | 0.125-0.25 | 0.25 | 0.016 | 0.031 |
| Example 16 K salt | 0.016 | 0.063 | 0.125 | 0.125 | 0.016-0.031 | 0.031 |
| Example 20 K salt | 0.031 | 0.063 | 0.125 | 0.25 | 0.008-0.016 | 0.063 |
| Example 21 K salt | 0.016 | 0.063 | 0.125-0.25 | 0.25-0.5 | 0.031 | 0.031 |
| Example 23 K salt | 0.004 | 0.016 | 0.063 | 0.063 | 0.016 | 0.016-0.031 |
| Example 28 K salt | 0.004 | 0.031-0.063 | 0.125-0.25 | 0.125 | 0.008 | 0.016-0.031 |
| Example 31 K salt | 0.016-0.031 | 0.25 | 0.5-1 | 1 | 0.125-0.5 | 0.25 |
| Example 42 | 0.25 | 40575 | 2 | 4 | 0.25-0.5 | 0.5-1 |
| Example 45 K salt | 0.016 | 0.031 | 0.063-0.125 | 0.063-0.125 | 0.008-0.016 | 0.031 |
| Example 46 K salt | 0.004 | 0.031 | 0.063 | 0.063 | 0.016 | 0.008-0.016 |
| Example 48 K salt | 0.008 | 0.031 | 0.125 | 0.125 | 0.016 | 0.031 |
| Ciprofloxacin | 0.063 | 1 | 4 | 4 | 0.063 | 0.25 |

Biological Example 6

Metabolic stability of a select number of examples was tested in liver microsomes+/−addition of S9 fraction as described by Kuhnz, W. and Gieschen, H. (1998), *Drug Metab. Dispos.*, 1120-1127. Test concentration was 1 μM and HPLC/MS-MS was used for detection. Results are shown for representative compounds in Table 8. The potassium salts of Table 8 were prepared synthetically as described in General Procedure D (supra).

TABLE 8

| Compounds | Mean Parent Remaining (%) | | | |
|---|---|---|---|---|
| | Liver microsomes | | Liver microsomes + S9 | |
| | human | mouse | human | mouse |
| Example 2 K salt | 90 | 53 | 95 | 58 |
| Example 21 K salt | 85 | 87 | 93 | 97 |
| Example 23 K salt | 67 | 2 | 80 | 2 |
| Example 28 K salt | 97 | 30 | 93 | 48 |
| Example 46 K salt | 86 | 81 | 97 | 92 |

Biological Example 7

Groups of 21 mice were treated with select examples at 10 mg/kg. Mice were treated either intravenously or orally (by gavage). At predetermined time points (0.25, 0.5, 1, 2, 4, 8 and 24 hours), 3 mice were sacrificed and blood samples drawn by cardiac puncture. Plasma was obtained by centrifugation and stored at −80° C. Plasma samples were analyzed by LC-MS for remaining amounts of compounds. Results are shown for representative compounds in Table 9. The potassium salts of Table 9 were prepared synthetically as described in General Procedure D (supra).

TABLE 9

| Cmpd. | p.o. | | | i.v. | | | |
|---|---|---|---|---|---|---|---|
| | $C_{max}$ (μg/mL) | $AUC_{0-inf}$ (μg-hr/mL) | Elimination Half life (hrs) | $C_{max}$ (μg/mL) | $AUC_{0-inf}$ (μg-hr/mL) | Elimination Half life (hrs) | % F |
| Ex. 2 K salt | 0.394 | 0.642 | 1.513 | 2.104 | 1.344 | 1.477 | 47.77 |
| Ex. 21 K salt | 0.242 | 0.471 | 2.106 | 0.467 | N.A. | 1.315 | N.A. |
| Ex. 23 K salt | 0.866 | 1.75 | 0.988 | 3.432 | 2.038 | 1.162 | 85.87 |
| Ex. 28 K salt | 0.227 | 0.71 | 3.332 | 2.854 | 1.652 | 1.073 | 42.98 |
| Ex. 46 K salt | 0.156 | 0.389 | 4.156 | 1.055 | 0.474 | 1.07 | 82.07 |

Biological Example 8

For in vivo efficacy a mouse thigh model was used. Bacterial strains were injected into both lateral thigh muscles of mice immunosuppressed with cyclophosphamide. The first dose of compound examples was given orally one hour after infection followed by 2 more doses after 8 and 16 hours. Animals were sacrificed 24 hours after infection, the thigh muscles were surgically removed and homogenized, homogenates spread on agar plates in appropriate dilutions and incubated at 37° C. for 24 to 48 hours before counting the number of colony forming units (CFU). Results are shown for representative compounds in Table 10. The potassium salts of Table 10 were prepared synthetically as described in General Procedure D (supra).

TABLE 10

| | Log reduction (LgR) from vehicle control (CFU/g) | | | | |
|---|---|---|---|---|---|
| | Examples | | | | |
| | Example 21 K salt | Example 23 K salt | Example 46 K salt | vancomycin | ciprofloxacin |
| Dosing | 30 mg/kg TDS p.o. | 30 mg/kg TDS p.o. | 30 mg/kg TDS p.o. | 25 mg/kg i.v. once | 20 mg/kg i.v. TDS |
| MRSA ATCC 43300 | 4.93 | 4.66 | 3.76 | 2.71 | 2.36 |
| Dosing | 30 mg/kg TDS p.o. | 30 mg/kg TDS p.o. | 30 mg/kg TDS p.o. | N.A. | 1.5 mg/kg i.v. BD |
| E. coli ATCC 25922 | 3.13 | 2.82 | 0.37 | N.A. | 3.18 |

Biological Example 9

A number of compounds were evaluated for thermodynamic solubility according to the shake flask technique at 200 μM. The solutions were incubated at room temperature for 24 hours before quantification by HPLC detection. Aqueous solubility was evaluated in simulated gastric fluid (SGF), simulated intestinal fluid (SIF) and phosphate buffer saline (PBS) pH 7.4. Aqueous solubility is expressed in Table 11 as mean solubility in μM.

TABLE 11

| | Aqueous Solubility (Mean in μM) | | |
|---|---|---|---|
| Compounds | Simulated Gastric Fluid | Simulated Intestinal Fluid | PBS pH 7.4 |
| Example 2 K salt | 21 | 171 | 28 |
| Example 21 K salt | 200 | 200 | 200 |
| Example 23 K salt | 8 | 105 | 37 |
| Example 28 K salt | 12 | 153 | 6 |
| Example 46 K salt | 7 | 153 | 44 |

We claim:
1. A compound which is 8-(4-amino-2,5-difluorophenyl)-1-cyclopropyl-9-methyl-4-oxo-4H-quinolizine-3-carboxylic acid, or a pharmaceutically acceptable salt thereof.
2. The compound according to claim 1, wherein the compound is a pharmaceutically acceptable salt, and the pharmaceutically acceptable salt is a potassium salt.

* * * * *